United States Patent
Zimmerman et al.

(10) Patent No.: US 10,179,174 B2
(45) Date of Patent: Jan. 15, 2019

(54) METHOD FOR INDUCING AN IMMUNE RESPONSE AND FORMULATIONS THEREOF

(75) Inventors: Daniel H. Zimmerman, Bethesda, MD (US); Eyal Talor, Baltimore, MD (US); Kanta Subbarao, Washington, DC (US); Kobporn Boonnak, Bangkok (TH)

(73) Assignee: Cel-Sci Corp., Vienna, VA (US)

( * ) Notice: Subject to any disclaimer, the term of this patent is extended or adjusted under 35 U.S.C. 154(b) by 0 days.

(21) Appl. No.: 14/122,238

(22) PCT Filed: May 24, 2012

(86) PCT No.: PCT/US2012/039473
§ 371 (c)(1),
(2), (4) Date: Feb. 2, 2015

(87) PCT Pub. No.: WO2012/162564
PCT Pub. Date: Nov. 29, 2012

(65) Prior Publication Data
US 2015/0140065 A1 May 21, 2015

Related U.S. Application Data

(60) Provisional application No. 61/490,050, filed on May 25, 2011, provisional application No. 61/538,427, filed on Sep. 23, 2011, provisional application No. 61/490,056, filed on May 25, 2011.

(51) Int. Cl.
| | | |
|---|---|---|
| A61K 39/00 | (2006.01) | |
| A61K 39/395 | (2006.01) | |
| A61K 39/145 | (2006.01) | |
| A61K 39/385 | (2006.01) | |
| A61K 38/00 | (2006.01) | |
| A61K 47/48 | (2006.01) | |
| A61K 39/12 | (2006.01) | |
| C07K 14/005 | (2006.01) | |
| A61K 47/65 | (2017.01) | |
| A61K 47/64 | (2017.01) | |
| A61K 47/68 | (2017.01) | |

(52) U.S. Cl.
CPC ...... *A61K 47/4833* (2013.01); *A61K 39/0005* (2013.01); *A61K 39/12* (2013.01); *A61K 47/646* (2017.08); *A61K 47/65* (2017.08); *A61K 47/68* (2017.08); *C07K 14/005* (2013.01); *A61K 2039/5154* (2013.01); *A61K 2039/5158* (2013.01); *A61K 2039/6031* (2013.01); *A61K 2039/645* (2013.01); *C12N 2760/16134* (2013.01)

(58) Field of Classification Search
CPC ............ A61K 2300/00; A61K 31/7115; A61K 38/00; A61K 39/0011; C07K 14/005
See application file for complete search history.

(56) References Cited

U.S. PATENT DOCUMENTS

| | | | |
|---|---|---|---|
| 6,096,537 A | 8/2000 | Chappel | |
| 6,100,377 A | 8/2000 | Greene | |
| 6,287,565 B1 | 9/2001 | Zimmerman | |
| 6,358,751 B1 | 3/2002 | Benichou | |
| 6,572,860 B1 | 6/2003 | Zimmerman | |
| 6,995,237 B1 * | 2/2006 | Zimmerman | A61K 39/0008 424/185.1 |
| 2003/0138769 A1 | 7/2003 | Brikett | |
| 2004/0013676 A1 | 1/2004 | Bae | |
| 2004/0057968 A1 * | 3/2004 | Zimmerman | A61K 39/21 424/208.1 |
| 2006/0257420 A1 | 11/2006 | Zimmerman | |

(Continued)

FOREIGN PATENT DOCUMENTS

| | | |
|---|---|---|
| EP | 01598370 | 11/2005 |
| WO | 1996022067 | 7/1996 |

(Continued)

OTHER PUBLICATIONS

Fosgerau et al., "Peptide therapeutics: current status and future directions", Drug Discovery Today, 2015, 20(1):122-128.*
Biospace Life Sciences, Biospace.com, 2009, News:pdf pp. 1-3.*
Benham, Citrullinated peptide dendritic cell immunotherapy in LA risk genotype-positive rheumatoid arthritis patients, Rheumatoid Arthritis, vol. 7, issue 290, pp. 1-12.
U.S. Appl. No. 60/853,814.
Anderton, S.M. Immunology 2001, vol. 104, pp. 367-376.
Bauer et al., "Maximizing Immune Responses: The Effect of Covalent Peptide Linkage to beta-2 Microglobulin," Oncology Research, 2008, pp. 205-216.
Benham, Citrullinated peptide dentritic cell immunotherapy in LA risk genotype-positive rheumatoid arthritis patients, Rheumatoid Arthritis, vol. 7, issue 290, p. 1-12.
European Application 09718824.7 Office Action dated Nov. 29, 2013.

(Continued)

*Primary Examiner* — Barry A Chestnut
(74) *Attorney, Agent, or Firm* — Hahn & Associates; Roger C. Hahn

(57) ABSTRACT

The invention is related to peptide constructs, i.e., polypeptides obtained by linking together two or more peptides based on or derived from different molecules, which are useful in the treatment or prevention of influenza virus and other infectious diseases. Compositions containing the same, methods for producing the same, and methods for using the same are also disclosed, wherein the peptide constructs have the formula $P_1\text{-}x\text{-}P_2$, where $P_2$ is a peptide associated with an infectious agent and $P_1$ is a peptide that will bind to a class of immune cells, such as dendritic cells. The peptide construct can cause the maturation of immature dendritic cells to a more mature state. The peptide construct or the more mature dendritic cell can be administered to a subject to modulate or initiate an immune response against an infectious agent. Dyes, radioisotopes, or therapeutic agents conjugated with the dendritic cells can be used for localization of the immune target and/or prophylactic or therapeutic treatment of the disease.

13 Claims, 11 Drawing Sheets

Specification includes a Sequence Listing.

(56) References Cited

U.S. PATENT DOCUMENTS

| | | |
|---|---|---|
| 2007/0128698 A1 | 6/2007 | Talor |
| 2010/0279401 A1 | 11/2010 | Burrows |
| 2010/0310591 A1 | 12/2010 | Humphreys |
| 2011/0098444 A1 | 4/2011 | Zimmerman |

FOREIGN PATENT DOCUMENTS

| | | |
|---|---|---|
| WO | 1998005684 | 2/1998 |
| WO | 1998006416 | 2/1998 |
| WO | 1999016710 | 4/1999 |
| WO | 1999034827 | 7/1999 |
| WO | 2001012222 | 2/2001 |
| WO | 2001036448 | 5/2001 |
| WO | 2001043695 | 6/2001 |
| WO | 2007058587 | 5/2007 |
| WO | 2007147007 | 12/2007 |
| WO | 2007147007 A2 | 12/2007 |
| WO | 2008043157 | 4/2008 |
| WO | WO2008043157 | 4/2008 |
| WO | 2009114869 | 9/2009 |
| WO | 2010120897 | 10/2010 |
| WO | WO2010120897 * | 10/2010 |
| WO | 2012082803 | 6/2012 |
| WO | WO2012082803 * | 6/2012 |
| WO | 2012162564 | 11/2012 |
| WO | 2012162565 | 11/2012 |
| WO | 2013138871 | 9/2013 |
| WO | WO2013138871 A1 | 9/2013 |

OTHER PUBLICATIONS

European Application 09718824.7 Office Action dated Jul. 7, 2014.
European Application 09718824.7 Office Action dated May 2, 2015.
European Application 09718824.7 Search Report dated Sep. 15, 2011.
European Application No. 14787690.8 Office Action dated Nov. 9, 2017.
European Application No. 14787690.8 Search Opinion and Search Report dated Sep. 28, 2016.
Harley et al., nucleoprotein—influenza A virus (strain A/Shearwater/Aust/1/72[H6N5]). GenBank Direct Submission Asscession A60028, Feb. 26, 1999 [online] [Retrieved on Jun. 6, 1999]. Retrieved from the Internet: ,URL: http://www.ncbi.nlm.nih.gov/protein/A60028>, p. 1.
Herrmann et al. Leflunomide: an immunomodulatory drug for the treatment of rheumatoid arthritis and other autoimmune diseases, Immunopharmacology, May 2000; 47(2-3): 273-289.
Ken S. Rosenthal et al: "J-LEAPs peptide and Leaps dentritic cell vaccines". Microbial Biotechnology, vol. 5, No. 2, Sep. 6, 2011, pp. 203-213, XP055303324.
Kis-Toth et al. ("Arthritogenic T cells drive the recover of autoantibody-producing B cell homeostasis and the adoptive transfer of arthritis in SCID mice" International Immunology v24(8) 2012 pp. 507-517 (Year: 2012).
Krco, C.J., et al. J. lmmunol. 1996; 156:2761-2768.
Lowrie et al., Therapy of tuberculosis in mice by DNA vaccination 1999, Nature, 400:269.
PCT/US2009/037312 International Preliminary Report on Patentability dated Apr. 29, 2011.
PCT/US2009/037312 International Search Report and Written Opinion dated Jul. 28, 2010.
PCT/US2011/0164746 International Preliminary Search Report dated Dec. 18, 2012.
PCT/US2011/64746 ISR, dated Jun. 13, 2012.
PCT/US2012/039473 International Preliminary Report on Patentability dated Nov. 26, 2013.
PCT/US2012/039473 International Search Report and Written Opinion dated Oct. 30, 2012.
PCT/US2012/039474 International Preliminary Search Report dated Nov. 26, 2013.
PCT/US2012/039474 International Search Report and Written Opinion dated Jan. 31, 2013.
PCT/US2014/035757 International Preliminary Search Report dated Oct. 27, 2015 (contents are WO Oct. 7, 2014).
PCT/US2014/035757 international Search Report and written opinion dated Oct. 7, 2014.
Schenk et al. 1999 Immunization with amyloid-beta attenuates Alzheimerdisease-like pathology in the PDAPP mouse Nature 400: 173.
Taylor et al., Cellular Immunology 2010 vol. 262, pp. 1-5, online on Feb 1, 2010" Maturation of dendritic cell precursors into IL12-producing DCs by J-LEAPS immunogens".
Uniport Accession #O 19507, Jan. 1, 1999 and Uniport Accession #O 00664, Jul. 1, 1997.
Zhang et al., "GABAergic signaling facilitate breast cancer metastasis by promoting ERK1/2-dependent phosphorylation", Cancer Letters, 2014, pp. 100-108.
Zimmerman et al. ("LEAPS peptide vaccination alters T cell phenotype and suppresses joint inflammation in a murine nidek if rheumatoid arthritis" Journal of Immunology, vol. 190 (1 supplement) 67.6 May 1, 2013, printed as total of 6 pages, year 2013).

* cited by examiner

SEQUENCE LISTING

<160> NUMBER OF SEQ ID NOS: 226

<210> SEQ ID NO 1
<211> LENGTH: 31
<212> TYPE: PRT
<213> ORGANISM: Artificial Sequence

```
<220> FEATURE:
<223> OTHER INFORMATION: Heteroconjugate construct

<400> SEQUENCE: 1

Asp Leu Leu Lys Asn Gly Glu Arg Ile Glu Lys Val Glu Gly Gly Gly
1               5                   10                  15

Asn Asp Ala Thr Tyr Gln Arg Thr Arg Ala Leu Val Arg Thr Gly
            20                  25                  30

<210> SEQ ID NO 2
<211> LENGTH: 39
<212> TYPE: PRT
<213> ORGANISM: Artificial Sequence
<220> FEATURE:
<223> OTHER INFORMATION: Heteroconjugate construct

<400> SEQUENCE: 2

Asp Leu Leu Lys Asn Gly Glu Arg Ile Glu Lys Val Glu Gly Gly Gly
1               5                   10                  15

Ser Leu Leu Thr Glu Val Glu Thr Pro Ile Arg Asn Glu Trp Gly Cys
            20                  25                  30

Arg Cys Asn Asp Ser Ser Asp
        35

<210> SEQ ID NO 3
<211> LENGTH: 13
<212> TYPE: PRT
<213> ORGANISM: Homo sapiens

<400> SEQUENCE: 3

Asp Leu Leu Lys Asn Gly Glu Arg Ile Glu Lys Val Glu
1               5                   10

<210> SEQ ID NO 4
<211> LENGTH: 15
<212> TYPE: PRT
<213> ORGANISM: Homo sapiens

<400> SEQUENCE: 4

Asp Gly Gln Glu Glu Lys Ala Gly Val Val Ser Thr Gly Leu Ile
1               5                   10                  15

<210> SEQ ID NO 5
<211> LENGTH: 15
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: Terminates in amide

<400> SEQUENCE: 5

Asp Gly Gln Glu Glu Lys Ala Gly Val Val Ser Thr Gly Leu Ile
1               5                   10                  15

<210> SEQ ID NO 6
<211> LENGTH: 15
<212> TYPE: PRT
<213> ORGANISM: Homo sapiens

<400> SEQUENCE: 6

Asn Gly Gln Glu Glu Lys Ala Gly Val Val Ser Thr Gly Leu Ile
1               5                   10                  15
```

```
<210> SEQ ID NO 7
<211> LENGTH: 15
<212> TYPE: PRT
<213> ORGANISM: Influenza virus

<400> SEQUENCE: 7

Asn Asp Ala Thr Tyr Gln Arg Thr Arg Ala Leu Val Arg Thr Gly
1               5                   10                  15

<210> SEQ ID NO 8
<211> LENGTH: 23
<212> TYPE: PRT
<213> ORGANISM: Influenza virus

<400> SEQUENCE: 8

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 9
<211> LENGTH: 16
<212> TYPE: PRT
<213> ORGANISM: Influenza virus

<400> SEQUENCE: 9

Leu Lys Ser Thr Gln Asn Ala Ile Asp Glu Ile Thr Asn Lys Val Asn
1               5                   10                  15

<210> SEQ ID NO 10
<211> LENGTH: 13
<212> TYPE: PRT
<213> ORGANISM: Influenza virus

<400> SEQUENCE: 10

Gly Leu Phe Gly Ala Ile Ala Gly Phe Ile Glu Gly Gly
1               5                   10

<210> SEQ ID NO 11
<211> LENGTH: 32
<212> TYPE: PRT
<213> ORGANISM: Artificial Sequence
<220> FEATURE:
<223> OTHER INFORMATION: Heteroconjugate construct

<400> SEQUENCE: 11

Asp Leu Leu Lys Asn Gly Glu Arg Ile Glu Lys Val Glu Gly Gly Gly
1               5                   10                  15

Leu Lys Ser Thr Gln Asn Ala Ile Asp Glu Ile Thr Asn Lys Val Asn
            20                  25                  30

<210> SEQ ID NO 12
<211> LENGTH: 29
<212> TYPE: PRT
<213> ORGANISM: Artificial Sequence
<220> FEATURE:
<223> OTHER INFORMATION: Heteroconjugate construct

<400> SEQUENCE: 12

Asp Leu Leu Lys Asn Gly Glu Arg Ile Glu Lys Val Glu Gly Gly Gly
1               5                   10                  15

Gly Leu Phe Gly Ala Ile Ala Gly Phe Ile Glu Gly Gly
            20                  25
```

```
<210> SEQ ID NO 13
<211> LENGTH: 34
<212> TYPE: PRT
<213> ORGANISM: Artificial Sequence
<220> FEATURE:
<223> OTHER INFORMATION: Heteroconjugate construct

<400> SEQUENCE: 13
```

Asp Gly Gln Glu Glu Lys Ala Gly Val Val Ser Thr Gly Leu Ile Gly
1               5                   10                  15

Gly Gly Leu Lys Ser Thr Gln Asn Ala Ile Asp Glu Ile Thr Asn Lys
            20                  25                  30

Val Asn

```
<210> SEQ ID NO 14
<211> LENGTH: 31
<212> TYPE: PRT
<213> ORGANISM: Artificial Sequence
<220> FEATURE:
<223> OTHER INFORMATION: Heteroconjugate construct

<400> SEQUENCE: 14
```

Asp Gly Gln Glu Glu Lys Ala Gly Val Val Ser Thr Gly Leu Ile Gly
1               5                   10                  15

Gly Gly Gly Leu Phe Gly Ala Ile Ala Gly Phe Ile Glu Gly Gly
            20                  25                  30

```
<210> SEQ ID NO 15
<211> LENGTH: 33
<212> TYPE: PRT
<213> ORGANISM: Artificial Sequence
<220> FEATURE:
<223> OTHER INFORMATION: Heteroconjugate construct

<400> SEQUENCE: 15
```

Asp Gly Gln Glu Glu Lys Ala Gly Val Val Ser Thr Gly Leu Ile Gly
1               5                   10                  15

Gly Gly Asn Asp Ala Thr Tyr Gln Arg Thr Arg Ala Leu Val Arg Thr
            20                  25                  30

Gly

```
<210> SEQ ID NO 16
<211> LENGTH: 41
<212> TYPE: PRT
<213> ORGANISM: Artificial Sequence
<220> FEATURE:
<223> OTHER INFORMATION: Heteroconjugate construct

<400> SEQUENCE: 16
```

Asp Gly Gln Glu Glu Lys Ala Gly Val Val Ser Thr Gly Leu Ile Gly
1               5                   10                  15

Gly Gly Ser Leu Leu Thr Glu Val Glu Thr Pro Ile Arg Asn Glu Trp
            20                  25                  30

Gly Cys Arg Cys Asn Asp Ser Ser Asp
            35                  40

```
<210> SEQ ID NO 17
<211> LENGTH: 32
<212> TYPE: PRT
<213> ORGANISM: Artificial Sequence
<220> FEATURE:
<223> OTHER INFORMATION: Heteroconjugate construct

<400> SEQUENCE: 17
```

Leu Lys Ser Thr Gln Asn Ala Ile Asp Glu Ile Thr Asn Lys Val Asn
1               5                   10                  15

Gly Gly Gly Asp Leu Leu Lys Asn Gly Glu Arg Ile Glu Lys Val Glu
                20                  25                  30

<210> SEQ ID NO 18
<211> LENGTH: 34
<212> TYPE: PRT
<213> ORGANISM: Artificial Sequence
<220> FEATURE:
<223> OTHER INFORMATION: Heteroconjugate construct

<400> SEQUENCE: 18

Leu Lys Ser Thr Gln Asn Ala Ile Asp Glu Ile Thr Asn Lys Val Asn
1               5                   10                  15

Gly Gly Gly Asp Gly Gln Glu Glu Lys Ala Gly Val Val Ser Thr Gly
                20                  25                  30

Leu Ile

<210> SEQ ID NO 19
<211> LENGTH: 28
<212> TYPE: PRT
<213> ORGANISM: Artificial Sequence
<220> FEATURE:
<223> OTHER INFORMATION: Heteroconjugate construct

<400> SEQUENCE: 19

Gly Leu Phe Gly Ala Ile Ala Gly Phe Ile Glu Gly Gly Gly Gly Asp
1               5                   10                  15

Leu Leu Lys Asn Gly Glu Arg Ile Glu Lys Val Glu
                20                  25

<210> SEQ ID NO 20
<211> LENGTH: 30
<212> TYPE: PRT
<213> ORGANISM: Artificial Sequence
<220> FEATURE:
<223> OTHER INFORMATION: Heteroconjugate construct

<400> SEQUENCE: 20

Gly Leu Phe Gly Ala Ile Ala Gly Phe Ile Glu Gly Gly Gly Gly Asp
1               5                   10                  15

Gly Gln Glu Glu Lys Ala Gly Val Val Ser Thr Gly Leu Ile
                20                  25                  30

<210> SEQ ID NO 21
<211> LENGTH: 39
<212> TYPE: PRT
<213> ORGANISM: Artificial Sequence
<220> FEATURE:
<223> OTHER INFORMATION: Heteroconjugate construct

<400> SEQUENCE: 21

Ser Leu Leu Thr Glu Val Glu Thr Pro Ile Arg Asn Glu Trp Gly Cys
1               5                   10                  15

Arg Cys Asn Asp Ser Ser Asp Gly Gly Asp Leu Leu Lys Asn Gly
                20                  25                  30

Glu Arg Ile Glu Lys Val Glu
            35

<210> SEQ ID NO 22
<211> LENGTH: 41

```
<212> TYPE: PRT
<213> ORGANISM: Artificial Sequence
<220> FEATURE:
<223> OTHER INFORMATION: Heteroconjugate construct

<400> SEQUENCE: 22

Ser Leu Leu Thr Glu Val Glu Thr Pro Ile Arg Asn Glu Trp Gly Cys
1               5                   10                  15

Arg Cys Asn Asp Ser Ser Asp Gly Gly Asp Gly Gln Glu Glu Lys
            20                  25                  30

Ala Gly Val Val Ser Thr Gly Leu Ile
        35                  40

<210> SEQ ID NO 23
<211> LENGTH: 31
<212> TYPE: PRT
<213> ORGANISM: Artificial Sequence
<220> FEATURE:
<223> OTHER INFORMATION: Heteroconjugate construct

<400> SEQUENCE: 23

Asn Asp Ala Thr Tyr Gln Arg Thr Arg Ala Leu Val Arg Thr Gly Gly
1               5                   10                  15

Gly Gly Asp Leu Leu Lys Asn Gly Glu Arg Ile Glu Lys Val Glu
            20                  25                  30

<210> SEQ ID NO 24
<211> LENGTH: 33
<212> TYPE: PRT
<213> ORGANISM: Artificial Sequence
<220> FEATURE:
<223> OTHER INFORMATION: Heteroconjugate construct

<400> SEQUENCE: 24

Asn Asp Ala Thr Tyr Gln Arg Thr Arg Ala Leu Val Arg Thr Gly Gly
1               5                   10                  15

Gly Gly Asp Gly Gln Glu Glu Lys Ala Gly Val Val Ser Thr Gly Leu
            20                  25                  30

Ile

<210> SEQ ID NO 25
<211> LENGTH: 28
<212> TYPE: PRT
<213> ORGANISM: Artificial Sequence
<220> FEATURE:
<223> OTHER INFORMATION: Heteroconjugate construct

<400> SEQUENCE: 25

Asp Leu Leu Lys Asn Gly Glu Arg Ile Glu Lys Val Glu Gly Gly Gly
1               5                   10                  15

Leu Phe Gly Ala Ile Ala Gly Phe Ile Glu Gly Gly
            20                  25

<210> SEQ ID NO 26
<211> LENGTH: 30
<212> TYPE: PRT
<213> ORGANISM: Artificial Sequence
<220> FEATURE:
<223> OTHER INFORMATION: Heteroconjugate construct

<400> SEQUENCE: 26

Asp Gly Gln Glu Glu Lys Ala Gly Val Val Ser Thr Gly Leu Ile Gly
1               5                   10                  15
```

```
Gly Gly Leu Phe Gly Ala Ile Ala Gly Phe Ile Glu Gly Gly
            20                  25                  30
```

<210> SEQ ID NO 27
<211> LENGTH: 30
<212> TYPE: PRT
<213> ORGANISM: Artificial Sequence
<220> FEATURE:
<223> OTHER INFORMATION: Heteroconjugate construct

<400> SEQUENCE: 27

```
Asn Asp Ala Thr Tyr Gln Arg Thr Arg Ala Leu Val Arg Thr Gly Gly
1               5                   10                  15

Gly Asp Leu Leu Lys Asn Gly Glu Arg Ile Glu Lys Val Glu
            20                  25                  30
```

<210> SEQ ID NO 28
<211> LENGTH: 32
<212> TYPE: PRT
<213> ORGANISM: Artificial Sequence
<220> FEATURE:
<223> OTHER INFORMATION: Heteroconjugate construct

<400> SEQUENCE: 28

```
Asn Asp Ala Thr Tyr Gln Arg Thr Arg Ala Leu Val Arg Thr Gly Gly
1               5                   10                  15

Gly Asp Gly Gln Glu Glu Lys Ala Gly Val Val Ser Thr Gly Leu Ile
            20                  25                  30
```

<210> SEQ ID NO 29
<211> LENGTH: 33
<212> TYPE: PRT
<213> ORGANISM: Artificial Sequence
<220> FEATURE:
<223> OTHER INFORMATION: Heteroconjugate construct

<400> SEQUENCE: 29

```
Asn Gly Gln Glu Glu Lys Ala Gly Val Val Ser Thr Gly Leu Ile Gly
1               5                   10                  15

Gly Gly Asn Asp Ala Thr Tyr Gln Arg Thr Arg Ala Leu Val Arg Thr
            20                  25                  30

Gly
```

<210> SEQ ID NO 30
<211> LENGTH: 41
<212> TYPE: PRT
<213> ORGANISM: Artificial Sequence
<220> FEATURE:
<223> OTHER INFORMATION: Heteroconjugate construct

<400> SEQUENCE: 30

```
Asn Gly Gln Glu Glu Lys Ala Gly Val Val Ser Thr Gly Leu Ile Gly
1               5                   10                  15

Gly Gly Ser Leu Leu Thr Glu Val Glu Thr Pro Ile Arg Asn Glu Trp
            20                  25                  30

Gly Cys Arg Cys Asn Asp Ser Ser Asp
        35                  40
```

<210> SEQ ID NO 31
<211> LENGTH: 34
<212> TYPE: PRT
<213> ORGANISM: Artificial Sequence
<220> FEATURE:
<223> OTHER INFORMATION: Heteroconjugate construct

<400> SEQUENCE: 31

Asn Gly Gln Glu Glu Lys Ala Gly Val Val Ser Thr Gly Leu Ile Gly
1               5                   10                  15

Gly Gly Leu Lys Ser Thr Gln Asn Ala Ile Asp Glu Ile Thr Asn Lys
            20                  25                  30

Val Asn

<210> SEQ ID NO 32
<211> LENGTH: 30
<212> TYPE: PRT
<213> ORGANISM: Artificial Sequence
<220> FEATURE:
<223> OTHER INFORMATION: Heteroconjugate construct

<400> SEQUENCE: 32

Asn Asp Ala Thr Tyr Gln Arg Thr Arg Ala Leu Val Arg Thr Gly Asn
1               5                   10                  15

Gly Gln Glu Glu Lys Ala Gly Val Val Ser Thr Gly Leu Ile
            20                  25                  30

<210> SEQ ID NO 33
<211> LENGTH: 38
<212> TYPE: PRT
<213> ORGANISM: Artificial Sequence
<220> FEATURE:
<223> OTHER INFORMATION: Heteroconjugate construct

<400> SEQUENCE: 33

Ser Leu Leu Thr Glu Val Glu Thr Pro Ile Arg Asn Glu Trp Gly Cys
1               5                   10                  15

Arg Cys Asn Asp Ser Ser Asp Asn Gly Gln Glu Glu Lys Ala Gly Val
            20                  25                  30

Val Ser Thr Gly Leu Ile
        35

<210> SEQ ID NO 34
<211> LENGTH: 31
<212> TYPE: PRT
<213> ORGANISM: Artificial Sequence
<220> FEATURE:
<223> OTHER INFORMATION: Heteroconjugate construct

<400> SEQUENCE: 34

Leu Lys Ser Thr Gln Asn Ala Ile Asp Glu Ile Thr Asn Lys Val Asn
1               5                   10                  15

Asn Gly Gln Glu Glu Lys Ala Gly Val Val Ser Thr Gly Leu Ile
            20                  25                  30

<210> SEQ ID NO 35
<211> LENGTH: 27
<212> TYPE: PRT
<213> ORGANISM: Artificial Sequence
<220> FEATURE:
<223> OTHER INFORMATION: Heteroconjugate construct

<400> SEQUENCE: 35

Gly Leu Phe Gly Ala Ile Ala Gly Phe Ile Glu Gly Gly Gly Asp Leu
1               5                   10                  15

Leu Lys Asn Gly Glu Arg Ile Glu Lys Val Glu
            20                  25

<210> SEQ ID NO 36
<211> LENGTH: 29
<212> TYPE: PRT
<213> ORGANISM: Artificial Sequence
<220> FEATURE:
<223> OTHER INFORMATION: Heteroconjugate construct

<400> SEQUENCE: 36

Gly Leu Phe Gly Ala Ile Ala Gly Phe Ile Glu Gly Gly Asp Gly
1               5                   10                  15

Gln Glu Glu Lys Ala Gly Val Val Ser Thr Gly Leu Ile
            20                  25

<210> SEQ ID NO 37
<211> LENGTH: 46
<212> TYPE: PRT
<213> ORGANISM: Artificial Sequence
<220> FEATURE:
<223> OTHER INFORMATION: Heteroconjugate construct

<400> SEQUENCE: 37

Asp Leu Leu Lys Asn Gly Glu Arg Ile Glu Lys Val Glu Gly Gly Gly
1               5                   10                  15

Tyr Ser Val His Gln Arg Ile Asp Val Lys Asp Thr Lys Glu Ala Leu
            20                  25                  30

Glu Lys Ile Glu Glu Glu Gln Asn Lys Ser Lys Lys Lys Ala
        35                  40                  45

<210> SEQ ID NO 38
<211> LENGTH: 30
<212> TYPE: PRT
<213> ORGANISM: Human immunodeficiency virus

<400> SEQUENCE: 38

Tyr Ser Val His Gln Arg Ile Asp Val Lys Asp Thr Lys Glu Ala Leu
1               5                   10                  15

Glu Lys Ile Glu Glu Glu Gln Asn Lys Ser Lys Lys Lys Ala
            20                  25                  30

<210> SEQ ID NO 39
<211> LENGTH: 4
<212> TYPE: PRT
<213> ORGANISM: Artificial Sequence
<220> FEATURE:
<223> OTHER INFORMATION: Heteroconjugate construct

<400> SEQUENCE: 39

Gly Gly Gly Ser
1

<210> SEQ ID NO 40
<211> LENGTH: 9
<212> TYPE: PRT
<213> ORGANISM: Homo sapiens

<400> SEQUENCE: 40

Val Gln Gly Glu Glu Ser Asn Asp Lys
1               5

<210> SEQ ID NO 41
<211> LENGTH: 20
<212> TYPE: PRT
<213> ORGANISM: Influenza virus

<400> SEQUENCE: 41

```
Tyr Leu Glu Glu His Pro Ser Ala Gly Lys Asp Pro Lys Lys Thr Gly
1               5                   10                  15

Gly Pro Ile Tyr
            20

<210> SEQ ID NO 42
<211> LENGTH: 17
<212> TYPE: PRT
<213> ORGANISM: Influenza virus

<400> SEQUENCE: 42

Ala Gln Asn Ala Ile Ser Thr Thr Phe Pro Tyr Thr Gly Asp Pro Pro
1               5                   10                  15

Tyr

<210> SEQ ID NO 43
<211> LENGTH: 19
<212> TYPE: PRT
<213> ORGANISM: Influenza virus

<400> SEQUENCE: 43

Thr Gly Thr Phe Glu Phe Thr Ser Phe Phe Tyr Arg Tyr Gly Phe Val
1               5                   10                  15

Ala Asn Phe

<210> SEQ ID NO 44
<211> LENGTH: 22
<212> TYPE: PRT
<213> ORGANISM: Influenza virus

<400> SEQUENCE: 44

Val Glu Arg Leu Lys His Gly Thr Phe Gly Pro Val His Phe Arg Asn
1               5                   10                  15

Gln Val Lys Ile Arg Arg
            20

<210> SEQ ID NO 45
<211> LENGTH: 20
<212> TYPE: PRT
<213> ORGANISM: Influenza virus

<400> SEQUENCE: 45

Arg Asn Asp Asp Val Asp Gln Ser Leu Ile Ile Ala Ala Arg Asn Ile
1               5                   10                  15

Val Arg Arg Ala
            20

<210> SEQ ID NO 46
<211> LENGTH: 15
<212> TYPE: PRT
<213> ORGANISM: Influenza virus

<400> SEQUENCE: 46

His Gln Leu Leu Arg His Phe Gln Lys Asp Ala Lys Val Leu Phe
1               5                   10                  15

<210> SEQ ID NO 47
<211> LENGTH: 36
<212> TYPE: PRT
<213> ORGANISM: Artificial Sequence
<220> FEATURE:
<223> OTHER INFORMATION: Heteroconjugate construct
```

<400> SEQUENCE: 47

Asp Leu Leu Lys Asn Gly Glu Arg Ile Glu Lys Val Glu Gly Gly
1               5                   10                  15

Tyr Leu Glu Glu His Pro Ser Ala Gly Lys Asp Pro Lys Thr Gly
            20                  25                  30

Gly Pro Ile Tyr
        35

<210> SEQ ID NO 48
<211> LENGTH: 33
<212> TYPE: PRT
<213> ORGANISM: Artificial Sequence
<220> FEATURE:
<223> OTHER INFORMATION: Heteroconjugate construct

<400> SEQUENCE: 48

Asp Leu Leu Lys Asn Gly Glu Arg Ile Glu Lys Val Glu Gly Gly
1               5                   10                  15

Ala Gln Asn Ala Ile Ser Thr Thr Phe Pro Tyr Thr Gly Asp Pro
            20                  25                  30

Tyr

<210> SEQ ID NO 49
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 49

Asp Leu Leu Lys Asn Gly Glu Arg Ile Glu Lys Val Glu Gly Gly
1               5                   10                  15

Thr Gly Thr Phe Glu Phe Thr Ser Phe Phe Tyr Arg Tyr Gly Phe Val
            20                  25                  30

Ala Asn Phe
        35

<210> SEQ ID NO 50
<211> LENGTH: 38
<212> TYPE: PRT
<213> ORGANISM: Artificial Sequence
<220> FEATURE:
<223> OTHER INFORMATION: Heteroconjugate construct

<400> SEQUENCE: 50

Asp Leu Leu Lys Asn Gly Glu Arg Ile Glu Lys Val Glu Gly Gly
1               5                   10                  15

Val Glu Arg Leu Lys His Gly Thr Phe Gly Pro Val His Phe Arg Asn
            20                  25                  30

Gln Val Lys Ile Arg Arg
        35

<210> SEQ ID NO 51
<211> LENGTH: 36
<212> TYPE: PRT
<213> ORGANISM: Artificial Sequence
<220> FEATURE:
<223> OTHER INFORMATION: Heteroconjugate construct

<400> SEQUENCE: 51

Asp Leu Leu Lys Asn Gly Glu Arg Ile Glu Lys Val Glu Gly Gly Gly

```
                1               5                  10                 15
Arg Asn Asp Asp Val Asp Gln Ser Leu Ile Ile Ala Ala Arg Asn Ile
                20                  25                 30

Val Arg Arg Ala
        35

<210> SEQ ID NO 52
<211> LENGTH: 31
<212> TYPE: PRT
<213> ORGANISM: Artificial Sequence
<220> FEATURE:
<223> OTHER INFORMATION: Heteroconjugate construct

<400> SEQUENCE: 52

Asp Leu Leu Lys Asn Gly Glu Arg Ile Glu Lys Val Glu Gly Gly Gly
1               5                  10                 15

His Gln Leu Leu Arg His Phe Gln Lys Asp Ala Lys Val Leu Phe
                20                  25                 30

<210> SEQ ID NO 53
<211> LENGTH: 9
<212> TYPE: PRT
<213> ORGANISM: Adenovirus type 5

<400> SEQUENCE: 53

Thr Asp Leu Gly Gln Asn Leu Leu Tyr
1               5

<210> SEQ ID NO 54
<211> LENGTH: 19
<212> TYPE: PRT
<213> ORGANISM: Adenovirus type 5

<400> SEQUENCE: 54

Ser Met Gly Ala Leu Thr Asp Leu Gly Gln Asn Leu Leu Tyr Ala Asn
1               5                  10                 15

Ser Ala His

<210> SEQ ID NO 55
<211> LENGTH: 9
<212> TYPE: PRT
<213> ORGANISM: Adenovirus type 5

<400> SEQUENCE: 55

Thr Tyr Phe Ser Leu Asn Asn Lys Phe
1               5

<210> SEQ ID NO 56
<211> LENGTH: 19
<212> TYPE: PRT
<213> ORGANISM: Adenovirus type 5

<400> SEQUENCE: 56

Ala Arg Ala Thr Glu Thr Tyr Phe Ser Leu Asn Asn Lys Phe Arg Asn
1               5                  10                 15

Pro Thr Val

<210> SEQ ID NO 57
<211> LENGTH: 9
<212> TYPE: PRT
<213> ORGANISM: Hepatitis C virus

<400> SEQUENCE: 57
```

```
Asp Leu Met Gly Tyr Ile Pro Ala Val
1               5
```

<210> SEQ ID NO 58
<211> LENGTH: 19
<212> TYPE: PRT
<213> ORGANISM: Hepatitis C virus

<400> SEQUENCE: 58

```
Thr Cys Gly Phe Ala Asp Leu Met Gly Tyr Ile Pro Ala Val Gly Ala
1               5                   10                  15

Pro Leu Gly
```

<210> SEQ ID NO 59
<211> LENGTH: 9
<212> TYPE: PRT
<213> ORGANISM: Hepatitis C virus

<400> SEQUENCE: 59

```
Ala Tyr Ser Gln Gln Thr Arg Gly Leu
1               5
```

<210> SEQ ID NO 60
<211> LENGTH: 19
<212> TYPE: PRT
<213> ORGANISM: Hepatitis C virus

<400> SEQUENCE: 60

```
Leu Ala Pro Ile Thr Ala Tyr Ser Gln Gln Thr Arg Gly Leu Leu Gly
1               5                   10                  15

Cys Ile Ile
```

<210> SEQ ID NO 61
<211> LENGTH: 9
<212> TYPE: PRT
<213> ORGANISM: Hepatitis B virus

<400> SEQUENCE: 61

```
Phe Leu Leu Thr Arg Ile Leu Thr Ile
1               5
```

<210> SEQ ID NO 62
<211> LENGTH: 19
<212> TYPE: PRT
<213> ORGANISM: Hepatitis B virus

<400> SEQUENCE: 62

```
Leu Gln Ala Gly Phe Phe Leu Leu Thr Arg Ile Leu Thr Ile Pro Gln
1               5                   10                  15

Ser Leu Asp
```

<210> SEQ ID NO 63
<211> LENGTH: 16
<212> TYPE: PRT
<213> ORGANISM: Hepatitis B virus

<400> SEQUENCE: 63

```
Leu Arg Gly Asp Leu Gln Val Leu Ala Gln Lys Val Ala Arg Thr Leu
1               5                   10                  15
```

<210> SEQ ID NO 64
<211> LENGTH: 23

<212> TYPE: PRT
<213> ORGANISM: Hepatitis B virus

<400> SEQUENCE: 64

Asp Tyr Gln Gly Met Leu Pro Val Cys Pro Leu Ile Pro Gly Ser Ser
1               5                   10                  15

Thr Thr Ser Thr Gly Pro Cys
            20

<210> SEQ ID NO 65
<211> LENGTH: 10
<212> TYPE: PRT
<213> ORGANISM: Human papillomavirus type 16

<400> SEQUENCE: 65

Tyr Met Leu Asp Leu Gln Pro Glu Thr Thr
1               5                   10

<210> SEQ ID NO 66
<211> LENGTH: 20
<212> TYPE: PRT
<213> ORGANISM: Human papillomavirus type 16

<400> SEQUENCE: 66

Pro Thr Leu His Glu Tyr Met Leu Asp Leu Gln Pro Glu Thr Thr Asp
1               5                   10                  15

Leu Tyr Cys Tyr
            20

<210> SEQ ID NO 67
<211> LENGTH: 9
<212> TYPE: PRT
<213> ORGANISM: Human T-cell lymphotropic virus type 1

<400> SEQUENCE: 67

Leu Leu Phe Gly Tyr Pro Val Tyr Val
1               5

<210> SEQ ID NO 68
<211> LENGTH: 19
<212> TYPE: PRT
<213> ORGANISM: Human T-cell lymphotropic virus type 2

<400> SEQUENCE: 68

Gly Phe Gly Gln Ser Leu Leu Phe Gly Tyr Pro Val Tyr Val Phe Gly
1               5                   10                  15

Asp Cys Val

<210> SEQ ID NO 69
<211> LENGTH: 9
<212> TYPE: PRT
<213> ORGANISM: respiratory syncytial virus

<400> SEQUENCE: 69

Lys Met Leu Lys Glu Met Gly Glu Val
1               5

<210> SEQ ID NO 70
<211> LENGTH: 19
<212> TYPE: PRT
<213> ORGANISM: respiratory syncytial virus

<400> SEQUENCE: 70

Arg Lys Ser Tyr Lys Lys Met Leu Lys Glu Met Gly Glu Val Ala Pro
1               5                   10                  15

Glu Tyr Arg

<210> SEQ ID NO 71
<211> LENGTH: 9
<212> TYPE: PRT
<213> ORGANISM: Vaccinia virus

<400> SEQUENCE: 71

Lys Val Asp Asp Thr Phe Tyr Tyr Val
1               5

<210> SEQ ID NO 72
<211> LENGTH: 18
<212> TYPE: PRT
<213> ORGANISM: Vaccinia virus

<400> SEQUENCE: 72

Val Lys Val Asn Lys Val Asp Asp Thr Phe Tyr Tyr Val Ile Tyr Glu
1               5                   10                  15

Ala Val

<210> SEQ ID NO 73
<211> LENGTH: 10
<212> TYPE: PRT
<213> ORGANISM: Vaccinia virus

<400> SEQUENCE: 73

Arg Leu Asp Asp Asp Gly Asn Phe Gln Leu
1               5                   10

<210> SEQ ID NO 74
<211> LENGTH: 20
<212> TYPE: PRT
<213> ORGANISM: Vaccinia virus

<400> SEQUENCE: 74

Glu Arg Val Asp Val Arg Leu Asp Asp Asp Gly Asn Phe Gln Leu Met
1               5                   10                  15

Asn Asp Pro Gly
            20

<210> SEQ ID NO 75
<211> LENGTH: 9
<212> TYPE: PRT
<213> ORGANISM: Polyomavirus JC/BK

<400> SEQUENCE: 75

Ser Ile Thr Glu Val Glu Cys Phe Leu
1               5

<210> SEQ ID NO 76
<211> LENGTH: 19
<212> TYPE: PRT
<213> ORGANISM: Polyomavirus JC/BK

<400> SEQUENCE: 76

Lys Thr Gly Val Asp Ser Ile Thr Glu Val Glu Cys Phe Leu Thr Pro
1               5                   10                  15

Glu Met Gly

```
<210> SEQ ID NO 77
<211> LENGTH: 9
<212> TYPE: PRT
<213> ORGANISM: Polyomavirus JC/BK

<400> SEQUENCE: 77

Leu Leu Met Trp Glu Ala Val Thr Val
1               5

<210> SEQ ID NO 78
<211> LENGTH: 19
<212> TYPE: PRT
<213> ORGANISM: Polyomavirus JC/BK

<400> SEQUENCE: 78

Leu Thr Cys Gly Asn Leu Leu Met Trp Glu Ala Val Thr Val Lys Thr
1               5                   10                  15

Glu Val Leu

<210> SEQ ID NO 79
<211> LENGTH: 9
<212> TYPE: PRT
<213> ORGANISM: Polyomavirus JC/BK

<400> SEQUENCE: 79

Leu Leu Leu Ile Trp Phe Arg Pro Val
1               5

<210> SEQ ID NO 80
<211> LENGTH: 19
<212> TYPE: PRT
<213> ORGANISM: Polyomavirus JC/BK

<400> SEQUENCE: 80

Gly Met Thr Leu Leu Leu Leu Ile Trp Phe Arg Pro Val Ala Asp
1               5                   10                  15

Phe Ala Thr

<210> SEQ ID NO 81
<211> LENGTH: 9
<212> TYPE: PRT
<213> ORGANISM: Human T-cell lymphotropic virus type 2

<400> SEQUENCE: 81

Leu Leu Tyr Gly Tyr Pro Val Tyr Val
1               5

<210> SEQ ID NO 82
<211> LENGTH: 19
<212> TYPE: PRT
<213> ORGANISM: Human T-cell lymphotropic virus type 3

<400> SEQUENCE: 82

Gly Phe Gly Gln Ser Leu Leu Tyr Gly Tyr Pro Val Tyr Val Phe Gly
1               5                   10                  15

Asp Cys Val

<210> SEQ ID NO 83
<211> LENGTH: 9
<212> TYPE: PRT
<213> ORGANISM: Cytomegalovirus

<400> SEQUENCE: 83
```

```
Val Leu Ala Glu Leu Val Lys Gln Ile
1               5

<210> SEQ ID NO 84
<211> LENGTH: 19
<212> TYPE: PRT
<213> ORGANISM: Cytomegalovirus

<400> SEQUENCE: 84

Asn Pro Glu Lys Asp Val Leu Ala Glu Leu Val Lys Gln Ile Lys Val
1               5                   10                  15

Arg Val Asp

<210> SEQ ID NO 85
<211> LENGTH: 9
<212> TYPE: PRT
<213> ORGANISM: Cytomegalovirus

<400> SEQUENCE: 85

Gln Tyr Asp Pro Val Ala Ala Leu Phe
1               5

<210> SEQ ID NO 86
<211> LENGTH: 19
<212> TYPE: PRT
<213> ORGANISM: Cytomegalovirus

<400> SEQUENCE: 86

Thr Val Glu Leu Arg Gln Tyr Asp Pro Val Ala Ala Leu Phe Phe Phe
1               5                   10                  15

Asp Ile Asp

<210> SEQ ID NO 87
<211> LENGTH: 9
<212> TYPE: PRT
<213> ORGANISM: Epstein Barr Virus

<400> SEQUENCE: 87

Phe Leu Tyr Ala Leu Ala Leu Leu Leu
1               5

<210> SEQ ID NO 88
<211> LENGTH: 19
<212> TYPE: PRT
<213> ORGANISM: Epstein Barr Virus

<400> SEQUENCE: 88

Leu Leu Ala Arg Leu Phe Leu Tyr Ala Leu Ala Leu Leu Leu Leu Ala
1               5                   10                  15

Ser Ala Leu

<210> SEQ ID NO 89
<211> LENGTH: 9
<212> TYPE: PRT
<213> ORGANISM: Epstein Barr Virus

<400> SEQUENCE: 89

Pro Tyr Leu Phe Trp Leu Ala Ala Ile
1               5

<210> SEQ ID NO 90
<211> LENGTH: 19
<212> TYPE: PRT
```

```
<213> ORGANISM: Epstein Barr Virus

<400> SEQUENCE: 90

Pro Val Ile Val Ala Pro Tyr Leu Phe Trp Leu Ala Ala Ile Ala Ala
1               5                   10                  15

Ser Cys Phe

<210> SEQ ID NO 91
<211> LENGTH: 10
<212> TYPE: PRT
<213> ORGANISM: Kaposi's sarcoma-associated herpesvirus

<400> SEQUENCE: 91

Val Leu Leu Asn Gly Trp Arg Trp Arg Leu
1               5                   10

<210> SEQ ID NO 92
<211> LENGTH: 20
<212> TYPE: PRT
<213> ORGANISM: herpes simplex virus 8

<400> SEQUENCE: 92

Val His Val Pro Asp Val Leu Leu Asn Gly Trp Arg Trp Arg Leu Gly
1               5                   10                  15

Ala Ile Pro Pro
            20

<210> SEQ ID NO 93
<211> LENGTH: 9
<212> TYPE: PRT
<213> ORGANISM: Kaposi's sarcoma-associated herpesvirus

<400> SEQUENCE: 93

His Arg Gln Ser Ile Trp Ile Thr Trp
1               5

<210> SEQ ID NO 94
<211> LENGTH: 19
<212> TYPE: PRT
<213> ORGANISM: herpes simplex virus 8

<400> SEQUENCE: 94

Val Glu Gln Ser Gly His Arg Gln Ser Ile Trp Ile Thr Trp His Thr
1               5                   10                  15

Gln Pro Val

<210> SEQ ID NO 95
<211> LENGTH: 15
<212> TYPE: PRT
<213> ORGANISM: Kaposi's sarcoma-associated herpesvirus

<400> SEQUENCE: 95

Leu Val Cys Leu Leu Ala Ile Ser Val Val Pro Pro Ser Gly Gln
1               5                   10                  15

<210> SEQ ID NO 96
<211> LENGTH: 15
<212> TYPE: PRT
<213> ORGANISM: Kaposi's sarcoma-associated herpesvirus

<400> SEQUENCE: 96

Glu Leu Thr Asp Ala Leu Ile Ser Ala Phe Ser Gly Ser Tyr Ser
1               5                   10                  15
```

<210> SEQ ID NO 97
<211> LENGTH: 15
<212> TYPE: PRT
<213> ORGANISM: Kaposi's sarcoma-associated herpesvirus

<400> SEQUENCE: 97

Leu Ile Leu Tyr Leu Cys Val Pro Arg Cys Arg Arg Lys Lys Pro
1               5                   10                  15

<210> SEQ ID NO 98
<211> LENGTH: 9
<212> TYPE: PRT
<213> ORGANISM: Kaposi's sarcoma-associated herpesvirus

<400> SEQUENCE: 98

Ile Ser Ala Arg Gly Gln Glu Leu Phe
1               5

<210> SEQ ID NO 99
<211> LENGTH: 19
<212> TYPE: PRT
<213> ORGANISM: herpes simplex virus 8

<400> SEQUENCE: 99

Gln Ser Arg Arg Ser Ile Ser Ala Arg Gly Gln Glu Leu Phe Arg Thr
1               5                   10                  15

Leu Leu Glu

<210> SEQ ID NO 100
<211> LENGTH: 11
<212> TYPE: PRT
<213> ORGANISM: Varicella zoster

<400> SEQUENCE: 100

Glu Ile Thr Asp Thr Ile Asp Lys Phe Gly Lys
1               5                   10

<210> SEQ ID NO 101
<211> LENGTH: 21
<212> TYPE: PRT
<213> ORGANISM: Varicella zoster

<400> SEQUENCE: 101

Pro Ile Pro Val Ser Glu Ile Thr Asp Thr Ile Asp Lys Phe Gly Lys
1               5                   10                  15

Cys Ser Ser Lys Ala
            20

<210> SEQ ID NO 102
<211> LENGTH: 11
<212> TYPE: PRT
<213> ORGANISM: Varicella zoster

<400> SEQUENCE: 102

Leu Pro Glu Gly Met Asp Pro Phe Ala Glu Lys
1               5                   10

<210> SEQ ID NO 103
<211> LENGTH: 21
<212> TYPE: PRT
<213> ORGANISM: Varicella zoster

<400> SEQUENCE: 103

```
Lys Gly Leu Lys Gln Leu Pro Glu Gly Met Asp Pro Phe Ala Glu Lys
1               5                   10                  15

Pro Asn Ala Thr Asp
            20

<210> SEQ ID NO 104
<211> LENGTH: 11
<212> TYPE: PRT
<213> ORGANISM: Varicella zoster

<400> SEQUENCE: 104

Ala Arg Leu Cys Asp Leu Pro Ala Thr Pro Lys
1               5                   10

<210> SEQ ID NO 105
<211> LENGTH: 21
<212> TYPE: PRT
<213> ORGANISM: Varicella zoster

<400> SEQUENCE: 105

Ala Leu Phe Gln Gln Ala Arg Leu Cys Asp Leu Pro Ala Thr Pro Lys
1               5                   10                  15

Gly Ser Gly Thr Ser
            20

<210> SEQ ID NO 106
<211> LENGTH: 10
<212> TYPE: PRT
<213> ORGANISM: Varicella zoster

<400> SEQUENCE: 106

Pro His Ser Val Val Asn Pro Phe Val Lys
1               5                   10

<210> SEQ ID NO 107
<211> LENGTH: 15
<212> TYPE: PRT
<213> ORGANISM: Varicella zoster

<400> SEQUENCE: 107

Arg Glu Glu Ser Pro Pro His Ser Val Val Asn Pro Phe Val Lys
1               5                   10                  15

<210> SEQ ID NO 108
<211> LENGTH: 9
<212> TYPE: PRT
<213> ORGANISM: Varicella zoster

<400> SEQUENCE: 108

Ser Leu Pro Arg Ser Arg Thr Pro Ile
1               5

<210> SEQ ID NO 109
<211> LENGTH: 19
<212> TYPE: PRT
<213> ORGANISM: Varicella zoster

<400> SEQUENCE: 109

Arg Gln Lys Ser Phe Ser Leu Pro Arg Ser Arg Thr Pro Ile Ile Pro
1               5                   10                  15

Pro Val Ser
```

-continued

```
<210> SEQ ID NO 110
<211> LENGTH: 9
<212> TYPE: PRT
<213> ORGANISM: Varicella zoster

<400> SEQUENCE: 110

Ser Ala Pro Leu Pro Ser Asn Arg Val
1               5

<210> SEQ ID NO 111
<211> LENGTH: 19
<212> TYPE: PRT
<213> ORGANISM: Varicella zoster

<400> SEQUENCE: 111

Ser Pro Trp Pro Gly Ser Ala Pro Leu Pro Ser Asn Arg Val Arg Phe
1               5                   10                  15

Gly Pro Ser

<210> SEQ ID NO 112
<211> LENGTH: 9
<212> TYPE: PRT
<213> ORGANISM: Varicella zoster

<400> SEQUENCE: 112

Ala Leu Trp Ala Leu Pro His Ala Ala
1               5

<210> SEQ ID NO 113
<211> LENGTH: 19
<212> TYPE: PRT
<213> ORGANISM: Varicella zoster

<400> SEQUENCE: 113

Met Ala Thr Gly Glu Ala Leu Trp Ala Leu Pro His Ala Ala Ala Ala
1               5                   10                  15

Val Ala Met

<210> SEQ ID NO 114
<211> LENGTH: 11
<212> TYPE: PRT
<213> ORGANISM: Varicella zoster

<400> SEQUENCE: 114

Pro Ile Arg His Asn Gly Ile Thr Met Glu Met
1               5                   10

<210> SEQ ID NO 115
<211> LENGTH: 9
<212> TYPE: PRT
<213> ORGANISM: human herpesvirus 1

<400> SEQUENCE: 115

Ser Leu Pro Ile Thr Val Tyr Tyr Ala
1               5

<210> SEQ ID NO 116
<211> LENGTH: 19
<212> TYPE: PRT
<213> ORGANISM: human herpesvirus 1

<400> SEQUENCE: 116

Pro Phe Gln Pro Pro Ser Leu Pro Ile Thr Val Tyr Tyr Ala Val Leu
1               5                   10                  15
```

-continued

Glu Arg Ala

<210> SEQ ID NO 117
<211> LENGTH: 9
<212> TYPE: PRT
<213> ORGANISM: human herpesvirus 1

<400> SEQUENCE: 117

Val Leu Leu Asn Ala Pro Ser Glu Ala
1               5

<210> SEQ ID NO 118
<211> LENGTH: 19
<212> TYPE: PRT
<213> ORGANISM: human herpesvirus 1

<400> SEQUENCE: 118

Arg Ala Cys Arg Ser Val Leu Leu Asn Ala Pro Ser Glu Ala Pro Gln
1               5                   10                  15

Ile Val Arg

<210> SEQ ID NO 119
<211> LENGTH: 9
<212> TYPE: PRT
<213> ORGANISM: human herpesvirus 1

<400> SEQUENCE: 119

Ala Leu Leu Glu Asp Pro Val Gly Thr
1               5

<210> SEQ ID NO 120
<211> LENGTH: 19
<212> TYPE: PRT
<213> ORGANISM: human herpesvirus 1

<400> SEQUENCE: 120

Asp Pro Glu Asp Ser Ala Leu Leu Glu Asp Pro Val Gly Thr Val Ala
1               5                   10                  15

Pro Gln Ile

<210> SEQ ID NO 121
<211> LENGTH: 10
<212> TYPE: PRT
<213> ORGANISM: human herpesvirus 2

<400> SEQUENCE: 121

Gly Phe Leu Ile Ala Tyr Gln Pro Leu Leu
1               5                   10

<210> SEQ ID NO 122
<211> LENGTH: 20
<212> TYPE: PRT
<213> ORGANISM: human herpesvirus 2

<400> SEQUENCE: 122

Tyr Leu Ala Thr Gly Gly Phe Leu Ile Ala Tyr Gln Pro Leu Leu Ser
1               5                   10                  15

Asn Thr Leu Ala
                20

<210> SEQ ID NO 123
<211> LENGTH: 9

<212> TYPE: PRT
<213> ORGANISM: human herpesvirus 2

<400> SEQUENCE: 123

Gly Leu Ala Asp Thr Val Val Ala Cys
1               5

<210> SEQ ID NO 124
<211> LENGTH: 19
<212> TYPE: PRT
<213> ORGANISM: human herpesvirus 2

<400> SEQUENCE: 124

Arg Leu His Pro His Ser Ala His Pro Ala Phe Ala Asp Val Glu Gln
1               5                   10                  15

Glu Ala Leu

<210> SEQ ID NO 125
<211> LENGTH: 12
<212> TYPE: PRT
<213> ORGANISM: Herpes simplex virus

<400> SEQUENCE: 125

Asp Arg Arg Asp Pro Leu Ala Arg Tyr Gly Ser Arg
1               5                   10

<210> SEQ ID NO 126
<211> LENGTH: 22
<212> TYPE: PRT
<213> ORGANISM: Herpes simplex virus

<400> SEQUENCE: 126

Gly Pro Val Trp Cys Asp Arg Arg Asp Pro Leu Ala Arg Tyr Gly Ser
1               5                   10                  15

Arg Val Gln Ile Arg Cys
            20

<210> SEQ ID NO 127
<211> LENGTH: 17
<212> TYPE: PRT
<213> ORGANISM: Epstein Barr Virus

<400> SEQUENCE: 127

Cys Ser Leu Glu Arg Glu Asp Arg Asp Ala Trp His Leu Pro Ala Tyr
1               5                   10                  15

Lys

<210> SEQ ID NO 128
<211> LENGTH: 21
<212> TYPE: PRT
<213> ORGANISM: Human poliovirus 3 strains P3/LEON/37 and PE/LEON/12A[1]B

<400> SEQUENCE: 128

Gln Pro Thr Thr Arg Ala Gln Lys Leu Phe Ala Met Trp Arg Ile Thr
1               5                   10                  15

Tyr Lys Asp Thr Val
            20

<210> SEQ ID NO 129
<211> LENGTH: 21
<212> TYPE: PRT
<213> ORGANISM: Human poliovirus type 3 strains P3/LEON/37 AND P3/LEON
      12A[1]B

<400> SEQUENCE: 129

Val Ala Ile Ile Glu Val Asp Asn Glu Gln Pro Thr Thr Arg Ala Gln
1 5 10 15

Lys Leu Phe Ala Met
20

<210> SEQ ID NO 130
<211> LENGTH: 20
<212> TYPE: PRT
<213> ORGANISM: Human poliovirus 1 Mahoney

<400> SEQUENCE: 130

Ser Ile Phe Tyr Thr Tyr Gly Thr Ala Pro Ala Arg Ile Ser Val Pro
1 5 10 15

Tyr Val Gly Ile
20

<210> SEQ ID NO 131
<211> LENGTH: 13
<212> TYPE: PRT
<213> ORGANISM: Mycobacterium tuberculosis

<400> SEQUENCE: 131

Glu Gln Gln Trp Asn Phe Ala Gly Ile Glu Ala Ala Ala
1 5 10

<210> SEQ ID NO 132
<211> LENGTH: 9
<212> TYPE: PRT
<213> ORGANISM: Mycobacterium bovis

<400> SEQUENCE: 132

Gly Leu Pro Val Glu Tyr Leu Gln Val
1 5

<210> SEQ ID NO 133
<211> LENGTH: 19
<212> TYPE: PRT
<213> ORGANISM: Mycobacterium bovis

<400> SEQUENCE: 133

Met Phe Ser Arg Pro Gly Leu Pro Val Glu Tyr Leu Gln Val Pro Ser
1 5 10 15

Ala Ser Met

<210> SEQ ID NO 134
<211> LENGTH: 16
<212> TYPE: PRT
<213> ORGANISM: Lyme borreliosis

<400> SEQUENCE: 134

Met Lys Lys Asp Asn Ile Ala Ala Met Val Leu Arg Gly Met Ala Lys
1 5 10 15

<210> SEQ ID NO 135
<211> LENGTH: 9
<212> TYPE: PRT
<213> ORGANISM: Chlamydia trachomatis

<400> SEQUENCE: 135

Arg Leu Asn Met Phe Thr Pro Tyr Ile
1 5

<210> SEQ ID NO 136
<211> LENGTH: 19
<212> TYPE: PRT
<213> ORGANISM: Chlamydia trachomatis

<400> SEQUENCE: 136

Leu Ala Leu Ser Tyr Arg Leu Asn Met Phe Thr Pro Tyr Ile Gly Val
1               5                   10                  15

Lys Trp Ser

<210> SEQ ID NO 137
<211> LENGTH: 9
<212> TYPE: PRT
<213> ORGANISM: Plasmodium malariae

<400> SEQUENCE: 137

Tyr Leu Asn Lys Ile Gln Asn Ser Leu
1               5

<210> SEQ ID NO 138
<211> LENGTH: 18
<212> TYPE: PRT
<213> ORGANISM: Plasmodium malariae

<400> SEQUENCE: 138

His Ile Lys Glu Tyr Leu Asn Lys Ile Gln Asn Ser Leu Ser Thr Glu
1               5                   10                  15

Trp Ser

<210> SEQ ID NO 139
<211> LENGTH: 20
<212> TYPE: PRT
<213> ORGANISM: Treponema pallidum

<400> SEQUENCE: 139

Ile Glu Ala Thr Leu His Cys Tyr Gly Ala Tyr Leu Thr Ile Gly Lys
1               5                   10                  15

Asn Pro Asp Phe
            20

<210> SEQ ID NO 140
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 140

Asp Leu Leu Lys Asn Gly Glu Arg Ile Glu Lys Val Glu Gly Gly Gly
1               5                   10                  15

Ser Met Gly Ala Leu Thr Asp Leu Gly Gln Asn Leu Leu Tyr Ala Asn
                20                  25                  30

Ser Ala His
        35

<210> SEQ ID NO 141
<211> LENGTH: 35
<212> TYPE: PRT
<213> ORGANISM: Artificial Sequence
<220> FEATURE:
<223> OTHER INFORMATION: Heteroconjugate construct

```
<400> SEQUENCE: 141

Asp Leu Leu Lys Asn Gly Glu Arg Ile Glu Lys Val Glu Gly Gly
1               5                   10                  15

Ala Arg Ala Thr Glu Thr Tyr Phe Ser Leu Asn Asn Lys Phe Arg Asn
            20                  25                  30

Pro Thr Val
        35

<210> SEQ ID NO 142
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 142

Asp Leu Leu Lys Asn Gly Glu Arg Ile Glu Lys Val Glu Gly Gly Gly
1               5                   10                  15

Thr Cys Gly Phe Ala Asp Leu Met Gly Tyr Ile Pro Ala Val Gly Ala
            20                  25                  30

Pro Leu Gly
        35

<210> SEQ ID NO 143
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 143

Asp Leu Leu Lys Asn Gly Glu Arg Ile Glu Lys Val Glu Gly Gly Gly
1               5                   10                  15

Leu Ala Pro Ile Thr Ala Tyr Ser Gln Gln Thr Arg Gly Leu Leu Gly
            20                  25                  30

Cys Ile Ile
        35

<210> SEQ ID NO 144
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 144

Asp Leu Leu Lys Asn Gly Glu Arg Ile Glu Lys Val Glu Gly Gly Gly
1               5                   10                  15

Leu Gln Ala Gly Phe Phe Leu Leu Thr Arg Ile Leu Thr Ile Pro Gln
            20                  25                  30

Ser Leu Asp
        35

<210> SEQ ID NO 145
<211> LENGTH: 32
<212> TYPE: PRT
<213> ORGANISM: Artificial Sequence
<220> FEATURE:
<223> OTHER INFORMATION: Heteroconjugate construct

<400> SEQUENCE: 145

Asp Leu Leu Lys Asn Gly Glu Arg Ile Glu Lys Val Glu Gly Gly Gly
```

```
                1               5                  10                  15
Leu Arg Gly Asp Leu Gln Val Leu Ala Gln Lys Val Ala Arg Thr Leu
            20                  25                  30

<210> SEQ ID NO 146
<211> LENGTH: 39
<212> TYPE: PRT
<213> ORGANISM: Artificial Sequence
<220> FEATURE:
<223> OTHER INFORMATION: Heteroconjugate construct

<400> SEQUENCE: 146

Asp Leu Leu Lys Asn Gly Glu Arg Ile Glu Lys Val Glu Gly Gly Gly
1               5                   10                  15

Asp Tyr Gln Gly Met Leu Pro Val Cys Pro Leu Ile Pro Gly Ser Ser
            20                  25                  30

Thr Thr Ser Thr Gly Pro Cys
        35

<210> SEQ ID NO 147
<211> LENGTH: 36
<212> TYPE: PRT
<213> ORGANISM: Artificial Sequence
<220> FEATURE:
<223> OTHER INFORMATION: Heteroconjugate construct

<400> SEQUENCE: 147

Asp Leu Leu Lys Asn Gly Glu Arg Ile Glu Lys Val Glu Gly Gly Gly
1               5                   10                  15

Pro Thr Leu His Glu Tyr Met Leu Asp Leu Gln Pro Glu Thr Thr Asp
            20                  25                  30

Leu Tyr Cys Tyr
        35

<210> SEQ ID NO 148
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 148

Asp Leu Leu Lys Asn Gly Glu Arg Ile Glu Lys Val Glu Gly Gly Gly
1               5                   10                  15

Gly Phe Gly Gln Ser Leu Leu Phe Gly Tyr Pro Val Tyr Val Phe Gly
            20                  25                  30

Asp Cys Val
        35

<210> SEQ ID NO 149
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 149

Asp Leu Leu Lys Asn Gly Glu Arg Ile Glu Lys Val Glu Gly Gly Gly
1               5                   10                  15

Arg Lys Ser Tyr Lys Lys Met Leu Lys Glu Met Gly Glu Val Ala Pro
            20                  25                  30

Glu Tyr Arg
```

-continued

```
<210> SEQ ID NO 150
<211> LENGTH: 34
<212> TYPE: PRT
<213> ORGANISM: Artificial Sequence
<220> FEATURE:
<223> OTHER INFORMATION: Heteroconjugate construct

<400> SEQUENCE: 150

Asp Leu Leu Lys Asn Gly Glu Arg Ile Glu Lys Val Glu Gly Gly Gly
1               5                   10                  15

Val Lys Val Asn Lys Val Asp Asp Thr Phe Tyr Tyr Val Ile Tyr Glu
            20                  25                  30

Ala Val

<210> SEQ ID NO 151
<211> LENGTH: 36
<212> TYPE: PRT
<213> ORGANISM: Artificial Sequence
<220> FEATURE:
<223> OTHER INFORMATION: Heteroconjugate construct

<400> SEQUENCE: 151

Asp Leu Leu Lys Asn Gly Glu Arg Ile Glu Lys Val Glu Gly Gly Gly
1               5                   10                  15

Glu Arg Val Asp Val Arg Leu Asp Asp Gly Asn Phe Gln Leu Met
            20                  25                  30

Asn Asp Pro Gly
        35

<210> SEQ ID NO 152
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 152

Asp Leu Leu Lys Asn Gly Glu Arg Ile Glu Lys Val Glu Gly Gly Gly
1               5                   10                  15

Lys Thr Gly Val Asp Ser Ile Thr Glu Val Glu Cys Phe Leu Thr Pro
            20                  25                  30

Glu Met Gly
        35

<210> SEQ ID NO 153
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 153

Asp Leu Leu Lys Asn Gly Glu Arg Ile Glu Lys Val Glu Gly Gly Gly
1               5                   10                  15

Leu Thr Cys Gly Asn Leu Leu Met Trp Glu Ala Val Thr Val Lys Thr
            20                  25                  30

Glu Val Leu
        35

<210> SEQ ID NO 154
```

<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 154

Asp Leu Leu Lys Asn Gly Glu Arg Ile Glu Lys Val Glu Gly Gly Gly
1               5                   10                  15

Gly Met Thr Leu Leu Leu Leu Ile Trp Phe Arg Pro Val Ala Asp
            20                  25                  30

Phe Ala Thr
        35

<210> SEQ ID NO 155
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 155

Asp Leu Leu Lys Asn Gly Glu Arg Ile Glu Lys Val Glu Gly Gly Gly
1               5                   10                  15

Gly Phe Gly Gln Ser Leu Leu Tyr Gly Tyr Pro Val Tyr Val Phe Gly
            20                  25                  30

Asp Cys Val
        35

<210> SEQ ID NO 156
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 156

Asp Leu Leu Lys Asn Gly Glu Arg Ile Glu Lys Val Glu Gly Gly Gly
1               5                   10                  15

Asn Pro Glu Lys Asp Val Leu Ala Glu Leu Val Lys Gln Ile Lys Val
            20                  25                  30

Arg Val Asp
        35

<210> SEQ ID NO 157
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 157

Asp Leu Leu Lys Asn Gly Glu Arg Ile Glu Lys Val Glu Gly Gly Gly
1               5                   10                  15

Thr Val Glu Leu Arg Gln Tyr Asp Pro Val Ala Ala Leu Phe Phe Phe
            20                  25                  30

Asp Ile Asp
        35

<210> SEQ ID NO 158
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 158

Asp Leu Leu Lys Asn Gly Glu Arg Ile Glu Lys Val Glu Gly Gly Gly
1               5                   10                  15

Leu Leu Ala Arg Leu Phe Leu Tyr Ala Leu Ala Leu Leu Leu Ala
            20                  25                  30

Ser Ala Leu
        35

<210> SEQ ID NO 159
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 159

Asp Leu Leu Lys Asn Gly Glu Arg Ile Glu Lys Val Glu Gly Gly Gly
1               5                   10                  15

Pro Val Ile Val Ala Pro Tyr Leu Phe Trp Leu Ala Ala Ile Ala Ala
            20                  25                  30

Ser Cys Phe
        35

<210> SEQ ID NO 160
<211> LENGTH: 36
<212> TYPE: PRT
<213> ORGANISM: Artificial Sequence
<220> FEATURE:
<223> OTHER INFORMATION: Heteroconjugate construct

<400> SEQUENCE: 160

Asp Leu Leu Lys Asn Gly Glu Arg Ile Glu Lys Val Glu Gly Gly Gly
1               5                   10                  15

Val His Val Pro Asp Val Leu Leu Asn Gly Trp Arg Trp Arg Leu Gly
            20                  25                  30

Ala Ile Pro Pro
        35

<210> SEQ ID NO 161
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 161

Asp Leu Leu Lys Asn Gly Glu Arg Ile Glu Lys Val Glu Gly Gly Gly
1               5                   10                  15

Val Glu Gln Ser Gly His Arg Gln Ser Ile Trp Ile Thr Trp His Thr
            20                  25                  30

Gln Pro Val
        35

<210> SEQ ID NO 162
<211> LENGTH: 31
<212> TYPE: PRT
<213> ORGANISM: Artificial Sequence
<220> FEATURE:
<223> OTHER INFORMATION: Heteroconjugate construct

```
<400> SEQUENCE: 162

Asp Leu Leu Lys Asn Gly Glu Arg Ile Glu Lys Val Glu Gly Gly Gly
1               5                   10                  15

Leu Val Cys Leu Leu Ala Ile Ser Val Val Pro Ser Gly Gln
            20                  25                  30

<210> SEQ ID NO 163
<211> LENGTH: 31
<212> TYPE: PRT
<213> ORGANISM: Artificial Sequence
<220> FEATURE:
<223> OTHER INFORMATION: Heteroconjugate construct

<400> SEQUENCE: 163

Asp Leu Leu Lys Asn Gly Glu Arg Ile Glu Lys Val Glu Gly Gly Gly
1               5                   10                  15

Glu Leu Thr Asp Ala Leu Ile Ser Ala Phe Ser Gly Ser Tyr Ser
            20                  25                  30

<210> SEQ ID NO 164
<211> LENGTH: 31
<212> TYPE: PRT
<213> ORGANISM: Artificial Sequence
<220> FEATURE:
<223> OTHER INFORMATION: Heteroconjugate construct

<400> SEQUENCE: 164

Asp Leu Leu Lys Asn Gly Glu Arg Ile Glu Lys Val Glu Gly Gly Gly
1               5                   10                  15

Leu Ile Leu Tyr Leu Cys Val Pro Arg Cys Arg Arg Lys Lys Pro
            20                  25                  30

<210> SEQ ID NO 165
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 165

Asp Leu Leu Lys Asn Gly Glu Arg Ile Glu Lys Val Glu Gly Gly Gly
1               5                   10                  15

Gln Ser Arg Arg Ser Ile Ser Ala Arg Gly Gln Glu Leu Phe Arg Thr
            20                  25                  30

Leu Leu Glu
        35

<210> SEQ ID NO 166
<211> LENGTH: 37
<212> TYPE: PRT
<213> ORGANISM: Artificial Sequence
<220> FEATURE:
<223> OTHER INFORMATION: Heteroconjugate construct

<400> SEQUENCE: 166

Asp Leu Leu Lys Asn Gly Glu Arg Ile Glu Lys Val Glu Gly Gly Gly
1               5                   10                  15

Pro Ile Pro Val Ser Glu Ile Thr Asp Thr Ile Asp Lys Phe Gly Lys
            20                  25                  30

Cys Ser Ser Lys Ala
        35
```

```
<210> SEQ ID NO 167
<211> LENGTH: 37
<212> TYPE: PRT
<213> ORGANISM: Artificial Sequence
<220> FEATURE:
<223> OTHER INFORMATION: Heteroconjugate construct

<400> SEQUENCE: 167

Asp Leu Leu Lys Asn Gly Glu Arg Ile Glu Lys Val Glu Gly Gly Gly
1               5                   10                  15

Lys Gly Leu Lys Gln Leu Pro Glu Gly Met Asp Pro Phe Ala Glu Lys
            20                  25                  30

Pro Asn Ala Thr Asp
        35

<210> SEQ ID NO 168
<211> LENGTH: 37
<212> TYPE: PRT
<213> ORGANISM: Artificial Sequence
<220> FEATURE:
<223> OTHER INFORMATION: Heteroconjugate construct

<400> SEQUENCE: 168

Asp Leu Leu Lys Asn Gly Glu Arg Ile Glu Lys Val Glu Gly Gly Gly
1               5                   10                  15

Ala Leu Phe Gln Gln Ala Arg Leu Cys Asp Leu Pro Ala Thr Pro Lys
            20                  25                  30

Gly Ser Gly Thr Ser
        35

<210> SEQ ID NO 169
<211> LENGTH: 31
<212> TYPE: PRT
<213> ORGANISM: Artificial Sequence
<220> FEATURE:
<223> OTHER INFORMATION: Heteroconjugate construct

<400> SEQUENCE: 169

Asp Leu Leu Lys Asn Gly Glu Arg Ile Glu Lys Val Glu Gly Gly Gly
1               5                   10                  15

Arg Glu Glu Ser Pro Pro His Ser Val Val Asn Pro Phe Val Lys
            20                  25                  30

<210> SEQ ID NO 170
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 170

Asp Leu Leu Lys Asn Gly Glu Arg Ile Glu Lys Val Glu Gly Gly Gly
1               5                   10                  15

Arg Gln Lys Ser Phe Ser Leu Pro Arg Ser Arg Thr Pro Ile Ile Pro
            20                  25                  30

Pro Val Ser
        35

<210> SEQ ID NO 171
<211> LENGTH: 35
<212> TYPE: PRT
<213> ORGANISM: Artificial Sequence
<220> FEATURE:
<223> OTHER INFORMATION: Heteroconjugate construct
```

<400> SEQUENCE: 171

Asp Leu Leu Lys Asn Gly Glu Arg Ile Glu Lys Val Glu Gly Gly Gly
1               5                   10                  15

Ser Pro Trp Pro Gly Ser Ala Pro Leu Pro Ser Asn Arg Val Arg Phe
            20                  25                  30

Gly Pro Ser
        35

<210> SEQ ID NO 172
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 172

Asp Leu Leu Lys Asn Gly Glu Arg Ile Glu Lys Val Glu Gly Gly Gly
1               5                   10                  15

Met Ala Thr Gly Glu Ala Leu Trp Ala Leu Pro His Ala Ala Ala Ala
            20                  25                  30

Val Ala Met
        35

<210> SEQ ID NO 173
<211> LENGTH: 27
<212> TYPE: PRT
<213> ORGANISM: Artificial Sequence
<220> FEATURE:
<223> OTHER INFORMATION: Heteroconjugate construct

<400> SEQUENCE: 173

Asp Leu Leu Lys Asn Gly Glu Arg Ile Glu Lys Val Glu Gly Gly Gly
1               5                   10                  15

Pro Ile Arg His Asn Gly Ile Thr Met Glu Met
            20                  25

<210> SEQ ID NO 174
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 174

Asp Leu Leu Lys Asn Gly Glu Arg Ile Glu Lys Val Glu Gly Gly Gly
1               5                   10                  15

Pro Phe Gln Pro Pro Ser Leu Pro Ile Thr Val Tyr Tyr Ala Val Leu
            20                  25                  30

Glu Arg Ala
        35

<210> SEQ ID NO 175
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 175

Asp Leu Leu Lys Asn Gly Glu Arg Ile Glu Lys Val Glu Gly Gly Gly
1               5                   10                  15

```
Arg Ala Cys Arg Ser Val Leu Leu Asn Ala Pro Ser Glu Ala Pro Gln
            20                  25                  30

Ile Val Arg
        35

<210> SEQ ID NO 176
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 176

Asp Leu Leu Lys Asn Gly Glu Arg Ile Glu Lys Val Glu Gly Gly Gly
1               5                   10                  15

Asp Pro Glu Asp Ser Ala Leu Leu Glu Asp Pro Val Gly Thr Val Ala
            20                  25                  30

Pro Gln Ile
        35

<210> SEQ ID NO 177
<211> LENGTH: 36
<212> TYPE: PRT
<213> ORGANISM: Artificial Sequence
<220> FEATURE:
<223> OTHER INFORMATION: Heteroconjugate construct

<400> SEQUENCE: 177

Asp Leu Leu Lys Asn Gly Glu Arg Ile Glu Lys Val Glu Gly Gly Gly
1               5                   10                  15

Tyr Leu Ala Thr Gly Gly Phe Leu Ile Ala Tyr Gln Pro Leu Leu Ser
            20                  25                  30

Asn Thr Leu Ala
        35

<210> SEQ ID NO 178
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 178

Asp Leu Leu Lys Asn Gly Glu Arg Ile Glu Lys Val Glu Gly Gly Gly
1               5                   10                  15

Arg Leu His Pro His Ser Ala His Pro Ala Phe Ala Asp Val Glu Gln
            20                  25                  30

Glu Ala Leu
        35

<210> SEQ ID NO 179
<211> LENGTH: 38
<212> TYPE: PRT
<213> ORGANISM: Artificial Sequence
<220> FEATURE:
<223> OTHER INFORMATION: Heteroconjugate construct

<400> SEQUENCE: 179

Asp Leu Leu Lys Asn Gly Glu Arg Ile Glu Lys Val Glu Gly Gly Gly
1               5                   10                  15

Gly Pro Val Trp Cys Asp Arg Arg Asp Pro Leu Ala Arg Tyr Gly Ser
            20                  25                  30
```

Arg Val Gln Ile Arg Cys
        35

<210> SEQ ID NO 180
<211> LENGTH: 33
<212> TYPE: PRT
<213> ORGANISM: Artificial Sequence
<220> FEATURE:
<223> OTHER INFORMATION: Heteroconjugate construct

<400> SEQUENCE: 180

Asp Leu Leu Lys Asn Gly Glu Arg Ile Glu Lys Val Glu Gly Gly Gly
1               5                   10                  15

Cys Ser Leu Glu Arg Glu Asp Arg Asp Ala Trp His Leu Pro Ala Tyr
            20                  25                  30

Lys

<210> SEQ ID NO 181
<211> LENGTH: 37
<212> TYPE: PRT
<213> ORGANISM: Artificial Sequence
<220> FEATURE:
<223> OTHER INFORMATION: Heteroconjugate construct

<400> SEQUENCE: 181

Asp Leu Leu Lys Asn Gly Glu Arg Ile Glu Lys Val Glu Gly Gly Gly
1               5                   10                  15

Gln Pro Thr Thr Arg Ala Gln Lys Leu Phe Ala Met Trp Arg Ile Thr
            20                  25                  30

Tyr Lys Asp Thr Val
        35

<210> SEQ ID NO 182
<211> LENGTH: 37
<212> TYPE: PRT
<213> ORGANISM: Artificial Sequence
<220> FEATURE:
<223> OTHER INFORMATION: Heteroconjugate construct

<400> SEQUENCE: 182

Asp Leu Leu Lys Asn Gly Glu Arg Ile Glu Lys Val Glu Gly Gly Gly
1               5                   10                  15

Val Ala Ile Ile Glu Val Asp Asn Glu Gln Pro Thr Thr Arg Ala Gln
            20                  25                  30

Lys Leu Phe Ala Met
        35

<210> SEQ ID NO 183
<211> LENGTH: 36
<212> TYPE: PRT
<213> ORGANISM: Artificial Sequence
<220> FEATURE:
<223> OTHER INFORMATION: Heteroconjugate construct

<400> SEQUENCE: 183

Asp Leu Leu Lys Asn Gly Glu Arg Ile Glu Lys Val Glu Gly Gly Gly
1               5                   10                  15

Ser Ile Phe Tyr Thr Tyr Gly Thr Ala Pro Ala Arg Ile Ser Val Pro
            20                  25                  30

Tyr Val Gly Ile
        35

```
<210> SEQ ID NO 184
<211> LENGTH: 29
<212> TYPE: PRT
<213> ORGANISM: Artificial Sequence
<220> FEATURE:
<223> OTHER INFORMATION: Heteroconjugate construct

<400> SEQUENCE: 184

Asp Leu Leu Lys Asn Gly Glu Arg Ile Glu Lys Val Glu Gly Gly Gly
1               5                   10                  15

Glu Gln Gln Trp Asn Phe Ala Gly Ile Glu Ala Ala Ala
            20                  25

<210> SEQ ID NO 185
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 185

Asp Leu Leu Lys Asn Gly Glu Arg Ile Glu Lys Val Glu Gly Gly Gly
1               5                   10                  15

Met Phe Ser Arg Pro Gly Leu Pro Val Glu Tyr Leu Gln Val Pro Ser
            20                  25                  30

Ala Ser Met
        35

<210> SEQ ID NO 186
<211> LENGTH: 32
<212> TYPE: PRT
<213> ORGANISM: Artificial Sequence
<220> FEATURE:
<223> OTHER INFORMATION: Heteroconjugate construct

<400> SEQUENCE: 186

Asp Leu Leu Lys Asn Gly Glu Arg Ile Glu Lys Val Glu Gly Gly Gly
1               5                   10                  15

Met Lys Lys Asp Asn Ile Ala Ala Met Val Leu Arg Gly Met Ala Lys
            20                  25                  30

<210> SEQ ID NO 187
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 187

Asp Leu Leu Lys Asn Gly Glu Arg Ile Glu Lys Val Glu Gly Gly Gly
1               5                   10                  15

Leu Ala Leu Ser Tyr Arg Leu Asn Met Phe Thr Pro Tyr Ile Gly Val
            20                  25                  30

Lys Trp Ser
        35

<210> SEQ ID NO 188
<211> LENGTH: 34
<212> TYPE: PRT
<213> ORGANISM: Artificial Sequence
<220> FEATURE:
<223> OTHER INFORMATION: Heteroconjugate construct

<400> SEQUENCE: 188
```

-continued

Asp Leu Leu Lys Asn Gly Glu Arg Ile Glu Lys Val Glu Gly Gly Gly
1               5                   10                  15

His

```
<212> TYPE: PRT
<213> ORGANISM: Lyme borreliosis

<400> SEQUENCE: 194

Lys Ser Tyr Val Leu Glu Gly Thr Leu Thr Ala Glu
1               5                   10

<210> SEQ ID NO 195
<211> LENGTH: 30
<212> TYPE: PRT
<213> ORGANISM: Lyme borreliosis

<400> SEQUENCE: 195

Gly Ser Gly Lys Ala Lys Glu Val Leu Lys Ser Tyr Val Leu Glu Gly
1               5                   10                  15

Thr Leu Thr Ala Glu Lys Thr Thr Leu Val Val Lys Glu Gly
            20                  25                  30

<210> SEQ ID NO 196
<211> LENGTH: 9
<212> TYPE: PRT
<213> ORGANISM: Human immunodeficiency virus type 1

<400> SEQUENCE: 196

Lys Leu Thr Pro Leu Cys Val Thr Leu
1               5

<210> SEQ ID NO 197
<211> LENGTH: 19
<212> TYPE: PRT
<213> ORGANISM: Human immunodeficiency virus type 1

<400> SEQUENCE: 197

Leu Lys Pro Cys Val Lys Leu Thr Pro Leu Cys Val Thr Leu Asn Cys
1               5                   10                  15

Ser Asn Ile

<210> SEQ ID NO 198
<211> LENGTH: 8
<212> TYPE: PRT
<213> ORGANISM: Human immunodeficiency virus type 1

<400> SEQUENCE: 198

Glu Ile Tyr Lys Arg Trp Ile Ile
1               5

<210> SEQ ID NO 199
<211> LENGTH: 18
<212> TYPE: PRT
<213> ORGANISM: Human immunodeficiency virus type 1

<400> SEQUENCE: 199

Pro Ile Pro Val Gly Glu Ile Tyr Lys Arg Trp Ile Ile Leu Gly Leu
1               5                   10                  15

Asn Lys

<210> SEQ ID NO 200
<211> LENGTH: 10
<212> TYPE: PRT
<213> ORGANISM: Human immunodeficiency virus type 1

<400> SEQUENCE: 200

Leu Tyr Pro Leu Ala Ser Leu Arg Ser Leu
```

<210> SEQ ID NO 201
<211> LENGTH: 30
<212> TYPE: PRT
<213> ORGANISM: Human immunodeficiency virus type 1

<400> SEQUENCE: 201

Thr Pro Ser Gln Lys Gln Glu Pro Ile Asp Lys Glu Leu Tyr Pro Leu
1               5                   10                  15
Ala Ser Leu Arg Ser Leu Phe Gly Ser Asp Pro Ser Ser Gln
            20                  25                  30

<210> SEQ ID NO 202
<211> LENGTH: 15
<212> TYPE: PRT
<213> ORGANISM: Human immunodeficiency virus type 1

<400> SEQUENCE: 202

Ser Leu Tyr Asn Thr Val Ala Thr Leu Tyr Cys Val His Gln Arg
1               5                   10                  15

<210> SEQ ID NO 203
<211> LENGTH: 9
<212> TYPE: PRT
<213> ORGANISM: Human immunodeficiency virus type 1

<400> SEQUENCE: 203

Lys Leu Val Gly Lys Leu Asn Trp Ala
1               5

<210> SEQ ID NO 204
<211> LENGTH: 19
<212> TYPE: PRT
<213> ORGANISM: Human immunodeficiency virus type 1

<400> SEQUENCE: 204

Val Asn Asp Ile Gln Lys Leu Val Gly Lys Leu Asn Trp Ala Ser Gln
1               5                   10                  15
Ile Tyr Ala

<210> SEQ ID NO 205
<211> LENGTH: 9
<212> TYPE: PRT
<213> ORGANISM: Helicobacter pylori

<400> SEQUENCE: 205

Gly Tyr Asn Lys Ala Met Gly Phe Leu
1               5

<210> SEQ ID NO 206
<211> LENGTH: 19
<212> TYPE: PRT
<213> ORGANISM: Helicobacter pylori

<400> SEQUENCE: 206

Asn Ser Tyr Pro Asn Gly Tyr Asn Lys Ala Met Gly Phe Leu Lys Val
1               5                   10                  15
Phe Lys His

<210> SEQ ID NO 207
<211> LENGTH: 9
<212> TYPE: PRT

<213> ORGANISM: Helicobacter pylori

<400> SEQUENCE: 207

Ile Tyr Val Lys Thr Ser Ser Phe Leu
1               5

<210> SEQ ID NO 208
<211> LENGTH: 19
<212> TYPE: PRT
<213> ORGANISM: Helicobacter pylori

<400> SEQUENCE: 208

Glu Ile Asp His Lys Ile Tyr Val Lys Thr Ser Ser Phe Leu Asp Phe
1               5                   10                  15

Cys Arg Asn

<210> SEQ ID NO 209
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 209

Asp Leu Leu Lys Asn Gly Glu Arg Ile Glu Lys Val Glu Gly Gly Gly
1               5                   10                  15

Thr Gln Gln Ile Pro Lys Leu Val Ala Asn Asn Thr Arg Leu Trp Val
            20                  25                  30

Tyr Cys Gly
        35

<210> SEQ ID NO 210
<211> LENGTH: 36
<212> TYPE: PRT
<213> ORGANISM: Artificial Sequence
<220> FEATURE:
<223> OTHER INFORMATION: Heteroconjugate construct

<400> SEQUENCE: 210

Asp Leu Leu Lys Asn Gly Glu Arg Ile Glu Lys Val Glu Gly Gly Gly
1               5                   10                  15

Thr Gly Ile Ala Ala Val Leu Thr Asp Gly Asn Pro Pro Glu Val Lys
            20                  25                  30

Ser Val Gly Leu
        35

<210> SEQ ID NO 211
<211> LENGTH: 46
<212> TYPE: PRT
<213> ORGANISM: Artificial Sequence
<220> FEATURE:
<223> OTHER INFORMATION: Heteroconjugate construct

<400> SEQUENCE: 211

Asp Leu Leu Lys Asn Gly Glu Arg Ile Glu Lys Val Glu Gly Gly Gly
1               5                   10                  15

Gly Ser Gly Lys Ala Lys Glu Val Leu Lys Ser Tyr Val Leu Glu Gly
            20                  25                  30

Thr Leu Thr Ala Glu Lys Thr Thr Leu Val Val Lys Glu Gly
        35                  40                  45

<210> SEQ ID NO 212

```
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 212

Asp Leu Leu Lys Asn Gly Glu Arg Ile Glu Lys Val Glu Gly Gly Gly
1               5                   10                  15

Leu Lys Pro Cys Val Lys Leu Thr Pro Leu Cys Val Thr Leu Asn Cys
            20                  25                  30

Ser Asn Ile
        35

<210> SEQ ID NO 213
<211> LENGTH: 34
<212> TYPE: PRT
<213> ORGANISM: Artificial Sequence
<220> FEATURE:
<223> OTHER INFORMATION: Heteroconjugate construct

<400> SEQUENCE: 213

Asp Leu Leu Lys Asn Gly Glu Arg Ile Glu Lys Val Glu Gly Gly Gly
1               5                   10                  15

Pro Ile Pro Val Gly Glu Ile Tyr Lys Arg Trp Ile Ile Leu Gly Leu
            20                  25                  30

Asn Lys

<210> SEQ ID NO 214
<211> LENGTH: 46
<212> TYPE: PRT
<213> ORGANISM: Artificial Sequence
<220> FEATURE:
<223> OTHER INFORMATION: Heteroconjugate construct

<400> SEQUENCE: 214

Asp Leu Leu Lys Asn Gly Glu Arg Ile Glu Lys Val Glu Gly Gly Gly
1               5                   10                  15

Thr Pro Ser Gln Lys Gln Glu Pro Ile Asp Lys Glu Leu Tyr Pro Leu
            20                  25                  30

Ala Ser Leu Arg Ser Leu Phe Gly Ser Asp Pro Ser Ser Gln
        35                  40                  45

<210> SEQ ID NO 215
<211> LENGTH: 31
<212> TYPE: PRT
<213> ORGANISM: Artificial Sequence
<220> FEATURE:
<223> OTHER INFORMATION: Heteroconjugate construct

<400> SEQUENCE: 215

Asp Leu Leu Lys Asn Gly Glu Arg Ile Glu Lys Val Glu Gly Gly Gly
1               5                   10                  15

Ser Leu Tyr Asn Thr Val Ala Thr Leu Tyr Cys Val His Gln Arg
            20                  25                  30

<210> SEQ ID NO 216
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 216
```

```
Asp Leu Leu Lys Asn Gly Glu Arg Ile Glu Lys Val Glu Gly Gly Gly
1               5                   10                  15

Val Asn Asp Ile Gln Lys Leu Val Gly Lys Leu Asn Trp Ala Ser Gln
            20                  25                  30

Ile Tyr Ala
        35

<210> SEQ ID NO 217
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 217

Asp Leu Leu Lys Asn Gly Glu Arg Ile Glu Lys Val Glu Gly Gly Gly
1               5                   10                  15

Asn Ser Tyr Pro Asn Gly Tyr Asn Lys Ala Met Gly Phe Leu Lys Val
            20                  25                  30

Phe Lys His
        35

<210> SEQ ID NO 218
<211> LENGTH: 35
<212> TYPE: PRT
<213> ORGANISM: Artificial Sequence
<220> FEATURE:
<223> OTHER INFORMATION: Heteroconjugate construct

<400> SEQUENCE: 218

Asp Leu Leu Lys Asn Gly Glu Arg Ile Glu Lys Val Glu Gly Gly Gly
1               5                   10                  15

Glu Ile Asp His Lys Ile Tyr Val Lys Thr Ser Ser Phe Leu Asp Phe
            20                  25                  30

Cys Arg Asn
        35

<210> SEQ ID NO 219
<211> LENGTH: 16
<212> TYPE: PRT
<213> ORGANISM: human herpesvirus 1

<400> SEQUENCE: 219

Ser Leu Lys Met Ala Asp Pro Asn Arg Phe Arg Gly Lys Asp Leu Pro
1               5                   10                  15

<210> SEQ ID NO 220
<211> LENGTH: 32
<212> TYPE: PRT
<213> ORGANISM: Artificial Sequence
<220> FEATURE:
<223> OTHER INFORMATION: Heteroconjugate construct

<400> SEQUENCE: 220

Asp Leu Leu Lys Asn Gly Glu Arg Ile Glu Lys Val Glu Gly Gly Gly
1               5                   10                  15

Ser Leu Lys Met Ala Asp Pro Asn Arg Phe Arg Gly Lys Asp Leu Pro
            20                  25                  30

<210> SEQ ID NO 221
<211> LENGTH: 36
<212> TYPE: PRT
```

<213> ORGANISM: Artificial Sequence
<220> FEATURE:
<223> OTHER INFORMATION: Heteroconjugate construct

<400> SEQUENCE: 221

Asp Leu Leu Lys Asn Gly Glu Arg Ile Glu Lys Val Glu Gly Gly
1               5                   10                  15

Thr Gly Gly Lys Pro Gly Ile Ala Gly Phe Lys Gly Glu Gln Gly Pro
            20                  25                  30

Lys Gly Glu Pro
        35

<210> SEQ ID NO 222
<211> LENGTH: 36
<212> TYPE: PRT
<213> ORGANISM: Artificial Sequence
<220> FEATURE:
<223> OTHER INFORMATION: Heteroconjugate construct

<400> SEQUENCE: 222

Asp Leu Leu Lys Asn Gly Glu Arg Ile Glu Lys Val Glu Gly Gly Gly
1               5                   10                  15

Asp Ala Gly Glu Pro Gly Ile Ala Gly Phe Lys Gly Asp Gln Gly Pro
            20                  25                  30

Lys Gly Glu Thr
        35

<210> SEQ ID NO 223
<211> LENGTH: 20
<212> TYPE: PRT
<213> ORGANISM: Homo sapiens

<400> SEQUENCE: 223

Thr Gly Gly Lys Pro Gly Ile Ala Gly Phe Lys Gly Glu Gln Gly Pro
1               5                   10                  15

Lys Gly Glu Pro
            20

<210> SEQ ID NO 224
<211> LENGTH: 20
<212> TYPE: PRT
<213> ORGANISM: Mus musculus

<400> SEQUENCE: 224

Asp Ala Gly Glu Pro Gly Ile Ala Gly Phe Lys Gly Asp Gln Gly Pro
1               5                   10                  15

Lys Gly Glu Thr
            20

<210> SEQ ID NO 225
<211> LENGTH: 13
<212> TYPE: PRT
<213> ORGANISM: Artificial Sequence
<220> FEATURE:
<223> OTHER INFORMATION: Artificial variable sequence
<220> FEATURE:
<221> NAME/KEY: MISC_FEATURE
<222> LOCATION: (1)..(1)
<223> OTHER INFORMATION: X is Asp or Glu
<220> FEATURE:
<221> NAME/KEY: MISC_FEATURE
<222> LOCATION: (2)..(3)
<223> OTHER INFORMATION: X is Ile, Leu or Val
<220> FEATURE:
<221> NAME/KEY: MISC_FEATURE

```
<222> LOCATION: (4)..(4)
<223> OTHER INFORMATION: X is Lys, Arg or His
<220> FEATURE:
<221> NAME/KEY: MISC_FEATURE
<222> LOCATION: (5)..(5)
<223> OTHER INFORMATION: X is Asn or Gln
<220> FEATURE:
<221> NAME/KEY: MISC_FEATURE
<222> LOCATION: (5)..(5)
<223> OTHER INFORMATION: X is Asn or Gln
<220> FEATURE:
<221> NAME/KEY: MISC_FEATURE
<222> LOCATION: (6)..(6)
<223> OTHER INFORMATION: X is Gly or Ala
<220> FEATURE:
<221> NAME/KEY: MISC_FEATURE
<222> LOCATION: (7)..(7)
<223> OTHER INFORMATION: X is Asp or Glu
<220> FEATURE:
<221> NAME/KEY: MISC_FEATURE
<222> LOCATION: (8)..(8)
<223> OTHER INFORMATION: X is Lys, Arg or His
<220> FEATURE:
<221> NAME/KEY: MISC_FEATURE
<222> LOCATION: (9)..(9)
<223> OTHER INFORMATION: X is Ile, Leu or Val
<220> FEATURE:
<221> NAME/KEY: MISC_FEATURE
<222> LOCATION: (10)..(10)
<223> OTHER INFORMATION: X is Asp or Glu
<220> FEATURE:
<221> NAME/KEY: MISC_FEATURE
<222> LOCATION: (11)..(11)
<223> OTHER INFORMATION: X is Lys, Arg or His
<220> FEATURE:
<221> NAME/KEY: MISC_FEATURE
<222> LOCATION: (12)..(12)
<223> OTHER INFORMATION: X is Ile, Leu or Val
<220> FEATURE:
<221> NAME/KEY: MISC_FEATURE
<222> LOCATION: (13)..(13)
<223> OTHER INFORMATION: X is Asp or Glu

<400> SEQUENCE: 225

Xaa Xaa Xaa Xaa Xaa Xaa Xaa Xaa Xaa Xaa Xaa Xaa Xaa
1               5                   10

<210> SEQ ID NO 226
<211> LENGTH: 15
<212> TYPE: PRT
<213> ORGANISM: Artificial Sequence
<220> FEATURE:
<223> OTHER INFORMATION: Artificial variable sequence
<220> FEATURE:
<221> NAME/KEY: MISC_FEATURE
<222> LOCATION: (1)..(1)
<223> OTHER INFORMATION: X is Asn or Gln
<220> FEATURE:
<221> NAME/KEY: MISC_FEATURE
<222> LOCATION: (2)..(2)
<223> OTHER INFORMATION: X is Asp or Glu
<220> FEATURE:
<221> NAME/KEY: MISC_FEATURE
<222> LOCATION: (3)..(3)
<223> OTHER INFORMATION: X is Ala or Gly
<220> FEATURE:
<221> NAME/KEY: MISC_FEATURE
<222> LOCATION: (4)..(4)
<223> OTHER INFORMATION: X is Thr or Ser
<220> FEATURE:
<221> NAME/KEY: MISC_FEATURE
<222> LOCATION: (5)..(5)
<223> OTHER INFORMATION: X is Phe, Arg or Tyr
<220> FEATURE:
<221> NAME/KEY: MISC_FEATURE
<222> LOCATION: (6)..(6)
<223> OTHER INFORMATION: X is Asn or Gln
```

```
<220> FEATURE:
<221> NAME/KEY: MISC_FEATURE
<222> LOCATION: (7)..(7)
<223> OTHER INFORMATION: X is Lys, Arg or His
<220> FEATURE:
<221> NAME/KEY: MISC_FEATURE
<222> LOCATION: (8)..(8)
<223> OTHER INFORMATION: X is Tyr or Arg
<220> FEATURE:
<221> NAME/KEY: MISC_FEATURE
<222> LOCATION: (9)..(9)
<223> OTHER INFORMATION: X is Lys, Arg or His
<220> FEATURE:
<221> NAME/KEY: MISC_FEATURE
<222> LOCATION: (10)..(10)
<223> OTHER INFORMATION: X is Ala or Gly
<220> FEATURE:
<221> NAME/KEY: MISC_FEATURE
<222> LOCATION: (11)..(12)
<223> OTHER INFORMATION: X is Ile, Leu or Val
<220> FEATURE:
<221> NAME/KEY: MISC_FEATURE
<222> LOCATION: (13)..(13)
<223> OTHER INFORMATION: X is Lys, Arg or His
<220> FEATURE:
<221> NAME/KEY: MISC_FEATURE
<222> LOCATION: (14)..(14)
<223> OTHER INFORMATION: X is Thr or Ser
<220> FEATURE:
<221> NAME/KEY: MISC_FEATURE
<222> LOCATION: (15)..(15)
<223> OTHER INFORMATION: X is Ala or Gly

<400> SEQUENCE: 226

Xaa Xaa Xaa Xaa Xaa Xaa Xaa Xaa Xaa Xaa Xaa Xaa Xaa Xaa Xaa
1               5                   10                  15
```

METHOD FOR INDUCING AN IMMUNE RESPONSE AND FORMULATIONS THEREOF

SEQUENCE LISTING

This application contains a "Sequence Listing" submitted as an electronic .txt file named "CS_ST25.txt." The subject matter of the "Sequence Listing" is incorporated herein by reference along with the subject matter of International Publication Number WO 2010/120897 A1 (International Application Number PCT/US2010/031054) and U.S. Patent Application 61/490,050, 61/538,427 and 61/490,056.

FIELD OF INVENTION

The invention generally relates to methods for preventing or treating a disease by generating or modulating an immune response with the use of specific peptide constructs. In one embodiment, an immunomodulatory Peptide J, DLLKNGE-RIEKVE (SEQ ID No. 3), is part of a peptide construct to induce an antigen-specific maturation of immune cells from a mammal subject. The immunomodulator Peptide J can be linked to antigen epitopes of infectious diseases such as Type A influenza viruses (H1N1, H5N1, H3N2, etc.), including influenza viruses that originate in "swine," "avian" or "bird" species, to provide for a method of treatment or prevention of influenza viral diseases. In other embodiments, for example, the immunomodulator Peptide J can be linked to antigen epitopes of infectious diseases such as Type such as Herpes simplex virus or other RNA or DNA single- or double-stranded viruses, bacteria, rickettsia or parasites to provide for a method of treatment or prevention.

BACKGROUND

Influenza is a common infectious disease brought about by an RNA virus of the same name. While vaccines for influenza have been available, strains of influenza evolve readily and novel viruses emerge from various species (e.g. bird to human transfer) requiring new vaccines to be provided on seasonal or sporadic basis. Similarly, other disease causing agents including various viruses such as HIV, HTLV viruses and others evolve readily and novel viruses emerge from various species (e.g. bird, rodents, livestock and other primate-to-human transfer) requiring new vaccines to be provided on seasonal or sporadic basis. Whole virus vaccines, split virus vaccines, surface antigen vaccines and live attenuated virus vaccines are available for influenza. However, presently available vaccines require constant updating because of 1) mutations, 2) re-assortment of genes between various strains, and 3) the continual emergence (or re-emergence) of different strains.

Common vaccines for influenza are designed to induce an immune response that is directed at the so-called protective antigens, hemagglutinin (HA or H) and neuramindase (NA or N), and the vaccines induce strain specific immunity.

Each year, numerous individuals are infected with different strains and types of influenza virus. Oftentimes, complications from influenza infection lead to protracted illness or death. Infants, the elderly, those without adequate health care and immuno-compromised persons are particularly vulnerable to complications arising from influenza infections. In some cases, otherwise healthy adults are at risk for severe complications including death from influenza infection. The 1918 Spanish influenza, which was genetically related to the 2009 pandemic H1N1 influenza, had the propensity for affecting individuals with healthy immune systems. The H5N1 influenza virus is also believed to have a heightened risk for affecting individuals with healthy immune systems, which may result in a cytokine storm (hypercytokimemia). A cytokine storm is caused by excessive amounts of pro-inflammatory cytokines and tends to occur in patients with stronger, "robust," immune systems and leads to an increased risk for death in otherwise healthy adults. There is a need for a formulation and a method of vaccination and/or treatment to combat a deadly pandemic and to protect against new strains of Type A influenza that may present an elevated risk for even those with healthy immune systems. Emergent influenza viruses can be the most deadly for people in their prime, rather than affecting only the very young, the very old, or the most severely immuno-compromised.

Appropriate formulations of peptide constructs can stimulate and produce a systemic immune response. Peptide construct technology has provided the ability to produce vaccines using genetic engineering (recombinant vaccines). Such vaccines are typically created using antigenic moieties of the newly emergent virus strains when polypeptides and polynucleotides of novel, newly emergent, or newly re-emergent virus strains are desired. The focus on most current vaccines is not on conserved proteins and, especially, essential regions of such conserved proteins.

SUMMARY OF THE INVENTION

Peptides and compositions for use in treatment for Type A influenza infections and other infectious diseases are disclosed, including the treatment of HSV I, II, EBV, VZV, CMV, KHSV (HSV-VIII), HTLV-I, HTLV-II, HBV, RSV, HPV, TB, and the causative agent of Lyme disease. Peptides and compositions disclosed herein are competent for the ex vivo treatment of immune cells for maturation and/or activation of immunity infection as well as methods for the use of such matured immune cells for the prevention and treatment of many of these agents and related diseases. The peptide constructs disclosed herein are based on a Ligand Epitope Antigen Presentation System (LEAPS™) technology that can convert small peptides, which typically do not elicit strong and protective immune responses, into immunogens that do elicit an immune response.

In certain embodiments, peptides and compositions disclosed herein are competent for the ex vivo treatment of immune cells for maturation and/or activation of immunity against Type A influenza infection as well as methods for the use of such matured immune cells for the prevention and treatment of Type A influenza infections. The peptide constructs disclosed herein are based on a Ligand Epitope Antigen Presentation System (LEAPS™) technology that can convert small peptides that typically do not elicit strong and protective immune responses, into immunogens that do elicit an immune response.

In certain embodiments, the novel heteroconjugates or peptide constructs disclosed herein are based upon highly-conserved sequences common to various strains of Type A Influenza viruses (H1N1, H5N1, H3N2, etc.), including "swine," "avian" or "bird," and "Spanish Influenza," in order to minimize the chance of insufficient immunity due to mutation. As such, the heteroconjugates or peptide constructs provide immunity to more than one sub-type and/or strain of type A influenza virus. That is, the novel heteroconjugates or peptide constructs promote immune recognition of antigens and/or epitopes common to different subtypes and strains of Type A influenza viruses and common between different Type A influenza viruses.

In certain embodiments, a composition contains one or more heteroconjugates or peptide constructs or dendritic cells treated with one or more heteroconjugates or peptide constructs for treatment or immunization to several or multiple subtypes of type A influenza.

In certain embodiments, a composition containing one or more heteroconjugates or peptide constructs or dendritic cells treated with one or more heteroconjugates or peptide constructs for treatment or immunization to several or multiple subtypes of type A influenza.

In certain embodiments, a composition containing one or more heteroconjugates or peptide constructs or dendritic cells treated with one or more heteroconjugates or peptide constructs acts as a multi-strain influenza vaccine or as a treatment for more than one influenza sub-type and/or strain.

In certain embodiments, a composition containing one or more heteroconjugates or peptide constructs or dendritic cells treated with one or more heteroconjugates or peptide constructs acts as a multi-subtype influenza vaccine or as a treatment more than one influenza sub-type and/or strain.

In certain embodiments, a composition for use as a treatment or as an influenza vaccine for more than one sub-type and/or strain of type A influenza virus contains from about 1 to about 10 or less peptide conjugates containing an immune cell binding ligand (ICBL) as described herein. In other embodiments, a composition for use as a treatment or as an influenza vaccine for more than one sub-type and/or strain of type A influenza virus contains from about 3 to about 5 or less peptide conjugates containing an ICBL as described herein. In further embodiments, a composition for use as a treatment or as an influenza vaccine for more than one sub-type and/or strain of type A influenza virus contains from about 3 to about 10 or less peptide conjugates containing an ICBL as described herein.

In certain embodiments, peptide heteroconjugates having an immunomodulatory effect for influenza infection include the peptide heteroconjugate DLLKNGERIEKVEGGGN-DATYQRTRALVRTG (SEQ ID No. 1), containing two elements of the LEAPS™ heteroconjugate construct, namely an immune cell binding ligand (ICBL) Peptide J, DLLKNGERIEKVE (SEQ ID No. 3) linked to a peptide derived from the nucleoprotein (NP) of the Type A influenza virus NDATYQRTRALVRTG (SEQ ID No. 7). Another LEAPS™ peptide heteroconjugate having immunomodulatory effect for influenza infection is the peptide construct DLLKNGERIEKVEGGGSLLTEVET-PIRNEWGCRCNDSSD (SEQ ID No. 2), containing two elements of the LEAPS™ heteroconjugate construct, namely a ICBL Peptide J, DLLKNGERIEKVE (SEQ ID No. 3) linked to a peptide derived from the matrix 2 ectodomain (M2e) of the A virus SLLTEVETPIRNEWGCRCNDSSD (SEQ ID No. 8). Additional peptide constructs having immunomodulatory effects are disclosed.

In certain embodiments, a peptide construct for directing an immune response against various infectious disease causing agents or for maturing dendritic cells from immature dendritic cells to a more matured and now activated dendritic cell are provided. The peptide has the formula $P_1$-x-$P_2$ or $P_2$-x-$P_1$, where $P_2$ represents a specific antigenic peptide, $P_1$ represents an immunomodulatory peptide, which is a portion of an immunoprotein capable of promoting binding to a class or subclass of immune cells, and x represents a covalent bond or a divalent linking group.

In certain embodiments, a composition having a population of matured dendritic cells is provided. The population of matured dendritic cells is formed by treating immature dendritic cells or monocytes with an effective amount of a peptide construct having the formula $P_1$-x-$P_2$ or $P_2$-x-$P_1$ under conditions suitable for maturation of the cells to form the matured or effective dendritic cells which interacts with T cells, where $P_2$ represents a specific antigenic peptide, $P_1$ represents an immunomodulatory peptide which is a portion of an immunoprotein capable of promoting binding to a class or subclass of DC or T cells, and -x- represents a covalent bond or a divalent linking group.

In certain embodiments, a peptide for directing an immune response against Type A influenza virus or for maturing dendritic cells from immature dendritic cells to a more matured and now activated dendritic cell is provided. The peptide has the formula $P_1$-x-$P_2$ or $P_2$-x-$P_1$ where $P_2$ represents a specific antigenic peptide derived from a Type A influenza virus, $P_1$ represents an immunomodulatory peptide which is a portion of an immunoprotein capable of promoting binding to a class or subclass of immune cells, and x represents a covalent bond or a divalent linking group.

In certain embodiments, a composition comprising a population of matured dendritic cells is provided. The population of matured dendritic cells is formed by treating immature dendritic cells or monocytes with an effective amount of a peptide construct having the formula $P_1$-x-$P_2$ or $P_2$-x-$P_1$ under conditions suitable for maturation of the cells to form the matured or effective dendritic cells which interacts with T cells, where $P_2$ represents a specific antigenic peptide derived from an influenza virus, $P_1$ represents an immunomodulatory peptide which is a portion of an immunoprotein capable of promoting binding to a class or subclass of DC or T cells, and -x- represents a covalent bond or a divalent linking group.

In certain embodiments, a method for targeting matured or effective dendritic cells to an infection site in a subject is provided. Immature dendritic cells or monocytes are treated with a peptide construct ex vivo under conditions suitable for maturation of the cells to form more matured or activated dendritic cells, and an effective amount of these matured dendritic cells are administered to the subject, wherein a majority of the dendritic cells administered to the subject locate to the infection site.

In certain embodiments, a therapeutic method of inducing an immune response in an animal subject infected with an infectious agent is provided by maturing dendritic cells (DC) by ex vivo treatment with an effective amount of a LEAPS™ heteroconjugate construct having immunomodulatory effect for infections or a mixture of LEAPS™ heteroconjugates having immunomodulatory effect when administered to a subject. The matured dendritic cells can then be transferred to an animal subject to confer immunity to an infectious agent or to treat an on-going viral, bacterial, parasitic or rickettsial infection. In certain embodiments, the LEAPS™ heteroconjugate can be administered to a subject to confer active immunity to infections in a manner similar to traditional vaccines containing attenuated virus, live virus, or viral proteins or protein fragments, wherein the LEAPS™ heteroconjugate is administered direct to a subject with or without an optional adjuvant.

In certain embodiments, therapeutic method of inducing an immune response in an animal subject infected with Type A influenza virus is provided by maturing dendritic cells (DC) by ex vivo treatment with an effective amount of a LEAPS™ heteroconjugate construct having immunomodulatory effect for influenza infection or a mixture of LEAPS™ heteroconjugates having immunomodulatory effect for influenza infection. The matured dendritic cells can then be transferred to an animal subject to confer immunity to Type A influenza virus or to treat an ongoing influenza infection. In certain embodiments, the LEAPS™ heteroconjugate can be administered to a subject to confer active immunity to influenza infections in a manner similar to traditional influenza vaccines containing attenuated virus, live virus, or viral proteins or protein fragments, wherein the LEAPS™ heteroconjugate is administered direct to a subject with or without an optional adjuvant.

In certain embodiments, a method for modulating a response to an infection in a subject in need thereof is provided by combining dendritic cells (DCs) and/or monocytes, that can be derived from an infected subject or a suitably matched donor, with a LEAPS™ heteroconjugate having immunomodulatory effect for the infection ex vivo to form a mixture, and administering the mixture to the subject. A method for modulating a response to an infection in a subject is provided by treating isolating DCs and/or monocytes from blood derived monocytes and/or bone marrow taken from the subject with a LEAPS™ heteroconjugate to induce maturation of the DCs and/or monocytes into matured DCs and administering, optionally without any supplementary immunomodulators, an effective amount of the treated matured DCs back into the subject.

In certain embodiments, method for modulating a response to Type A influenza virus in a subject in need thereof is provided by combining dendritic cells (DCs) and/or monocytes, that can be derived from an influenza infected subject or a suitably matched donor, with a heteroconjugate having immunomodulator effect for influenza virus ex vivo to form a mixture and administering the mixture to the subject. A method for modulating a response to Type A influenza virus in an infected subject is provided by treating isolated DCs and/or monocytes from blood derived monocytes and/or bone marrow taken from the subject with a heteroconjugate to induce maturation of the DCs and/or monocytes into matured DCs and administering, optionally without any supplementary immunomodulators, an effective amount of the treated matured DCs back into the subject.

In certain embodiments, additional heteroconjugates having immunomodulatory effect for influenza virus include, in addition to the heteroconjugates SEQ ID No. 1 or SEQ ID No. 2, heteroconjugates including the Peptide J (SEQ ID No. 3), Peptide G (SEQ ID No. 6) or CEL-1000 (SEQ ID No. 4) sequences conjugated with HA2 core 1, GLFGAIAGFIEGG (SEQ ID No. 10) or HA2 core 2, LKSTQNAIDEITNKVN (SEQ ID No. 9). A heteroconjugate of Peptide J (SEQ ID No. 3) and HA2 core 1, GLFGAIAGFIEGG (SEQ ID No. 10), with a spacer GGG, is DLLKNGERIEKVEGGGGLFGAIAGFIEGG (SEQ ID No. 12). A heteroconjugate of Peptide J (SEQ ID No. 3) and HA2 core 2, LKSTQNAIDEITNKVN (SEQ ID No. 9), with a spacer GGG, is DLLKNGERIEKVEGGGLKSTQNAIDEITNKVN (SEQ ID No. 11). Any of the heteroconjugate can optionally be combined with an adjuvant for in vivo use by administration into a living animal or human.

In certain embodiments, a tracking marker or a therapeutic agent is conjugated to an antibody having affinity for any one of MHC II, CD11c, DEC-205, Dectin-1, DC-SIGN, and DC-LAMP.

In certain embodiments, a peptide conjugate or an dendritic cell is conjugated to a therapeutic agent selected from the group consisting of reverse transcriptase inhibitors, portmanteau inhibitors, integrase inhibitors, protease inhibitors, entry inhibitors, CCR5 receptor antagonists, maturation inhibitors, agents from the ARV NRTI group, penicillins, cephalosporins, vancomycin, tetracyclines, macrolides, chloramphenicol, clindamycin, spectinomycin, sulfonamides, DNA-gyrase inhibitors, antimycobacterial agents, protein synthesis inhibitors, mefloquine, doxycycline, atovaquone, proguanil hydrochloride, proguanil, quinacrine, chloroquine, primaquine, amoxicillin, penicillin G, and clarithromycin.

In certain embodiments, matured dendritic cells exhibit an upregulation of one or more of CD80, CD86 and Major Histocompatibility Complex II relative to immature dendritic cells or monocytes not contacted with the peptide construct.

In certain embodiments, matured dendritic cells are isolated away from bone marrow or blood tissues.

In certain embodiments, matured dendritic cells produce an increased amount of Interleukin 12p70 (IL-12p70) compared to immature dendritic cells or monocytes not contacted with the peptide construct.

In certain embodiments, a therapeutic agent or a tracking marker is conjugated to a peptide conjugate the peptide construct is conjugated to the therapeutic agent by a cathepsin cleavable valine-citrulline dipeptide linker or by linking with a cysteine or lysine residue of the peptide construct by conjugation to a group selected from OH groups, COOH groups, amine groups, and amide groups of the peptide construct.

In certain embodiments, a peptide construct is conjugated to a lysosmatropic agent.

In certain embodiments, a peptide for directing an immune response against an infection or for maturing dendritic cells is a peptide construct selected from the group consisting of SEQ ID No.'s 140-189 and 209-218 or a variant thereof.

In certain embodiments, a composition containing matured dendritic cells is provided. The matured dendritic cells are formed by contacting immature dendritic cells or monocytes with an effective amount of a peptide construct having the formula $P_1$-x-$P_2$ or $P_2$-x-$P_1$ under conditions suitable for maturation of the immature dendritic cells to form the matured dendritic cells, wherein $P_2$ represents a specific antigenic peptide derived from infectious, viral, bacterial, parasitic disease causing agent; $P_1$ represents an immunomodulatory peptide which is a portion of an immunoprotein capable of promoting binding to a class or subclass of dendritic cells; and x represents a covalent bond or a divalent linking group.

In certain embodiments, a composition containing a population of matured dendritic cells is provided. The matured dendritic cells formed are by contacting immature dendritic cells or monocytes with an effective amount of a peptide construct selected from the group consisting of SEQ ID No.'s 140-189 and 209-218 or a variant thereof under conditions suitable for maturation of the dendritic cells or monocytes.

In certain embodiments, a method for inducing a systemic immune response to an infection includes administering an immunologically effective amount of a peptide construct selected from the group consisting of SEQ ID No.'s 140-189 and 209-218 or a variant thereof to a subject.

In certain embodiments, a method for producing a matured dendritic cell population is performed by contacting or treating immature dendritic cells or monocytes with an effective amount of a peptide construct having the formula $P_1$-X-$P_2$ or $P_2$-X-$P_1$ under conditions suitable for maturation of dendritic cells or monocytes to form matured dendritic cells, wherein $P_2$ represents a specific antigenic peptide derived from infectious, viral, bacterial, parasitic disease causing agent; $P_1$ represents an immunomodulatory peptide which is a portion of an immunoprotein capable of promoting binding to a class or subclass of dendritic cells; and x represents a covalent bond or a divalent peptide linking group.

In certain embodiments, an immune response in a subject is modulated or a subject is vaccinated by contacting immature dendritic cells or monocytes with a peptide construct having the formula $P_1$-x-$P_2$ or $P_2$-x-$P_1$ under conditions suitable for maturation of the cells to form matured dendritic cells and administering an effective amount of the matured dendritic cells to the subject. In the peptide construct, $P_2$ represents a specific antigenic peptide derived from infectious, viral, bacterial, parasitic disease causing agent; $P_1$ represents an immunomodulatory peptide which is a portion of an immunoprotein capable of promoting binding to a class or subclass of dendritic cells; and x represents a covalent bond or a divalent peptide linking group.

In certain embodiments, the peptide construct having the formula $P_1$-x-$P_2$ or $P_2$-x-$P_1$ has a peptide $P_1$ selected from the group consisting of SEQ ID No.'s 3-6 and 40 or variants thereof.

In certain embodiments, the peptide construct having the formula $P_1$-x-$P_2$ has a peptide $P_2$ selected from one of the following groups: the group consisting of SEQ ID No.'s 7-10 and 41-46; the group consisting of SEQ ID No.'s 53-56; the group consisting of SEQ ID No.'s 57-60; the group consisting of SEQ ID No.'s 61-64; the group consisting of SEQ ID No.'s 65-66; the group consisting of SEQ ID No.'s 67-68; the group consisting of SEQ ID No.'s 69-70; the group consisting of SEQ ID No.'s 71-72; the group consisting of SEQ ID No.'s 73-74; the group consisting of SEQ ID No.'s 75-80; the group consisting of SEQ ID No.'s 81-82; the group consisting of SEQ ID No.'s 83-86; the group consisting of SEQ ID No.'s 87-90; the group consisting of SEQ ID No.'s 91-99; the group consisting of SEQ ID No.'s 100-114; the group consisting of SEQ ID No.'s 115-120; the group consisting of SEQ ID No.'s 121-124; the group consisting of SEQ ID No.'s 125-126; the group consisting of SEQ ID No.'s 128-129; SEQ ID No. 127; the group consisting of SEQ ID No.'s 131-133; the group consisting of SEQ ID No.'s 194-195; the group consisting of SEQ ID No.'s 135-136; the group consisting of SEQ ID No.'s 137-138; SEQ ID No. 139; the group consisting of SEQ ID No.'s 196-204; and the group consisting of SEQ ID No.'s 205-208, or variants of any of the foregoing sequences.

In certain embodiments, the peptide construct is selected from one of the following groups: the group consisting of SEQ ID No.'s 1-2, 11-36, 47-52; the group consisting of SEQ ID No.'s 140-141; the group consisting of SEQ ID No.'s 142-143; the group consisting of SEQ ID No.'s 144-146; SEQ ID No. 147; SEQ ID No. 148; SEQ ID No. 149; SEQ ID No. 150; SEQ ID No. 151; the group consisting of SEQ ID No.'s 152-154; SEQ ID No. 155; the group consisting of SEQ ID No.'s 156-157; the group consisting of SEQ ID No.'s 158-159; the group consisting of SEQ ID No.'s 160-165; the group consisting of SEQ ID No.'s 166-173; the group consisting of SEQ ID No.'s 174-176; the group consisting of SEQ ID No.'s 177-178; SEQ ID No. 179; SEQ ID No. 180; the group consisting of SEQ ID No.'s 181-182; SEQ ID No. 183; SEQ ID No. 184-185 and 209-210; and SEQ ID No. 186 and 211; SEQ ID No. 187; SEQ ID No. 188; SEQ ID No. 189; the group consisting of SEQ ID No.'s 212-216; and the group consisting of SEQ ID No.'s 217-217, or variants of any of the foregoing sequences.

One of ordinary skill in the art will appreciate that other aspects of this invention will become apparent upon reference to the following detailed description.

BRIEF DESCRIPTION OF THE DRAWINGS

FIG. 1A represents two-dimensional data for forward scattering and side scattering of BMDCs; the boxed area represents the characteristics anticipated for dendritic cells. FIGS. 1B through 1G present one-dimensional flow cytometry data for cell surface markers of BMDCs detected by immunofluorescence (unshaded areas). FIG. 1B presents immunofluorescence data for the presence of CD3; FIG. 1C presents immunofluorescence data for the presence of CD19; FIG. 1D presents immunofluorescence data for the presence of CD11c; FIG. 1E presents immunofluorescence data for the presence of CD86; FIG. 1F presents immunofluorescence for the presence of Major Histocompatibility Complex II (MHC II); and FIG. 1G presents immunofluorescence for the presence of F4/80. In FIGS. 1B through 1G, shaded areas represent data collected using an appropriate isotype control antibody-fluorescent conjugate. The isotype control is an antibody conjugate of the same serological isotype labeled with the same fluorescent dye as the antibody recognizing a cellular surface or cytokine marker but with no binding activity to these cellular or cytokine markers.

FIG. 2A presents four separate one-dimensional flow cytometry data plots for cells surface markers CD80, MHC II, CD86 and CD11c for un-treated DCs (iDCs) as well as DCs treated with lipopolysaccharide (LPS) for 24-, 48- and 78-hour periods as indicated in the legend. Shaded data represent data collected using an appropriate isotype control antibody-fluorescent conjugate. FIGS. 2B through 2D represent analogous data for DCs treated with J-H (SEQ ID No. 37), J-NP (SEQ ID No. 1) and J-M2e (SEQ ID No. 2), respectively.

FIG. 3A presents four separate one-dimensional flow cytometry data plots for cells surface markers CD80, MHC II, CD86 and CD11c for untreated DCs (iDCs) as well as DCs treated with J-HA1 (SEQ ID No. 12) for 24-, 48- and 78-hour periods as indicated in the legend. Shaded data represent data collected using an appropriate isotype control antibody-fluorescent conjugate. FIGS. 3B through 3C represent analogous data for DCs treated with J-HA2 (SEQ ID No. 11) and a combination of J-H, J-NP, J-M2e, J-HA1 and J-HA2, respectively.

FIG. 4A represents data collected for cell surface marker CD80; Figure B represents data collected for cell surface marker CD11C; FIG. 4C represents data collected for cell surface marker MHC II; and FIG. 4D represents data collected for cell surface marker CD86.

FIG. 8A represents the weight progression for a group of 10 individuals treated 8 hours post infection with DCs that were not treated with a LEAPS™ heteroconjugate. FIG. 8B represents the weight progression of a group of 10 individual mice treated starting at 8 hours post infection with DCs treated with a LEAPS™ heteroconjugate. FIG. 8C represents the weight progression of a group of 10 individual mice treated starting at 24 hours post infection with DCs not treated with a LEAPS™ heteroconjugate. FIG. 8D represents the weight progression of a group of 10 individual mice treated starting at 24 hours post infection with DCs treated with a LEAPS™ heteroconjugate.

FIGS. 9A through 9C represent flow cytometry data for cells extracted from lung tissue of individual mice treated with DCs that were not treated with a LEAPS™ heteroconjugate. FIGS. 9D through 9F represent flow cytometry data for cells extracted from lung tissue of individual mice treated with DCs treated with a LEAPS™ heteroconjugate.

DETAILED DESCRIPTION OF THE INVENTION

Figure 1:
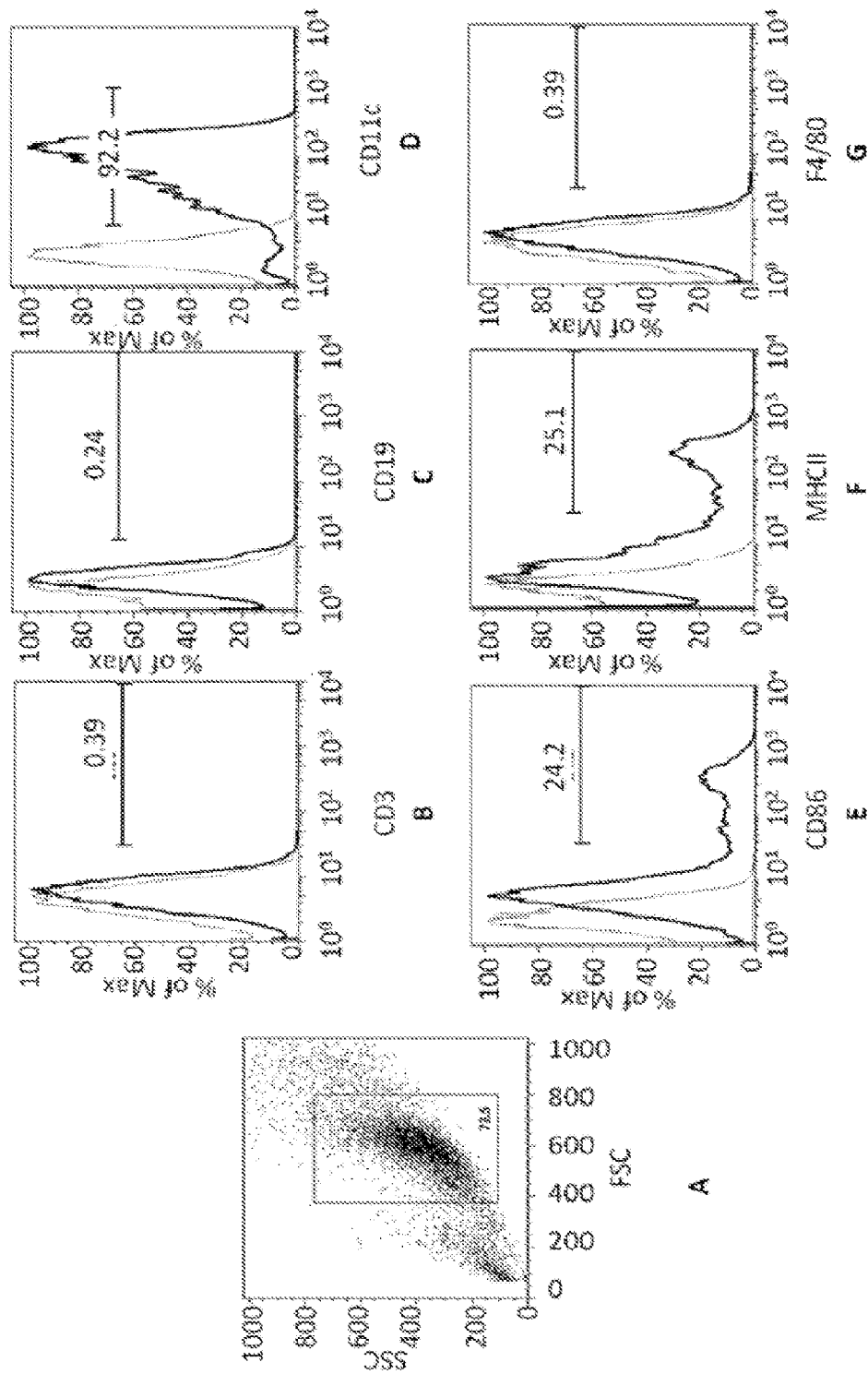
FIGS. 1A through 1G represent flow cytometry data for bone marrow (BM) cells isolated from BALB/c mice. Each flow cytometry plot was collected from approximately $10^6$ bone marrow-derived dendritic cells (BMDC) cells.

The present invention provides LEAPS™ peptide conjugates useful for treatment or prevention of various infections. The novel heteroconjugates disclosed herein are based upon conserved, non-changing epitope sequences common to various strains of viruses, bacteria, rickettsia or parasites, as applicable, in order to minimize the chance of insufficient immunity due to mutation and minor strain variations. The use of LEAPS™ vaccine technology for immunization in animal models has been shown to provide protection from viral diseases without causing an immune response associated with the deadly "cytokine-storm" seen in some of the victims of viral infections in particular. The present invention also provides new approaches for detection and/or treatment that are suitable for use in treatment as well as in research, diagnostics, etc. Numerous other benefits will become apparent upon review of the following.

The present invention provides LEAPS™ peptide conjugates useful for treatment of Type A influenza. The novel heteroconjugates disclosed herein are based upon conserved, non-changing epitope sequences common to various strains of Type A Influenza viruses (H1N1, H5N1, H3N2, etc.), including "swine," "avian" or "bird," and "Spanish Influenza," in order to minimize the chance of insufficient immunity due to mutation. The use of LEAPS™ vaccine technology for immunization in animal models has been shown to provide protection from viral diseases without causing an immune response associated with the deadly "cytokine-storm" seen in some of the victims of influenza. The present invention also provides new and/or newly isolated influenza hemagglutinin and neuraminidase fragments that are capable of use in production of numerous types of vaccines as well as in research, diagnostics, etc. Numerous other benefits will become apparent upon review of the following.

The present invention provides LEAPS™ peptide heteroconjugates useful for treatment of diseases such as influenza, HSV, other viruses, bacteria, rickettsia or parasitic infections and localization of these LEAPS™ heteroconjugate-activated DCs at the site of the ongoing disease or infection whether visualized by labeling with CFSE, a radioactive label such as $^{131}$I or $^{125}$I, some other visualization means or as unlabeled DCs. The novel heteroconjugates disclosed herein are based upon conserved, non-changing epitope sequences common to the disease causing organism or virus (pathogen) or protein (or peptide) and are often or usually essential for its existence.

Definitions

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "adjuvant" refers to substance that accelerates, prolongs or enhances antigen-specific immune responses when used in combination with vaccine antigens.

The terms "administering," "administer," "delivering," "deliver," "introducing," and "introduce" can be used interchangeably to indicate the introduction of a therapeutic or diagnostic agent into the body of a patient in need thereof to treat a disease or condition, and can further mean the introduction of any agent into the body for any purpose.

The term "antigen" refers to a substance or molecule that generates an immune response when introduced to the body or any molecule or fragment thereof now also refers to any molecule or molecular fragment that can be bound by a major histocompatibility complex (MHC).

The term "blood tissue" refers to cells suspended in or in contact with plasma.

The term "bone marrow cell" refers to any cell originating from the interior of bones.

The terms "CD80," "CD86," "CD11c, "CD85" and similar terms refer to cell surface molecules present on leukocyte cells through a nomenclature protocol maintained by Human Cell Differentiation Molecules (www.hcdm.org; Paris, France).

The term "comprising" includes the recited steps, elements, structures or compositions of matter and does not exclude any un-recited elements, structures or compositions of matter.

The term "consisting of" includes and is limited to whatever follows the phrase the phrase "consisting of." Thus, the phrase indicates that the limited elements are required or mandatory and that no other elements may be present.

The phrase "consisting essentially of" includes any elements listed after the phrase and is limited to other elements that do not interfere with or contribute to the activity or action specified in the disclosure for the listed elements. Thus, the phrase indicates that the listed elements are required or mandatory but that other elements are optional and may or may not be present, depending upon whether or not they affect the activity or action of the listed elements.

A "dendritic cell" or "DC" refers to an antigen-presenting leukocyte that is found in the skin, mucosa, and lymphoid tissues and having a capability under appropriate conditions to initiate a primary immune response by activating T cells, lymphocytes and/or secreting cytokines.

The term "diagnostic" refers to any technique for determining the presence of any influenza viral infection or antigen in a subject.

The term "divalent linker" refers to any moiety having a structure forming a peptide bond to a first peptide moiety and forming a second bond to a second peptide moiety.

The term "effective amount" is an amount of a therapeutic which produces a therapeutic response, including an immune response, in the subject to which the therapeutic is administered.

The term "ex vivo" refers to an operation or procedure that is performed outside of the body of a patient or subject to be treated for an influenza viral disease. For example, an ex vivo procedure can be performed on living cells originating from the patient, subject or donor removed from the body.

The term "autologous" refers to a situation where the donor and recipient of cells, fluids or other biological sample or material is the same individual.

The term "homologous" refers to a situation where the donor are recipient of cells, fluids or other biological sample or material are not the same individual.

The term "Herpes simplex virus 1 and 2" (HSV-1 and HSV-2) refers to members of the family Herpesviridae of double-stranded DNA viruses. HSV-1 is associated with producing cold sores in humans and HSV-2 is associated with producing genital herpes.

The term "human T-lymphotropic virus Type I" (HTLV-1) refers to a human RNA retrovirus that causes T-cell leukemia and T-cell lymphoma in humans and other primates.

The terms "conjugate," "conjugation" and similar terms refer to two species being spatially associated with each other by covalent linkage, non-covalent binding or by a combination of covalent linkage and non-covalent binding. For example, an antibody can be conjugated to an epitope through non-covalent binding to the epitope as well as the antibody serving to conjugate the epitope (such as a cell surface marker) to a compound that is linked to the antibody.

An "immature dendritic cell" is a "dendritic cell" in a state characteristic of immune cells prior to contact with an antigen and having a limited present ability to activate T cells, lymphocytes and/or to secrete cytokines; however, "immature dendritic cells" may acquire the ability to activate T cells, lymphocytes and secrete cytokines upon contact with an antigen.

The terms "immunomodulatory" and "immunoprotein" refer to a protein, peptide or cell having the ability to bind or interact with an immune cell to alter or to regulate one or more immune functions.

The term "infection" refers to the colonization in a host organism by a pathogenic influenza virus.

The term "Influenza virus" refers to an RNA virus from the Orthomyxoviridae family.

The term "influenza subtype" means an influenza virus having a specific sub-type of hemagglutinin protein (H) on the viral envelope and a specific sub-type of neuraminidase (N) as classified by the Centers for Disease Control and Prevention (Atlanta, Ga.).

The term "strain" as it relates to influenza virus refers to an influenza virus having a specific strain number as classified by the Centers for Disease Control and Prevention (Atlanta, Ga.), wherein the strain number can include an identifier that incorporates information or identification of the site or location where the specific strain was found, features of the sub-types of the hemagglutinin (H) and neuraminidase (N) proteins and the year of isolation or passage.

The term "multi-strain influenza vaccine" means a vaccine that is active in conferring immunity to multiple (usually only 3 to 4 on 1-9 different H and 1-9 different N proteins) strains of type A influenza virus that have accumulated genetic drift between strains. For example, a multi-strain influenza vaccine may, in some embodiments, confer immunity to influenza strains having 3 or 4 or more different hemagglutinin (H) and neuraminidase (N) protein sub-types as classified by the Centers for Disease Control and Prevention (Atlanta, Ga.).

The term "multi-subtype influenza vaccine" means a vaccine that is active in conferring immunity to multiple (usually only 3 to 4 on 1-9 different H and 1-9 different N proteins) strains of type A influenza virus that have accumulated genetic drift between strains. For example, a multi-strain influenza vaccine may, in some embodiments, confer immunity to influenza strains having 3 or 4 or more different hemagglutinin (H) and neuraminidase (N) protein sub-types as classified by the Centers for Disease Control and Prevention (Atlanta, Ga.).

The term "Interleukin 12p70" refers to a cytokine produced by dendritic cells capable of directing the development of lymphocytes in a Th1 immune response, and possessing two peptides of approximately 40 kd and 35 kd in size.

The terms "isolated matured dendritic cells" or "isolated dendritic cells" refer to dendritic cells suspended in a liquid medium, a cell culture or a composition wherein at least 50% of the viable cells present in the liquid medium, the cell culture or the composition are dendritic cells or monocytes.

An "isotype control" is an antibody having the same serological structure and can have a fluorescent conjugate dye as an antibody conjugate having affinity for a cellular surface or cytokine marker, except the isotype control does not have affinity for the cellular surface or cytokine marker.

A "heteroconjugate" refers to a protein or peptide containing at least two amino acid sequences covalently linked to form a single molecule, wherein two sequences originate or are homologous to proteins expressed by different genes.

The term "maturation" refers to a process for generating a "matured dendritic cell."

The terms "matured dendritic cell," "maturated dendritic cell," "activated dendritic cell" or "effective dendritic cell" refer to a "dendritic cell" in a state characteristic of cells after contact with an antigen and having a present ability to initiate a primary immune response by activating T cells, lymphocytes and/or secreting cytokines.

The term "MDCK" refers to the Madin-Darby canine kidney epithelial cell line.

The term "monocyte" refers to immune cells produced by bone marrow and haematopoietic stem cell having the ability to differentiate into macrophages or dendritic cells.

The term "magnetic resonance imaging" refers to any technique where information is collected from the exposure of a subject or sample to a magnetic field.

The terms "H1N1," "H5N1," "H7N3," "H9N2," and similar terms refer to specific subtypes of influenza Type A virus, where the numeral after "H" designates a type of hemagglutinin protein on the viral envelope and the numeral after "N" designates a type of neuraminidase as classified by the Centers for Disease Control and Prevention (Atlanta, Ga.).

The terms "originating" and "derived" as related to a peptide sequence refers to an organism or cell type that produces a protein containing the peptide sequence.

The term "TCID$_{50}$" refers to the median tissue culture infective dose of a pathogenic agent that produces pathological change in 50% of cell cultures inoculated.

The terms "peptide" and "peptide construct" refer to a molecule including two or more amino acid residues linked by a peptide bond. The term "peptide" includes molecular species where only part of the molecule has peptide character and/or where two parts of the molecular species formed of peptide bonds are covalently linked by a divalent linker.

The term "phenotype" as relating to the phenotype of immune cells refers to any observable characteristic or trait of a cell such as its morphology, development, biochemical or physiological properties including the expression or presence of specific cell surface proteins or markers.

The term "poliovirus" refers to a human enterovirus and member of the family Picornaviridae with a single-stranded, positive-sense RNA genome. Poliovirus is associated with causing poliomyelitis also known as infantile paralysis.

The term "prophylactic" or "prophylactically" refers to a method or use of a peptide, cells or biological matter in a manner to prevent the onset or occurrence of a disease or infection including use as a vaccine.

The term "red blood cells" refers to erythrocytes having an intact phospholipid bilayer membrane.

The term "rickettsia" refers to bacteria that are obligate intracellular parasites that have a cell well and are typically gram-negative.

The term "subject" or "patient" refers to an animal, including mice and humans, to which a therapeutic agent is administered.

The term "systemic immune response" refers to an immune response where antibodies, cytokines or immune cells generated by the immune response are detectable throughout the circulatory and lymph systems of the body.

The term "T cell" refers to a lymphocyte having a T cell receptor protein on the surface of the cell.

"Type A influenza virus" refers to an RNA virus from the Orthomyxoviridae family characterized by the presence of at least three membrane proteins on the viral envelope: hemagglutinin, Neuraminidase and M2 proton-selective ion channel protein.

The terms "treating" and "treatment" as related to treating or treatment of immune cells refers to bringing an immune cell into contact with a substance or composition for a time period sufficient to cause a change in phenotype. The term "vaccine" refers to composition containing one or more antigens that stimulates an immune response when administered to an organism in vivo.

The term "virus" refers to a small infectious agent that can replicate only inside the living cells of another organism or host through the use of some of the host's own cellular machinery (e.g. ribosomes) for growth and replication. Viruses outside of the host cells are formed from a nucleic acid with an associated protein coat.

Structure of Immunomodulatory LEAPS™ Heteroconjugates

The peptide constructs disclosed herein are based on LEAPS™ technology and are conjugates of two peptides which are linked together covalently. The peptide constructs can be synthesized artificially using solid-phase synthesis or other synthetic technique or expressed using recombinant DNA technology. The two peptides can be synthesized separately and joined covalently or can be synthesized or expressed as a single construct. The LEAPS™ heteroconjugates are formed by joining a Peptide $P_1$ and a Peptide $P_2$ originating from different species by a linker "-x-," such that the heteroconjugate has the structure $P_1$-x-$P_2$ or $P_2$-$P_1$. A first peptide (hereinafter may be referred to as Peptide $P_1$) of the conjugate is a portion of an immunoprotein capable of promoting binding to a class or subclass of dendritic cells (DCs) or T cells and is referred to as an immune cell binding ligand (ICBL). Without wishing to be bound by any particular theory, it is believed that Peptide $P_1$ has a structure for promoting interaction and/or binding with specific surface receptors present on DCs. Peptide $P_1$ can be a peptide sequence derived from Major Histocompatibility Complex (MHC) I or II. A more detailed discussion of the Peptide $P_1$ and peptide conjugates involved with LEAPS™ technology can be found in U.S. Pat. No. 5,652,342, which is incorporated herein by reference.

A second peptide (hereinafter may be referred to as Peptide $P_2$) is a specific antigen peptide derived from a virus or infecting agent such as Type A influenza or other virus, parasite, bacteria or infectious agent. As described, the sequence of Peptide $P_2$ is associated with sequences with a low-degree of variability between strains of viruses and can be identical to sequences present across several strains of the particular virus, bacteria, rickettsia, parasite, etc. In particular for Type A influenza virus, the sequence of Peptide $P_2$ can be identical to sequences present across several strains of influenza virus, e.g. H1N1, H5N1, H7N3, H9N2, etc. Without wishing to be bound by any particular theory, it is believed that the antigen Peptide $P_2$ being covalently bound to the ICBL Peptide $P_1$ allows for a more effective recognition of the antigen Peptide $P_2$ by the immune system and specific immune cells. Peptide epitopes having a limited number of amino acid residues have sufficient structure to be bound by an antibody or an MHC molecule with a high degree of specificity. However, peptide epitopes of limited size are less competent to cross-link immunoglobulins to cause lymphocyte activation and/or to be effectively displayed to T cells to stimulate cellular or humoral immune response. As such, small peptide epitopes introduced into a subject may produce a poor immune response. In the LEAPS™ heteroconjugates disclosed herein, the antigen Peptide $P_2$ is covalently bound to ICBL Peptide $P_1$ or other immunomodulatory peptide having the capability to bind to molecules present on the surface of dendritic cells or monocytes. Once bound to the surface of a dendritic cell, the antigen Peptide $P_2$ can then be recognized by local T cell receptor (TCR) or Major Histocompatibility Complex (MHC) molecules to trigger a corresponding immune response and immune recognition of the antigen Peptide $P_2$. Through such a mechanism, a latter challenge with a competent Type A influenza virus will generate a secondary immune response in a subject previously administered one or more of the peptide constructs disclosed herein. Further, the LEAPS™ heteroconjugates described herein can be used to stimulate an immune response and increase survivability in subjects having an active infection such as with influenza virus.

In certain embodiments the Peptide $P_2$ can be derived from disease causing organism or agents, for example, viruses, bacteria, rickettsia or parasites. Example disease causing organisms, viruses, parasites, etc. include adenovirus, hepatitis C virus (HCV), hepatitis B virus (HBV), human papilloma virus (HPV), human T-lymphotropic virus 1 (HTLV-1), respiratory syncytial virus (RSV), vaccinia virus, West Nile virus (WNV), polyomavirus, human T-lymphotropic virus 2 (HTLV-2), cytomegalovirus (CVM), Epstein-Barr virus (EBV), Kaposi's sarcoma-associated herpes virus (HSV-VIII), varicella zoster virus (VZV), herpes simplex 1 virus (HSV-1), herpes simplex 2 virus (HSV-2), poliovirus type 3 included strains P3/LEON/37 and PS/LEON/12A[1]B, human polio virus 1 Mahoney, *tuberculosis*, Lyme disease (caused by bacteria *Borrelia burgdorferi*), stomach diseases caused by bacteria *Helicobacter pylori* (*H. pylori*), Chlamydia, malaria, and *Treponema pallidum*.

In the LEAPS™ heteroconjugates disclosed herein, the antigen Peptide $P_2$ is covalently bound to ICBL Peptide $P_1$ or other immunomodulatory peptide having the capability to bind to molecules present on the surface of dendritic cells or monocytes. Once bound to the surface of a dendritic cell, the antigen Peptide $P_2$ can then be recognized by local T cell receptor (TCR) or Major Histocompatibility Complex (MHC) molecules to trigger a corresponding immune response and immune recognition of the antigen Peptide $P_2$. Through such a mechanism, a latter challenge with a disease-causing agent will generate a secondary immune response in a subject previously administered one or more of the peptide constructs disclosed herein. Further, the LEAPS™ heteroconjugates described herein can be used to stimulate an immune response and increase survivability in subjects having an active infection.

A further aspect of the LEAPS™ heteroconjugates disclosed herein is that the extent of pro-inflammatory or inflammatory cytokines produced during the immune response to the peptide constructs is reduced relative to levels typically associated with larger antigen proteins containing many different epitope sequences. Further, a Th1 type of immune response or a Th2 type of immune response may be promoted based upon the identity of the ICBL Peptide $P_1$ conjugated with the antigen Peptide $P_2$.

A further aspect of the LEAPS™ heteroconjugates disclosed herein is that the heteroconjugates can be treated or contacted with dendritic cells isolated from a subject or donor under conditions where the dendritic cells differentiate into more matured immune cells capable of directing immunity toward influenza virus. The matured dendritic cells increase resistance against influenza infection when administered to the subject.

LEAPS™ Heteroconjugates

Specifically, the novel peptides of this invention include peptide constructs of the following Formulae (I) and (II):

$$P_1\text{-}x\text{-}P_2 \quad (I)$$

$$P_2\text{-}x\text{-}P_1 \quad (II)$$

where $P_2$ is a peptide derived with Type A influenza, which will bind to an antigen receptor on a set or subset of dendritic cells or T cells; $P_2$ is an immune response modifying peptide, which will cause a directed immune response by said set or subset of T cells or dendritic cells to which the peptide $P_1$ is attached and initiate an immune response focused on IL-12 without or with low levels of pro-inflammatory or inflammatory cytokines (Patricia R Taylor; Christopher A Paustian, Gary K Koski, Daniel H Zimmerman, K S Rosenthal, Maturation of dendritic cell precursors into IL12 producing DCs by J-LEAPS, *Cellular Immunology*, 2010; 262:1-5; Taylor P R, G K Koski, C C Paustian, P A Cohen, F B-G Moore, D H Zimmerman, K S Rosenthal, J-L.E.A.P.S.™ Vaccines Initiate Murine Th1 Responses By Activating Dendritic Cells, *Vaccine* 2010; 28:5533-4, both of which are incorporated herein by reference). As shown in Formulae (I) and (II), the Peptide $P_1$ can be N-terminal or C-terminal to the Peptide $P_2$.

In certain embodiments, the Peptide $P_1$ contains an ICBL termed "J" or "Peptide J." Peptide J is derived from amino acids 38-50 from the β-2-microglobulin chain of the MHC I molecule (DLLKNGERIEKVE) (SEQ ID No. 3). ICBL Peptide J is believed to promote Th1-type immune responses to the coupled antigen $P_2$ peptide, but is not limited to such activity.

In certain embodiments, the Peptide $P_1$ of the peptide constructs contains an ICBL termed "CEL-1000" (DGQEEKAGVVSTGLI) (SEQ ID No. 4). The CEL-1000 peptide is derived from the β-chain of MHC II (MHC II (3134-148) and binds to murine as well as human CD4+ cells. The chemical structure of conjugated peptides containing CEL-1000 can have an amidated carboxyl terminal, (amino)-DGQEEKAGVVSTGLI-(amide) (SEQ ID No. 5). CEL-1000 can be prepared by F-MOC chemistry and purified by Reverse Phase (RP)-HPLC, analyzed by another RP-PLC system, ion exchange chromatography (IEC)-HPLC as well as mass spectroscopy. Based on site directed mutagenesis studies of MHC II β-chain and/or peptide competition studies, peptides such as CEL-1000, were shown to bind to CD4, a T cell co-stimulator molecule (Charoenvit et al., A small peptide derived from human MHC β2 chain induces complete protection against malaria in an antigen-independent manner, Antimicrobial Agents and Chemotherapy, July 2004; 48(7):2455-63; Cammarota et al., Identification of a CD4 binding site on the beta 2 domain of HLA-DR molecules, Nature, 1992; 356:799-801) and cell surface protein on some Dendritic Cell (DCs) (Konig, et al., MHC class II interaction with CD4 medicated by a region analogous to the MHC class I binding site for CD8, Nature, 1992; 356:796-798; Shen X. and Konig R., "Regulation of T cell immunity and tolerance in vivo by CD4", Int. Immunol., 1998 10:247-57; Shen X. et al., Peptides corresponding to CD4-interacting regions of murine MHC class II molecules modulate immune responses of CD4+ T lymphocytes in vitro and in vivo, J Immunol., 1996; 157:87-100, all of which are incorporated herein by reference).

In certain embodiments, the Peptide $P_1$ contains an ICBL termed "G" or "Peptide G." Peptide G has the sequence NGQEEKAGVVSTGLI (SEQ ID No. 6) derived from the MHC-II beta 2 chain (Zimmerman et al., A new approach to T cell activation: natural and synthetic conjugates capable of activating T cells, 1996, Vacc. Res., 1996; 5:91, 5:102; Rosenthal et al., Immunization with a LEAPS™ heteroconjugate containing a CTL epitope and a peptide from beta-2-microglobulin elicits a protective and DTH response to herpes simplex virus type 1, 1999, Vaccine, 1999; 17(6): 535-542, both of which are incorporated herein by reference).

In certain embodiments, the Peptide $P_1$ contains an ICBL termed "IL-1β" or "Peptide IL-1β." Peptide IL-1β has the sequence VQGEESNDK (SEQ ID No. 40) derived from the human interleukin-1β chain (e.g., Bajpai et al., Immunomodulating activity of analogs of noninflammatory fragment 163-171 of human interleukin-lbeta 1998 Immunopharmacology, 38:237, incorporated herein by reference).

Novel epitope sequences that can serve as the antigen $P_2$ peptide and conjugated with the ICBL Peptide $P_1$ to form a LEAPS™ heteroconjugate will now be described. In certain embodiment, the Peptide $P_2$ is derived from nucleoprotein of the Type A influenza virus (NP-A), NDATYQRTRALVRTG (SEQ ID No. 7). In certain embodiments, the Peptide $P_2$ is derived from the matrix 2 ectodomain (M2e) of the A virus, SLLTEVETPIRNEWGCRCNDSSD (SEQ ID No. 8). In certain embodiments, the Peptide $P_2$ is derived from the hemagglutinin monomer 2 core 1 protein (HA2 core 1), GLFGAIAGFIEGG (SEQ ID No. 10). In certain embodiments, the Peptide $P_2$ is derived from the HA2 domain of the hemagglutinin protein (HA2 core 2), LKSTQNAIDE-ITNKVN (SEQ ID No. 9).

In certain embodiments, the novel epitope sequence is selected from one of SEQ ID No.'s 7-10. In some embodiments, the novel epitope sequences that can serve as the antigen $P_2$ peptide and conjugated with the ICBL Peptide $P_1$ to form a LEAPS™ heteroconjugate can be selected from YLEEHPSAGKDPKKTGGPIY (SEQ ID No. 41) from influenza nucleoprotein and TGTFEFTSFFYRYGFVANF (SEQ ID No. 43) from influenza polymerase protein 1 (PB1). In further embodiments, the novel epitope sequences that can serve as the antigen $P_2$ peptide can be selected from AQNAISTTFPYTGDPPY (SEQ ID No. 42), VERLKHGT-FGPVHFRNQVKI RR (SEQ ID No. 44), RNDDVDQSLI IAARNIVRRA (SEQ ID No. 45), HQLLRHFQKD AKVLF (SEQ ID No. 46). See Reference number 5 (Tan et al.) below.

A LEAPS™ heteroconjugate having immunomodulatory effects toward an infectious or other disease causing agent such as influenza virus is contemplated containing any combination of sequences selected from embodiments of Peptide $P_1$ and Peptide $P_2$ having the structure of one of Formulae (I) and (II), as described above. In Formulae (I) and (II), -x- represents a covalent bond or a divalent peptide linking group providing a covalent linkage between Peptide $P_1$ and Peptide $P_2$. In certain embodiments, -x- is a divalent peptide linking group having one or more glycine residues, such as the divalent linking group -GGG- or -GG-. In order to avoid synthesis of peptides having four glycine residues in a row, which may be difficult to synthesize, a linking group of -GG- can be used.

In certain embodiments, the divalent linking group is not limited to any particular identity so long as the linking group -x- serves to covalently attach the Peptide $P_1$ and Peptide $P_2$ as shown in Formulae (I) and (II). The linking group -x- can contain one or more amino acid residues or a bifunctional chemical linking group, such as, for example, N-succinimidyl-3-(2-pyridyldithio)propionate (SPDP), m-maleimidobenzoyl-N-hydroxy-succinimide ester (MBS), or 1-ethyl-3-(3-dimethylaminopropyl)carbodiimide (EDC). In certain embodiments, the linking group -x- can be a direct peptide or other covalent bond directly coupling Peptide $P_1$ and Peptide $P_2$. In certain embodiments where the linking group -x- contains amino acid residues, the linking group -x- can contain from 1 to about 5 amino acid residues or from 1 to about 3 amino residues. In certain embodiments, the linking group -x- can be cleavable or non-cleavable under physiological conditions.

The LEAPS™ heteroconjugates of Formulae (I) and (II) can be modified including modifications to the N- or C-terminal of the heteroconjugates. The LEAPS™ heteroconjugates described by Formulae (I) and (II) contain a sequence of amino acid residues consistent with the described Peptide $P_1$ and Peptide $P_2$. However, the N- or C-terminal of the described LEAPS™ heteroconjugates can be modified by any one or more of amidation or acylation, including myristoylation.

In certain embodiments, Peptides $P_1$ and $P_2$ include variants of any sequence disclosed herein. A variant is herein defined as a sequence wherein 1, 2, 3, 4 or 5 amino acid residues of sequence disclosed herein are replaced with a different amino acid residue without affecting the ability of the LEAPS™ heteroconjugates to stimulate an immune response against an infectious agent. In certain embodiment, variants have amino acid residues substituted in a conserved manner. In certain other embodiments, variants have amino acid residues substituted in a non-conserved manner. Variants include amino acid sequences where 1, 2, 3, 4 or 5 amino acid residues are deleted from the sequences and/or 1, 2, 3, 4 or 5 amino acid residues are added to the sequences. Variants include embodiments where combinations of conserved or non-conserved substitutions, additions and/or deletions are made to a sequence. In certain embodiments, Peptides $P_1$ and $P_2$ include variants of SEQ ID No.'s 1-36 and 41-52. A variant is herein defined as a sequence wherein 1, 2, 3, 4 or 5 amino acid residues of any of SEQ ID No.'s 1-36 and 41-52 or any other sequence disclosed herein are replaced with a different amino acid residue without affecting the ability of the LEAPS™ heteroconjugates to stimulate an immune response against Type A influenza virus. In certain embodiments, variants to SEQ ID No.'s 1-36 and 41-52 have amino acid residues substituted in a conserved manner. In certain other embodiments, variants to SEQ ID No.'s 1-36 and 41-52 or any other sequence disclosed herein have amino acid residues substituted in a non-conserved manner. Variants to SEQ ID No.'s 1-36 and 41-52 or any other sequence disclosed herein include amino acid sequences where 1, 2, 3, 4 or 5 amino acid residues are deleted from the sequences and/or 1, 2, 3 or 4 or 5 amino acid residues are added to the sequences. Variants include embodiments where combinations of conserved or non-conserved substitutions, additions and/or deletions are made to a sequence.

A conserved substitution is a substitution where an amino acid residue is replaced with another amino acid residue having similar charge, polarity, hydrophobicity, chemical functionality, size and/or shape. Substitution of an amino acid residue in any of the following groups with an amino acid residue from the same group is considered to be a conserved substitution: 1) Ala and Gly; 2) Asp and Glu; 3) Ile, Leu, Val and Ala; 4) Lys, Arg and His; 5) Cys and Ser; 6) Phe, Trp and Tyr; 7) Phe and Pro; 8) Met and Nle (norleucine); 9) Asn and Gln; and 10) Thr and Ser.

Table 1 shows exemplary LEAPS™ heteroconjugates consistent with Formulae (I) and (II), including permutations of constructs of CEL-1000, Peptide J and Peptide G (Peptides $P_1$) with the NP and M2e, HA2 core 1 and HA2 core 2 epitope peptides (Peptides $P_2$), as described above. Those skilled in the art will recognize that other constructs can be formed substituting for Peptide $P_1$ and Peptide $P_2$ where the examples on Table 1 are merely illustrative and are not limiting.

TABLE 1

| Exemplary LEAPS™ Heteroconjugates for Influenza virus | |
|---|---|
| DLLKNGERIEKVEGGGNDATYQRTRALVRTG | 1 |
| DLLKNGERIEKVEGGGSLLTEVETPIRNEWGCRCNDSSD | 2 |
| DLLKNGERIEKVEGGGLKSTQNAIDEITNKVN | 11 |
| DLLKNGERIEKVEGGGGLFGAIAGFIEGG | 12 |
| DGQEEKAGVVSTGLIGGGLKSTQNAIDEITNKVN | 13 |
| DGQEEKAGVVSTGLIGGGGLFGAIAGFIEGG | 14 |
| DGQEEKAGVVSTGLIGGGNDATYQRTRALVRTG | 15 |
| DGQEEKAGVVSTGLIGGGSLLTEVETPIRNEWGCRCNDSSD | 16 |
| LKSTQNAIDEITNKVNGGGDLLKNGERIEKVE | 17 |
| LKSTQNAIDEITNKVNGGGDGQEEKAGVVSTGLI | 18 |
| GLFGAIAGFIEGGGGDLLKNGERIEKVE | 19 |
| GLFGAIAGFIEGGGGDGQEEKAGVVSTGLI | 20 |
| SLLTEVETPIRNEWGCRCNDSSDGGGDLLKNGERIEKVE | 21 |
| SLLTEVETPIRNEWGCRCNDSSDGGGDGQEEKAGVVSTGLI | 22 |
| NDATYQRTRALVRTGGGGDLLKNGERIEKVE | 23 |
| NDATYQRTRALVRTGGGGDGQEEKAGVVSTGLI | 24 |
| DLLKNGERIEKVEGGGLFGAIAGFIEGG | 25 |
| DGQEEKAGVVSTGLIGGGLFGAIAGFIEGG | 26 |
| NDATYQRTRALVRTGGGDLLKNGERIEKVE | 27 |
| NDATYQRTRALVRTGGGDGQEEKAGVVSTGLI | 28 |
| NGQEEKAGVVSTGLIGGGNDATYQRTRALVRTG | 29 |
| NGQEEKAGVVSTGLIGGGSLLTEVETPIRNEWGCRCNDSSD | 30 |
| NGQEEKAGVVSTGLIGGGLKSTQNAIDEITNKVN | 31 |
| NDATYQRTRALVRTGNGQEEKAGVVSTGLI | 32 |
| SLLTEVETPIRNEWGCRCNDSSDNGQEEKAGVVSTGLI | 33 |
| LKSTQNAIDEITNKVNNGQEEKAGVVSTGLI | 34 |
| GLFGAIAGFIEGGGDLLKNGERIEKVE | 35 |
| GLFGAIAGFIEGGGDGQEEKAGVVSTGLI | 36 |
| DLLKNGERIEKVEGGGYLEEHPSAGKDPKKTGGPIY | 47 |
| DLLKNGERIEKVEGGGAQNAISTTFPYTGDPPY | 48 |
| DLLKNGERIEKVEGGGTGTFEFTSFFYRYGFVANF | 49 |
| DLLKNGERIEKVEGGGVERLKHGTFGPVHFRNQVKIRR | 50 |

TABLE 1-continued

Exemplary LEAPS™ Heteroconjugates for Influenza virus

| | |
|---|---|
| DLLKNGERIEKVEGGGRNDDVDQSLIIAARNIVRRA | 51 |
| DLLKNGERIEKVEGGGHQLLRHFQKDAKVLF | 52 |

Table 1 presents exemplary LEAPS™ heteroconjugates using antigens (Peptide $P_2$) derived from Type A influenza virus. Table 2 presents antigen sequences, either as a core epitope or as an extended region, useful for making LEAPS™ heteroconjugates, along with other information and references about these epitopes. Further, LEAPS™ heteroconjugates incorporating an antigen sequence from Table 2, including antigens derived from Type A influenza, can be used to treat DCs to form matured DCs ex vivo, as will be described below. Such LEAPS™ heteroconjugate-treated DCs can be transferred to a subject to confer resistance, immunity, or to treat an active or acute infection caused by an influenza virus. Such LEAPS™ heteroconjugate-treated DCs also have the unexpected property to localize in a region of the body where a source of antigen originating from an influenza virus can be found.

Table 2 shows exemplary antigens described that can be employed as peptide $P_2$ in certain embodiments. LEAPS™ heteroconjugates consistent with Formulae (I) and (II) can be formed by combining any permutation of ICBL peptide including, but not limited to, CEL-1000, Peptide J and/or Peptide G (Peptides $P_1$) with an antigen peptide (Peptide $P_2$) as presented in Table 2. Specifically, the first column of Table 2 lists the SEQ ID No. for the sequence presented in each row. The second column specifies the protein from which the individual amino acid sequences are derived. The third column gives the abbreviation for which the sequence presented in each row can be referred to. Also provided on Table 2 are example LEAPS™ heteroconjugates where Peptide $P_1$ is Peptide J (SEQ ID No. 3) combined with an antigen Peptide $P_2$. The fourth column specifies the core epitope sequence, if any, for the protein described in each row, and the fifth column specifies an extended epitope sequence associated with the protein described in each row. The sixth column indicates the range of amino acids from the described protein corresponding to the epitope sequence. The seventh column presents a non-limiting example LEAPS™ heteroconjugate containing Peptide J. The eighth column lists any know references describing the extended or core epitope sequences, if known. References are specified by a number corresponding to the list of references found at the end of this disclosure.

TABLE 2

Influenza antigen sequences and example LEAPS™ heteroconjugates

| Seq ID No. | Protein Candidates | Abbreviation | Core Epitope | Extended region |
|---|---|---|---|---|
| 7 | Nucelo protein | NP1 | NA | NA |
| 1 | | J-NP1 | NA | NDATYQRTRALVRTG |
| 8 | Matrix 2 e (ectodomain protein | M2e | | NA |
| 2 | | J-M2e | NA | SLLTEVETPIRNEWGCRCNDSSD |
| 10 | Hemagglutin protein | HA2-1 | | NA |
| 12 | | HA2-1 fus | NA | GLFGAIAGFIEGG |
| | | J-HA1 | NA | |
| 9 | Hemagglutin protein | HA2-2 | | NA |
| 11 | | J-HA2 | NA | LKSTQNAIDEITNKVN |
| 41 | Nucleoprotein | NP78 | NA | YLEEHPSAGKDPKKTGGPIY |
| 47 | | J-NP78 | | |
| 42 | Polymerase B1 | PB1-14 | NA | AQNAISTTFPYTGDPPY |
| 48 | | J-PB1-14 | NA | |
| 43 | Polymerase B1 | PB1-487 | NA | TGTFEFTSFFYRYGFVANF |
| 49 | | J-PB1-487 | NA | |
| 44 | Polymerase B2 | PB2-122 | | VERLKHGTFGPVHFRNQVKIRR |
| 50 | | J-PB2-122 | NA | |
| 45 | Polymerase B2 | PB2-251 | NA | RNDDVDQSLIIAARNIVRRA |
| 51 | | J-PB2-251 | NA | |

TABLE 2-continued

Influenza antigen sequences and example LEAPS™ heteroconjugates

| | | | | |
|---|---|---|---|---|
| 46 | Polymerase B2 | PB2-432 | NA | HQLLRHFQKDAKVLF |
| 52 | | J-PB2-432 | NA | |

| Seq ID No. | Amino Acid | J LEAPS Conjugate | Ref. |
|---|---|---|---|
| | | NA | 1 |
| 7 | 144-161 | NA | |
| 1 | NA | DLLKNGERIEKVEGGGNDATYQRTRALVRTG | |
| | | NA | 2 |
| 8 | 1-23 | NA | |
| 2 | NA | DLLKNGERIEKVEGGGSLLTEVETPIRNEWGCRCNDSSD | |
| | | NA | 3 |
| 10 | | NA | |
| 12 | NA | DLLKNGERIEKVEGGGGLFGAIAGFIEGG | |
| | | NA | 4 |
| 9 | | NA | |
| 11 | NA | DLLKNGERIEKVEGGGLKSTQNAIDEITNKVN | |
| 41 | 78-97 | | 5 |
| 47 | NA | DLLKNGERIEKVEGGGYLEEHPSAGKDPKKTGGPIY | |
| 42 | 14-30 | | 5 |
| 48 | NA | DLLKNGERIEKVEGGGAQNAISTTFPYTGDPPY | |
| 43 | 487-505 | | 5 |
| 49 | NA | DLLKNGERIEKVEGGGTGTFEFTSFFYRYGFVANF | |
| 44 | 122-143 | | 5 |
| 50 | | DLLKNGERIEKVEGGGVERLKHGTFGPVHFRNQVKIRR | |
| 45 | 251-270 | | 5 |
| 51 | | DLLKNGERIEKVEGGGRNDDVDQSLIIAARNIVRRA | |
| 46 | 432-446 | | 5 |
| 52 | | DLLKNGERIEKVEGGGHQLLRHFQKDAKVLF | |

Table 3 shows exemplary LEAPS™ heteroconjugates consistent with Formulae (I) and (II), including exemplary LEAPS™ heteroconjugates formed by linking Peptide J to various infectious disease antigens in addition to Influenza virus. Those skilled in the art will recognize that other constructs can be formed substituting for Peptide $P_1$ and Peptide $P_2$ where the examples on Table 3 are merely illustrative and are not limiting.

Table 3 present antigen sequences, either as a core epitope or as an extended region, useful for making LEAPS™ heteroconjugates. The antigen sequences useful as serving as Peptide $P_2$ in Formulae (I) and (II), described above, are derived from several viruses, bacteria and parasites including adeno-virus, hepatitis C virus (HCV), hepatitis B virus (HBV), human papilloma virus (HPV), human T-lymphotropic virus 1 (HTLV-1), respiratory syncytial virus (RSV), vaccinia virus, West Nile virus (WNV), polyomavirus, human T-lymphotropic virus 2 (HTLV-2), cytomegalovirus (CMV), Epstein-Barr virus (EBV), Kaposi's sarcoma-associated herpes virus (HSV-VIII), varicella zoster virus (VZV), herpes simplex 1 virus (HSV-1), herpes simplex 2 virus (HSV-2), poliovirus type 3 included strains P3/LEOM/37 and PS/LEON/12A[1]B, human polio virus 1 Mahoney, *tuberculosis*, Lyme disease, Chlamydia, malaria, *Helicobacter pylori* (*H. pylori*) for stomach diseases and ulcers, and *Borrelia burgdorferi* (*B. burgdorferi*) causing Lyme disease and *Treponema pallidum*. The antigen sequences described on Table 3 are useful for forming LEAPS™ heteroconjugates that can confer increase resistance or immunity to the viruses, bacteria or parasites from which the specific antigen sequences originate, or can be used to treat an active or acute infection in a subject.

Further, LEAPS™ heteroconjugates incorporating an antigen sequence from Tables 1 and 3, including antigens can be used to treat DCs to form matured DCs ex vivo, as will be described below. Such LEAPS™ heteroconjugate-treated DCs can be transferred to a subject to confer resistance, immunity or to treat an active or acute infection caused by a virus, bacteria or parasite. Such LEAPS™ heteroconjugate-treated DCs also have the unexpected property to localize in a region of the body where a source of antigen originating from a virus, bacteria or parasite can be found. Many disease causing substances and organisms, including bacteria, can be present in the body in a quiescent phase or condition that does not cause any active symptoms. In particular, certain viruses can even be incorporated into the host genome with a period of years or decades between expression or have very low levels of antigen expression. For example, HSV-I, HSV-II, EBV, CMV, VZV, HSV-VI, HSV-VIII, polio, HTLV-I, HTLV-II, Human immunodeficiency virus (HIV), mumps, RSV and perhaps *H. pylori* and *B. burgdorferi* are suspected to have the capability to enter a long-term quiescent phase with the possibility of later emergence of symptoms or lower level of activity. As will be described in the Examples, LEAPS™ heteroconjugate-treated DCs have the capability to localize to location where sources of antigen can be found. As such, LEAPS™ heteroconjugate-treated DCs can be used to diagnose the presence of viruses that are in a quiescent phase and otherwise difficult to detect.

In certain embodiments, a LEAPS™ heteroconjugate in accordance to Formulae (I) or (II) incorporates any of SEQ ID No.'s 53-56 to form a heteroconjugate capable of modulating an immune response to Adeno-virus or to mature DCs having the capability to modulate an immune response to Adeno-virus. Exemplary LEAPS™ heteroconjugates specific to Adeno-virus include, but are not limited to, SEQ ID No.'s 140-141.

In certain embodiments, a LEAPS™ heteroconjugate in accordance to Formulae (I) or (II) incorporates any of SEQ ID No.'s 57-60 to form a heteroconjugate capable of modulating an immune response to hepatitis C virus or to mature DCs having the capability to modulate an immune response to hepatitis C virus. Exemplary LEAPS™ heteroconjugates specific to hepatitis C virus include, but are not limited to, SEQ ID No.'s 142-143.

In certain embodiments, a LEAPS™ heteroconjugate in accordance to Formulae (I) or (II) incorporates any of SEQ ID No.'s 61-64 to form a heteroconjugate capable of modulating an immune response to hepatitis B virus or to mature DCs having the capability to modulate an immune response to hepatitis B virus. Exemplary LEAPS™ heteroconjugates specific to hepatitis B virus include, but are not limited to, SEQ ID No.'s 144-146.

In certain embodiments, a LEAPS™ heteroconjugate in accordance to Formulae (I) or (II) incorporates any of SEQ ID No.'s 65-66 to form a heteroconjugate capable of modulating an immune response to human papilloma virus or to mature DCs having the capability to modulate an immune response to human papilloma virus. An exemplary LEAPS™ heteroconjugates specific to human papilloma virus includes, but is not limited to, SEQ ID No. 147.

In certain embodiments, a LEAPS™ heteroconjugate in accordance to Formulae (I) or (II) incorporates any of SEQ ID No.'s 67-68 to form a heteroconjugate capable of modulating an immune response to HTLV-1 or to mature DCs having the capability to modulate an immune response to HTLV-1 virus. An Exemplary LEAPS™ heteroconjugates specific to HTLV-1 includes, but is not limited to, SEQ ID No. 148.

In certain embodiments, a LEAPS™ heteroconjugate in accordance to Formulae (I) or (II) incorporates any of SEQ ID No.'s 69-70 to form a heteroconjugate capable of modulating an immune response to RSV or to mature DCs having the capability to modulate an immune response to RSV. An exemplary LEAPS™ heteroconjugate specific to RSV includes, but is not limited to, SEQ ID No. 149.

In certain embodiments, a LEAPS™ heteroconjugate in accordance to Formulae (I) or (II) incorporates any of SEQ ID No.'s 71-72 to form a heteroconjugate capable of modulating an immune response to vaccinia virus or to mature DCs having the capability to modulate an immune response to vaccinia virus. An exemplary LEAPS™ heteroconjugate specific to vaccinia virus includes, but is not limited to, SEQ ID No. 150.

In certain embodiments, a LEAPS™ heteroconjugate in accordance to Formulae (I) or (II) incorporates any of SEQ ID No.'s 73-74 to form a heteroconjugate capable of modulating an immune response to West Nile virus or to mature DCs having the capability to modulate an immune response to West Nile virus. An exemplary LEAPS™ heteroconjugate specific to West Nile virus includes, but is not limited to, SEQ ID No. 151.

In certain embodiments, a LEAPS™ heteroconjugate in accordance to Formulae (I) or (II) incorporates any of SEQ ID No.'s 75-80 to form a heteroconjugate capable of modulating an immune response to polyomavirus or to mature DCs having the capability to modulate an immune response to polyomavirus. Exemplary LEAPS™ heteroconjugates specific to polyomavirus include, but are not limited to, SEQ ID No.'s 152-154.

In certain embodiments, a LEAPS™ heteroconjugate in accordance to Formulae (I) or (II) incorporates any of SEQ ID No.'s 81-82 to form a heteroconjugate capable of modulating an immune response to HTLV-2 or to mature DCs having the capability to modulate an immune response to HTLV-2. An exemplary LEAPS™ heteroconjugate specific to HTLV-2 includes, but is not limited to, SEQ ID No. 155.

In certain embodiments, a LEAPS™ heteroconjugate in accordance to Formulae (I) or (II) incorporates any of SEQ ID No.'s 83-86 to form a heteroconjugate capable of modulating an immune response to cytomegalovirus or to mature DCs having the capability to modulate an immune response to cytomegalovirus. Exemplary LEAPS™ heteroconjugates specific to cytomegalovirus include, but are not limited to, SEQ ID No.'s 156-157.

In certain embodiments, a LEAPS™ heteroconjugate in accordance to Formulae (I) or (II) incorporates any of SEQ ID No.'s 87-90 to form a heteroconjugate capable of modulating an immune response to EBV or to mature DCs having the capability to modulate an immune response to EBV. Exemplary LEAPS™ heteroconjugates specific to EBV include, but are not limited to, SEQ ID No.'s 158-159.

In certain embodiments, a LEAPS™ heteroconjugate in accordance to Formulae (I) or (II) incorporates any of SEQ ID No.'s 91-99 to form a heteroconjugate capable of modulating an immune response to HSV-VIII or to mature DCs having the capability to modulate an immune response to HSV-VIII. Exemplary LEAPS™ heteroconjugates specific to HSV-VIII include, but are not limited to, SEQ ID No.'s 160-165.

In certain embodiments, a LEAPS™ heteroconjugate in accordance to Formulae (I) or (II) incorporates any of SEQ ID No.'s 100-114 to form a heteroconjugate capable of modulating an immune response to VZV or to mature DCs having the capability to modulate an immune response to VZV. Exemplary LEAPS™ heteroconjugates specific to VZV include, but are not limited to, SEQ ID No.'s 166-173.

In certain embodiments, a LEAPS™ heteroconjugate in accordance to Formulae (I) or (II) incorporates any of SEQ ID No.'s 115-120 to form a heteroconjugate capable of modulating an immune response to HSV-1 or to mature DCs having the capability to modulate an immune response to HSV-1. Exemplary LEAPS™ heteroconjugates specific to HSV-1 include, but are not limited to, SEQ ID No.'s 174-176.

In certain embodiments, a LEAPS™ heteroconjugate in accordance to Formulae (I) or (II) incorporates any of SEQ ID No.'s 121-124 to form a heteroconjugate capable of modulating an immune response to HSV-2 or to mature DCs having the capability to modulate an immune response to HSV-2. Exemplary LEAPS™ heteroconjugates specific to HSV-2 include, but are not limited to, SEQ ID No.'s 177-178.

In certain embodiments, a LEAPS™ heteroconjugate in accordance to Formulae (I) or (II) incorporates any of SEQ ID No.'s 125-126 to form a heteroconjugate capable of modulating an immune response to herpes simplex virus or to mature DCs having the capability to modulate an immune response to herpes simplex virus. An exemplary LEAPS™ heteroconjugate specific to herpes simplex virus includes, but is not limited to, SEQ ID No. 179.

In certain embodiments, a LEAPS™ heteroconjugate in accordance to Formulae (I) or (II) incorporates SEQ ID No. 127 to form a heteroconjugate capable of modulating an immune response to EBV (Epstein-Barr virus) or to mature DCs having the capability to modulate an immune response to EBV. An Exemplary LEAPS™ heteroconjugate specific to poliovirus type 3 include, but are not limited to, SEQ ID No. 180.

In certain embodiments, a LEAPS™ heteroconjugate in accordance to Formulae (I) or (II) incorporates any of SEQ ID No.'s 128-129 to form a heteroconjugate capable of modulating an immune response to polio virus type 3 or to mature DCs having the capability to modulate an immune response to polio virus type 3. Exemplary LEAPS™ heteroconjugates specific to poliovirus type 3 include, but are not limited to, SEQ ID No.'s 181-182.

In certain embodiments, a LEAPS™ heteroconjugate in accordance to Formulae (I) or (II) incorporates SEQ ID No. 130 to form a heteroconjugate capable of modulating an immune response to human poliovirus 1 Mahoney or to mature DCs having the capability to modulate an immune response to human polio virus 1 Mahoney. An exemplary LEAPS™ heteroconjugate specific to human polio virus 1 Mahoney includes, but is not limited to, SEQ ID No. 183.

In certain embodiments, a LEAPS™ heteroconjugate in accordance to Formulae (I) or (II) incorporates any of SEQ ID No.'s 131-133 and 190-193 to form a heteroconjugate capable of modulating an immune response to *tuberculosis* or to mature DCs having the capability to modulate an immune response to *tuberculosis*. Exemplary LEAPS™ heteroconjugates specific to *tuberculosis* include, but are not limited to, SEQ ID No.'s 184-185 and 209-210.

In certain embodiments, a LEAPS™ heteroconjugate in accordance to Formulae (I) or (II) incorporates any of SEQ ID No.'s 134 and 194-195 to form a heteroconjugate capable of modulating an immune response to Lyme disease or to mature DCs having the capability to modulate an immune response to Lyme disease. Exemplary LEAPS™ heteroconjugates specific to Lyme disease includes, but is not limited to, SEQ ID No.'s 186 and 211.

In certain embodiments, a LEAPS™ heteroconjugate in accordance to Formulae (I) or (II) incorporates any of SEQ ID No.'s 135-136 to form a heteroconjugate capable of modulating an immune response to Chlamydia or to mature DCs having the capability to modulate an immune response to Chlamydia. An exemplary LEAPS™ heteroconjugate specific to Chlamydia virus includes, but is not limited to, SEQ ID No. 187.

In certain embodiments, a LEAPS™ heteroconjugate in accordance to Formulae (I) or (II) incorporates any of SEQ ID No.'s 137-138 to form a heteroconjugate capable of modulating an immune response to malaria or to mature DCs having the capability to modulate an immune response to malaria. An exemplary LEAPS™ heteroconjugate specific to malaria virus includes, but is not limited to, SEQ ID No. 188.

In certain embodiments, a LEAPS™ heteroconjugate in accordance to Formulae (I) or (II) incorporates any of SEQ ID No. 139 to form a heteroconjugate capable of modulating an immune response to *Treponema pallidum* or to mature DCs having the capability to modulate an immune response to *Treponema pallidum*. An exemplary LEAPS™ heteroconjugate specific to *Treponema pallidum* includes, but is not limited to, SEQ ID No. 189.

In certain embodiments, a LEAPS™ heteroconjugate in accordance to Formulae (I) or (II) incorporates any of SEQ ID No.'s 205-208 to form a heteroconjugate capable of modulating an immune response to *H. pylori* or to mature DCs having the capability to modulate an immune response to *H. pylori*. An exemplary LEAPS™ heteroconjugate specific to *H. pylori* includes, but is not limited to, SEQ ID No.'s 217-218.

In certain embodiments, a LEAPS™ heteroconjugate in accordance to Formulae (I) or (II) incorporates any of SEQ ID No.'s 196-204 to form a heteroconjugate capable of modulating an immune response to HIV or to mature DCs having the capability to modulate an immune response to HIV. An exemplary LEAPS™ heteroconjugate specific to HIV, includes, but is not limited to, SEQ ID No.'s 212-216.

Table 3 below shows exemplary antigens described that can be employed as peptide $P_2$ in certain embodiments. LEAPS™ heteroconjugates consistent with Formulae (I) and (II) can be formed by combining any permutation of ICBL peptide including, but not limited to, CEL-1000, Peptide J and/or Peptide G (Peptides $P_1$) with an antigen peptide (Peptide $P_2$) as presented in Table 3. Table 3 lists antigen sequences grouped by disease causing organism or agent associated with such sequences. Specifically, the first column of Table 3 lists the SEQ ID No. for the sequence presented in each row. The second column lists the disease, agent or organism for which the sequences presented in each row relate. The third column specifies the protein from which individual amino acid sequences are derived. The fourth column gives the abbreviation for which the sequence presented in each row can be referred to. For example, AH51ext stands for adenovirus 5 hexon protein (extended sequence), whereas J-AH51ext indicates a LEAPS™ heteroconjugate having the ICBL Peptide J linked to AH51ext. Also provided on Table 3 are example LEAPS™ heteroconjugates where Peptide $P_1$ is Peptide J (SEQ ID No. 3) combined with an antigen Peptide $P_2$. The fifth column specifies the core epitope sequence, if any, for the protein described in each row, and the sixth column specifies an extended epitope sequence associated with the protein described in each row. The seventh column indicates the range of amino acids from the described protein corresponding to the epitope sequence. The eighth column presents a non-limiting example LEAPS™ heteroconjugate containing Peptide J. The ninth column lists any know references describing the extended or core epitope sequences, if known. References are specified by a number corresponding to the list of references found at the end of this disclosure.

TABLE 3

Antigen Sequences for Peptide P₂ and Example LEAPS™ Heteroconjugates

| Seq ID No. | Disease or agent | Protein Candidates | Abbreviation | Core epitope | Extended region |
|---|---|---|---|---|---|
| 53 | Adeno-virus | Adenovirus 5 | AH51 | TDLGQNLLY | NA |
| 54 | | Hexon | AH51ext | NA | SMGALTDLGQNLLYANSAH |
| 140 | | | J-AH51ext | NA | |
| 55 | Adeno-virus | Adenovirus 5 | AH52 | TYFSLNNKF | NA |
| 56 | | Hexon | AH52ext | NA | ARATETYFSLNNKFRNPTV |
| 141 | | | J-AH52ext | NA | |
| 57 | Hepatitis C | E1 Protein | E1 | DLMGYIPAV | NA |
| 58 | Virus | | E1ext | NA | TCGFADLMGYIPAVGAPLG |
| 142 | | | J-E1ext | NA | |
| 59 | Hepatitis C | NS3 | NS3 | AYSQQTRGL | NA |
| 60 | Virus | | NS3ext | NA | LAPITAYSQQTRGLLGCII |
| 143 | | | J-NS3ext | NA | |
| 61 | Hepatitis B | S Protein | HBS | FLLTRILTI | NA |
| 62 | Virus | | HBS ext | NA | LQAGFFLLTRILTIPQSLD |
| 144 | | | J-HBSext | NA | |
| 63 | Hepatitis B | S Protein | HBS | NA | LRGDLQVLAQKVARTL |
| 145 | Virus | | J-HBS | NA | |
| 64 | Hepatitis B | pre S Protein | preHBS | NA | DYQGMLPVCPLIPGSSTTSTGPC |
| | Virus | | | | |
| 146 | | | J-HBSext | NA | |
| 65 | Human papillo | E7 | HPV16_E7 | YMLDLQPETT | |
| 66 | mavirus | | HPV16_E7ext | NA | PTLHEYMLDLQPETTDLYCY |
| 147 | | | J-HPV16_E7 | NA | |
| 67 | HTLV 1- | Tax-1 protein | HTLV_Tax1 | LLFGYPVYV | |
| 68 | Human T- | | HTLV_Tax1ext | NA | GFGQSLLFGYPVYVEGDCV |
| 148 | lymphotropic | | J-HTLV_Tax1 | NA | |
| 69 | RSV- | NP | RSV NP | KMLKEMGEV | |
| 70 | Respiratory | | RSV NPext | NA | RKSYKKMLKEMGEVAPEYR |
| 149 | Syncytial Virus | | J-RSV NP | NA | |
| 71 | Vaccinia Virus | Vaccinia virus | VACV_C7L | KVDDTFYYV | |
| 72 | | Host range | VACV_C7Lext | NA | VKVNKVDDTFYYVIYEAV |
| | | protein 2 74-82 | | | |
| 150 | | | J-VACV_C7L | NA | |
| 73 | West Nile | WNV NY-99 | WNVPP | RLDDDGNFQL | |
| | Virus | polyprotein | | | |
| 74 | | precursor | WNVPPext | NA | ERVDVRLDDDGNFQLMNDPG |
| | | (1452-1461) | | | |
| 151 | | | J-WNVPPext | NA | |
| 75 | Polyomavirus | VP1 | VP1A | SITEVECFL | NA |
| 76 | (JC/BK) | | VP1Aext | NA | KTGVDSITEVECFLTPEMG |
| 152 | | | J-VP1Aext | NA | |
| 77 | Polyomavirus | VP1 | VP1B | LLMWEAVTV | NA |
| 78 | (JC/BK) | | VP1Bext | NA | LTCGNLLMWEAVTVKTEVL |
| 153 | | | J-VP1Bext | NA | |
| 79 | Polyomavirus | Large T Antigen | LTA | LLLIWFRPV | NA |
| 80 | (JC/BK) | | LTAext | NA | GMTLLLLIWFRPVADFAT |
| 154 | | | J-LTAext | NA | |
| 81 | HTLV-2 | Tax | Tax1 | LLYGYPVYV | NA |
| 82 | | | Tax1ext | NA | GFGQSLLYGYPVYVFGDCV |
| 155 | | | J-PP65ext | NA | |
| 83 | Cytomegalo- | Regulatory | IE1 | VLAELVKQI | NA |
| 84 | virus | protein IE1 | IE1 ext | NA | NPEKDVLAELVKQIKVRVD |
| 156 | | | J-IE1ext | NA | |
| 85 | Cytomegalo- | Tegument | PP65 | QYDPVAALF | NA |
| 86 | virus | protein pp65 | PP65ext | NA | TVELRQYDPVAALFFFDID |
| 157 | | | J-PP65ext | NA | |

TABLE 3-continued

Antigen Sequences for Peptide P$_2$ and Example LEAPS™ Heteroconjugates

| | | | | | |
|---|---|---|---|---|---|
| 87 | Epstein Barr | Latent | LMP2 | FLYALALLL | NA |
| 88 | Virus | Membrane | LMP2ext | NA | LLARLFLYALALLLLASAL |
| 158 | | Protein 2A | J-LMP2ext | NA | |
| 89 | Epstein Barr | Latent | LMPA | PYLFWLAAI | NA |
| 90 | Virus | Membrane | LMPAext | NA | PVIVAPYLFWLAAIAASCF |
| 159 | | Protein 2A | J-LMPAext | NA | |
| 91 | KSHV | Kaposin | Kap1 | VLLNGWRWRL | NA |
| 92 | (HSV-VIII) | | Kap1ext | NA | VHVPDVLLNGWRWRLGAIPP |
| 160 | | | J-Kap1ext | NA | |
| 93 | KSHV | K1 Glycoprotein | gK1 | HRQSIWITW | NA |
| 94 | (HSV-VIII) | | gK1ext | NA | VEQSGHRQSIWITWITTQPV |
| 161 | | | JgK1ext | NA | |
| 95 | KSHV | Kaposin | Kap2 | LVCLLAISVVPPSGQ | NA |
| 162 | | | J-Kap2ext | NA | |
| 96 | KSHV | K8.1 | gK8-1 | ELTDALISAFSGSYS | NA |
| | | Glycoprotein | | | |
| 163 | | | J-gK8-1ext | NA | |
| 97 | KSHV | K8.1 | gK8-2 | LILYLCVPRCRRKKP | NA |
| | | Glycoprotein | | | |
| 164 | | | J-gK8-2ext | NA | |
| 98 | KSHV | ORF 57 | O57 | ISARGQELF | NA |
| 99 | (HSV-VIII) | | O57ext | NA | QSRRSISARGQELFRTLLE |
| 165 | | | J-O57ext | NA | |
| 100 | VZV | Glycoprotein B (II) | gP2A | EITDTIDKFGK | |
| 101 | | | gP2Aext | NA | PIPVSEITDTIDKFGKCSSKA |
| 166 | | | J-gP2Aext | NA | |
| 102 | VZV | Glycoprotein B (II) | gP2B | LPEGMDPFAEK | NA |
| 103 | | | gP2Bext | NA | KGLKQLPEGMDPFAEKPNATD |
| 167 | | | J-gP2Bext | NA | |
| 104 | VZV | Glycoprotein I | gP1A | ARLCDLPATPK | NA |
| 105 | | | gP1Aext | NA | ALFQQARLCDLPATPKGSGTS |
| 168 | | | JgP1Aext | NA | |
| 106 | VZV | Glycoprotein I | gP1B | PHSVVNPFVK | NA |
| 107 | | | gP1Bext | NA | REESPPHSVVNPFVK |
| 169 | | | JgP1Bext | NA | |
| 108 | VZV | IE62 | IE1 | SLPRSRTPI | NA |
| 109 | | | IE1ext | NA | RQKSFSLPRSRTPIIPPVS |
| 170 | | | J-IE1ext | NA | |
| 110 | VZV | IE62 | IE2 | SAPLPSNRV | NA |
| 111 | | | IE2ext | NA | SPWPGSAPLPSNRVRFGPS |
| 171 | | | JIE2ext | NA | |
| 112 | VZV | IE62 | IE3 | ALWALPHAA | NA |
| 113 | | | IE3ext | NA | MATGEALWALPHAAAAVAM |
| 172 | | | JIE3ext | NA | |
| 114 | VZV | DNA binding protein | VDNAP | PIRHNGITMEM | NA |
| 173 | | | J-VDNAP | NA | |
| 115 | HSV-1 | glyco protein D | gDI77 | SLPITVYYA | PFQPPSLPITVYYAVLERA |
| 116 | | | gDI77 ext | | |
| 174 | | | J-gDI77ext | | |
| 117 | HSV-1 | glyco protein D | gDI94 | VLLNAPSEA | RACRSVLLNAPSEAPQIVR |
| 118 | | | gD94ext | | |
| 175 | | | J-gD94ext | | |
| 119 | HSV-1 | glyco protein D | gD302 | ALLEDPVGT | DPEDSALLEDPVGTVAPQI |
| 120 | | | gD302ext | | |
| 176 | | | J-gD302ext | | |

TABLE 3-continued

Antigen Sequences for Peptide P₂ and Example LEAPS™ Heteroconjugates

| | | | | | |
|---|---|---|---|---|---|
| 121 | HSV-2 | glycoprotein B | gB II439 | GFLLAYQPLL | |
| 122 | | | gBII 2 ext | | YLATGGFLIAYQPLLSNTLA |
| 177 | | | J-gB2 ext | | |
| 123 | HSV-2 | tegument protein VP13/14 | Teg1 | GLADTVVAC | |
| 124 | | | Teg1ext | | RLHPHSAHPAFADVEQEAL |
| 178 | | | J-Teg1ext | | |
| 125 | HSV | gC | gC | DRRDPLARYGSR | NA |
| 126 | | | gCext | | GPVWCDRRDPLARYGSRVQIRC |
| 179 | | | J-gC | NA | |
| 127 | EBV | | p85 | CSLEREDRDAWHLPAYK | NA |
| 180 | | | J-p85 | NA | |
| 128 | Poliovirus type 3 (strains P3/LEON/37 AND P3/LEON 12A[1]B) | Genome polyprotein | PV-gpp1 | QPTTRAQKLFAMWRITYKDTV | |
| 181 | | | J-PVgpp1 | NA | |
| 129 | Poliovirus type 3 (strains P3/LEON/37 AND P3/LEON 12A[1]B) | Genome polyprotein | PV-gpp2 | VAIIEVDNEQPTTRAQKLFAM | |
| 182 | | | J-PVgpp2 | | |
| 130 | Human poliovirus 1 Mahoney | coat protein VP1 | VP1cp | SIFYTYGTAPARISVPYVGI | |
| 183 | | | J-VP1cp | | |
| | Tuberculosis | ESAT 6 | | | |
| 131 | | | ESAT6 | EQQWNFAGIEAAA | |
| 184 | | | J-ESAT6 | NA | |
| 190 | Tuberculosis | Antigen 85-B | 85-B | KLVANNTRL | |
| 191 | | | 85-Bext | NA | TQQIPKLVANNTRLWVYCG |
| 209 | | | J-85-Bext | NA | |
| 132 | Tuberculosis | Mycobacterium bovis antigen 85-A 6 | Mbovis85A | GLPVEYLQV | |
| 133 | | | Mbovis85Aext | NA | MFSRPGLPVE YLQVPSASM |
| 185 | | | J-Mbovis85A | NA | |
| 192 | Tuberculosis | Lipoprotein IpqH precursor | IpqH | VLTDGNPPEV | |
| 193 | | | IpqHext | NA | TGIAAVLTDGNPPEVKSVGL |
| 210 | | | J-IpqHext | NA | NA |
| 134 | Lyme disease | OMP | LOMP1 | | MKKDNIAAMVLRGMAK |
| | | | | NA | |
| 186 | | | J-LOMP1 | NA | |
| 194 | Lyme disease | Outer surface protein A precursor | LOMP2 | KSYVLEGTLTAE | |
| 195 | | | LOMP2ext | NA | GSGKAKEVLKSYVLEGTLTAEKT TLVVKEG |
| 211 | | | J-LOMP2ext | NA | |
| 135 | Chlamydia | Major Outer Membrane Protein | MOMP | RLNMFTPYI | NA |
| 136 | | | MOMP ext | NA | LALSYRLNMFTPYIGVKWS |
| 187 | | | J-MOMPext | NA | |
| 137 | Malaria | CSP | CSP | YLNKIQNSL | |
| 138 | | | CSPext | NA | HIKEYLNKIQNSLSTEWS |
| 188 | | | J-CSP | NA | |
| 139 | Treponema pallidum | Treponema pallidum repeat protein K | TprK | IEATLHCYGAYLTIGK NPDF | NA |
| 189 | | | J-TprK | NA | |
| 196 | HIV-1 | Envelope glycoprotein gp160 precursor | gp160 | KLTPLCVTL | |
| 197 | | | gp160ext | | LKPCVKLTPLCVTLNCSNI |
| 212 | | | J-gp160ext | | |
| 198 | HIV-1 | gag polyprotein | gp260 | EIYKRWII | |
| 199 | | | gp260ext | | PIPVGEIYKRWIILGLNK |
| 213 | | | J-gp260ext | | |

TABLE 3-continued

Antigen Sequences for Peptide P₂ and Example LEAPS™ Heteroconjugates

| | | | | |
|---|---|---|---|---|
| 200 | HIV-1 | p6 Gag | p6 | LYPLASLRSL |
| 201 | | | p6ext | NA |
| 214 | | | J-p6ext | NA |
| 202 | HIV-1 | Gag | gp77 | |
| 215 | | | J-gp77 | NA |
| 203 | HIV-1 | Pol 448 | p448 | KLVGKLNWA |
| 204 | | | p448ext | NA |
| 216 | | | J-p448ext | NA |
| 205 | Helicobacter pylori | Hypothetical protein HP0151 | HP0151 | GYNKAMGFL |
| 206 | | | HP0151ext | NA |
| 217 | | | J-HP0151ext | NA |
| 207 | Helicobacter pylori | Type II R-M system methyltransferase | RMS2 | IYVKTSSFL |
| 208 | | | RMS2ext | NA |
| 218 | | | J-RMS2 | NA |

Continued values (right column):
- 201: TPSQKQEPIDKELYPLASLRSLFGSDPSSQ
- 202: SLYNTVATLYCVHQR
- 204: VNDIQKLVGKLNWASQIYA
- 206: NSYPNGYNKAMGFLKVFKH
- 208: EIDHKIYVKTSSFLDFCRN

| Seq ID No. | Amino acid | J LEAPS conjugate | Ref. |
|---|---|---|---|
| 53 | 242-250 | NA | 59 |
| 54 | 237-255 | NA | 6 |
| 140 | NA | DLLKNGERIEKVEGGGSMGALTDLGQNLLYANSAH | |
| 55 | 17-24 | NA | 59 |
| 56 | 12-29 | NA | 7 |
| 141 | NA | DLLKINGERIEKVEGGGARATETYFSLNNKFRNPTV | |
| 57 | 16-24 | NA | 47 |
| 58 | 11-29 | NA | 13 |
| 142 | NA | DLLKNGERIEKVEGGGTCGFADLMGYIPAVGAPLG | |
| 59 | 22-30 | NA | 56 |
| 60 | 17-35 | NA | 14 |
| 143 | NA | DLLKISIGERIEKVEGGGLAPITAYSQQTRGLLGCH | |
| 61 | 20-28 | NA | 66 |
| 62 | 15-33 | NA | 15 |
| 144 | NA | DLLKNGERIEKVEGGGLQAGFFLLTRILTIPQSLD | |
| 63 | 144-159 | NA | 63 |
| 145 | NA | DLLKNGERIEKVEGGGLRGDLQVLAQKVARTL | |
| 64 | | NA | 53 |
| 146 | NA | DLLKNGERIEKVEGGGDYQGMLPVCPLIPGSSTTSTGPC | |
| 65 | 11-20 | NA | 67 |
| 66 | 6-25 | NA | 17 |
| 147 | NA | DLLKNGERIEKVEGGGPTLHEYMLDLQPETTDLYCY | |
| 67 | 11-19 | NA | 67 |
| 68 | 6-24 | NA | 18 |
| 148 | NA | DLLKNGERIEKVEGGGFGQSLLFGYPVYVFGDCV | |
| 69 | 137-145 | NA | 71 |
| 70 | 132-150 | NA | 20 |
| 149 | NA | DLLKNGERIEKVEGGGRKSYKKMLKEMGEVAPEYR | |
| 71 | 74-82 | NA | 58 |
| 72 | 69-87 | NA | 22 |
| 150 | NA | DLLKNGERIEKVEGGGVKVNKVDDTFYYVIYEAV | |
| 73 | 1452-1461 | NA | 54 |
| 74 | 1447-1466 | NA | 23 |
| 151 | NA | DLLKNGERIEKVEGGGERVDVRLDDDGNFQLMNDPG | |
| 75 | 36-44 | NA | 60 |
| 76 | 31-49 | NA | 28 |
| 152 | NA | DLLKNGERIEKVEGGGKTGVDSITEVECFLTPEMG | |
| 77 | 100-108 | NA | 68 |

TABLE 3-continued

Antigen Sequences for Peptide P₂ and Example LEAPS™ Heteroconjugates

| | | | |
|---|---|---|---|
| 78 | 95-113 | NA | 28 |
| 153 | NA | DLLKNGERIEKVEGGGLTCGNLLMWEAVTVKTEVL | |
| 79 | 579-587 | NA | 44 |
| 80 | 574-592 | NA | 29 |
| 154 | NA | DLLKNGERIEKVEGGGGIVITLLLLLIWERPVADFAT | |
| 81 | 10-18 | NA | 40 |
| 82 | 7-23 | NA | 33 |
| 155 | NA | DLLKNGERIEKVEGGGGFGQSLLYGYPVYVFGDCV | |
| 83 | 81-89 | NA | 75 |
| 84 | 76-94 | NA | 9 |
| 156 | NA | DLLKNGERIEKVEGGGNPEKDVLAELVKQIKVRVD | |
| 85 | 341-349 | NA | 46 |
| 86 | 336-354 | NA | 10 |
| 157 | NA | DLLKNGERIEKVEGGGTVELRQYDPVAALFFFDID | |
| 87 | 237-245 | NA | 50 |
| 88 | 232-250 | NA | 11 |
| 158 | NA | DLLKNGERIEKVEGGGLLARLFLYALALLLLASAL | |
| 89 | 12-20 | NA | 72 |
| 90 | 7-25 | NA | 12 |
| 159 | | DLLKNGERIEKVEGGGPVIVAPYLFWLAAIAASCF | |
| 91 | 16-25 | NA | 42 |
| 92 | 11-30 | NA | 30 |
| 160 | NA | DLLKNGERIEKVEGGGVHVPDVLLNGWRWRLGAIPP | |
| 93 | 44-52 | NA | 70 |
| 94 | 39-57 | NA | 34 |
| 161 | NA | DLLKNGERIEKVEGGGVEQSGHRQSIWITWHTQPV | |
| 95 | 31-45 | NA | 30, 74 |
| 162 | NA | DLLKNGERIEKVEGGGLVCLLAISVVPPSGQ | |
| 96 | 131-145 | NA | 30, 74 |
| 163 | NA | DLLKNGERIEKVEGGGELTDALISAFSGSYS | |
| 97 | 211-225 | NA | 30, 74 |
| 164 | NA | DLLKNGERIEKVEGGGLILYLCVPRCRKKP | |
| 98 | 399-407 | NA | 41 |
| 99 | 394-412 | NA | 24 |
| 165 | NA | DLLKNGERIEKVEGGGQSRRSISARGQELFRTLLE | |
| 100 | 139-149 | NA | 51 |
| 101 | 134-154 | NA | 26 |
| 166 | NA | DLLKNGERIEKVEGGGPIPVSEITDTIDKFGKCSSKA | 5 |
| 102 | 769-779 | NA | 51 |
| 103 | 764-784 | NA | 26 |
| 167 | NA | DLLKNGERIEKVEGGGKGLKQLPEGMDPFAEKPNATD | |
| 104 | 197-207 | NA | 51 |
| 105 | 192-212 | NA | 25 |
| 168 | NA | DLLKNGERIEKVEGGGALFQQARLCDLPATPKGSGTS | |
| 106 | 345-354 | NA | 51 |
| 107 | 340-354 | NA | 25 |
| 169 | NA | DLLKNGERIEKVEGGGREESPPHSVVNPFVK | |
| 108 | 445-453 | NA | 48 |
| 109 | 440-458 | NA | 27 |
| 170 | NA | DLLKNGERIEKVEGGGRQKSFSLPRSRTPIIPPVS | |
| 110 | 472-480 | NA | 48 |
| 111 | 467-485 | NA | 27 |
| 171 | NA | DLLKNGERIEKVEGGGSPWPGSAPLPSNRVRFGPS | |
| 112 | 593-600 | NA | 73 |
| 113 | 588-605 | NA | 27 |
| 172 | NA | DLLKNGERIEKVEGGGMATGEALWALPHAAAAVAM | |
| 114 | | NA | 55 |
| 173 | NA | DLLKNGERIEKVEGGGPIRHNGITMEM | 104 |

TABLE 3-continued

Antigen Sequences for Peptide P₂ and Example LEAPS™ Heteroconjugates

| | | | |
|---|---|---|---|
| 115 | 77-85 | | 45 |
| 116 | 72-90 | | 37 |
| 174 | NA | DLLKNGERIEKVEGGGPFQPPSLPITVYYAVLERA | |
| 117 | 94-102 | | 45 |
| 118 | 89-107 | | 37 |
| 175 | NA | DLLKNGERIEKVEGGGRACRSVLLNAPSEAPQIVR | |
| 119 | 302-310 | | 45 |
| 120 | 297-315 | | 37 |
| 176 | NA | DLLKNGERIEKVEGGGDPEDSALLEDPVGTVAPQI | |
| 121 | 439-448 | | 57 |
| 122 | 434-453 | | 38 |
| 177 | NA | DLLKNGERIEKVEGGGYLATGGFLIAYQPLLSNTLA | |
| 123 | 551-559 | | 57 |
| 124 | 546-564 | | 35 |
| 178 | NA | DLLKNGERIEKVEGGGRLEPHSAHPAFADVEQEAL | |
| 125 | 128-139 | NA | 76 |
| 126 | 123-144 | | 36 |
| 179 | NA | DLLKNGERIEKVEGGGGPVWCDRRDPLARYGSRVQIRC | |
| 127 | | NA | 62 |
| 180 | NA | DLLKNGERIEKVEGGGCSLEREDRDAWHLPAYK | |
| 128 | 672-693 | | 49 |
| 181 | | DLLKNGERIEKVEGGGQPTTRAQKLFAMWRITYKDTV | |
| 129 | 663-684 | | 49 |
| 182 | NA | DLLKNGERIEKVEGGGVAIIEVDNEQPTTRAQKLFAM | |
| 130 | 692-711 | | 69 |
| 183 | NA | DLLKNGERIEKVEGGGSIFYTYGTAPARISVPYVGI | |
| | | NA | 91 |
| 131 | 3-15 | NA | |
| 184 | NA | DLLKNGERIEKVEGGGEQQWNFAGIEAAA | |
| 190 | 239-247 | NA | 93 |
| 191 | 234-252 | NA | 95 |
| 209 | NA | DLLKNGERIEKVEGGGTQQIPKLVANNTRLWVYCG | |
| 132 | 6-14 | NA | 43 |
| 133 | 1-19 | NA | 21 |
| 185 | NA | DLLKNGERIEKVEGGGMFSRPGLPVEYLQVPSASM | |
| 192 | 88-97 | NA | 92 |
| 193 | 83-102 | NA | 97 |
| 210 | NA | DLLKINGERIEKVEGGGTGIAAVLTDGNPPEVKSVGL | |
| 134 | | NA | 82 |
| | | NA | |
| 186 | NA | DLLKNGERIEKVEGGGMKKDNIAAMVLRGMAK | |
| 194 | 144-155 | NA | 90 |
| 195 | 135-164 | NA | 96 |
| 211 | NA | DLLKNGERIEKVEGGGGSGKAKEVLKSYVLEGTLTAEK TTLVVKEG | |
| 135 | 250-258 | NA | 52 |
| 136 | 245-263 | NA | 8 |
| 187 | NA | DLLKNGERIEKVEGGGLALSYRLNMFTPYIGVKWS | |
| 137 | 33-41 | NA | 65 |
| 138 | 28-46 | NA | 19 |
| 188 | NA | DLLKNGERIEKVEGGGHIKEYLNKIQNSLSTEWS | |
| 139 | 242-250 | NA | 61 |
| 189 | NA | DLLKINGERIEKVEGGGIEATLFICYGAYLTIGKNPDF | |
| 196 | 122-130 | | 83, 88 |
| 197 | 117-135 | | 101 |
| 212 | | DLLKNGERIEKVEGGGLKPCVKLTPLCVTLNCSNI | |
| 198 | 260-267 | | 84 |
| 199 | 255-272 | | 100 |
| 213 | | DLLKNGERIEKVEGGGPIPVGEIYKRWIILGLNK | |

TABLE 3-continued

Antigen Sequences for Peptide P2 and Example LEAPS™ Heteroconjugates

| | | | |
|---|---|---|---|
| 200 | 35-44 | NA | 87 |
| 201 | 23-52 | NA | 98 |
| 214 | NA | DLLKNGERIEKVEGGGTPSQKQEPIDKELYPLASL RSLFGSDPSSQ | |
| 202 | 77-91 | NA | 83, 86, 99 |
| 215 | NA | DLLKNGERIEKVEGGGSLYNTVATLYCVHQR | |
| 203 | 358-366 | | 88 |
| 204 | 353-371 | | 103 |
| 216 | | DLLKNGERIEKVEGGGVNDIQKLVGKLNWASQIYA | |
| 205 | 11-19 | NA | 89 |
| 206 | 6-24 | NA | 94 |
| 217 | NA | DLLKNGERIEKVEGGGNSYPNGYNKAMGFLKVFKH | |
| 207 | 40-48 | NA | 89 |
| 208 | 35-53 | NA | 102 |
| 218 | NA | DLLKNGERIEKVEGGGEIDHKIYVKTSSFLDFCRN | |

Embodiments also contemplate reversal sequences where the order of amino acids in Peptides $P_1$ and/or $P_2$ is reversed from N-term to C-terminus. For example peptide J has the sequence DLLKNGERIEKVE (SEQ ID No. 3). The reversal sequence for any ICBL disclosed herein is envisioned for inclusion in a LEAPS™ heteroconjugate as described herein. Further, the non-reversal sequence for an ICBL can be conjugated with an antigen sequence from Tables 1, 2 or 3 or with a reversal antigen sequence from Tables 1, 2 or 3. The reversal sequence for SEQ ID No. 7 is GTRVLAR-TRQYTADN, such that LEAPS™ heteroconjugates contemplated in certain embodiments include DLLKNGE-RIEKVEGGG GTRVLARTRQYTADN and DLLKNGERIEKVEGGGNDATYQRTRALVRTG, where Peptide J (SEQ ID No. 3) is conjugated with the reversal sequence of SEQ ID No. 7 or the non-reversal sequence of SEQ ID No. 7, respectively. Further, the reversal sequence for an ICBL can be conjugated with an antigen sequence from Tables 1, 2 and 3 or with a reversal antigen sequence from Tables 1, 2 and 3. Such LEAPS™ heteroconjugates contemplated in certain embodiments include EVKEIREG-NKLLDGGGGTRVLARTRQYTADN and EVKEIREG-NKLLDGGGNDATYQRTRALVRTG, where the reversal sequence for Peptide J (SEQ ID No. 3) is conjugated with the reversal sequence of SEQ ID No. 7 or the non-reversal sequence of SEQ ID No. 7, respectively.

Alternatively, the invention contemplates a variable immunomodulatory peptide construct having the Formula (III)

where $P_3$ is a peptide construct comprised of $X_1$ to $X_{14}$ said peptide $P_3$ being associated with Type A influenza or another infectious agent. For example, the immunomodulatory peptide can contain a highly conserved protein such as but not limited to the M2e or other matrix protein, or NP1 nucleoprotein, and $P_4$ is a peptide construct comprised of $X_1$ to $X_{14}$ causing a Th1 directed immune response by said set or subset of T cells to which the peptide $P_3$ is attached or which binds to a dendritic cell or T cell receptor causing said set or subset of DC or T cells to which the peptide $P_3$ is attached to initiate and complete, an immune response.

Alternatively, the invention contemplates a variable immunomodulatory peptide construct having the formula (IV)

$$P_5\text{-x-}P_6 \qquad \text{(IV)}$$

where $P_5$ is a peptide construct comprised of $X_1$ to $X_{14}$ said peptide $P_5$ being associated with Type A influenza or another infectious agent, and $P_6$ is a peptide construct comprised of $X_1$ to $X_{14}$ causing a $T_h2$ directed immune response by said set or subset of T cells to which the peptide $P_5$ is attached or which binds to a T cell receptor causing said set or subset of T cells to which the peptide $P_5$ is attached to initiate an immune response, such that $X_1$ to $X_{10}$ and $X_{14}$ describe a group of amino acids based on their features and $X_{11}$ to $X_{13}$ describe modifications to the peptide construct, wherein $X_1$ is selected from the group consisting of Ala and Gly, $X_2$ is selected from the group consisting of Asp and Glu, $X_3$ is selected from the group consisting of Ile, Leu and Val, $X_4$ is selected from the group consisting of Lys, Arg and His, $X_5$ is selected from the group consisting of Cys and Ser, $X_6$ is selected from the group consisting of Phe, Trp and Tyr, $X_7$ is selected from the group consisting of Phe and Pro, $X_8$ is selected from the group consisting of Met and Nle, $X_9$ is selected from the group consisting of Asn and Gln, $X_{10}$ is selected from the group consisting of Thr and Ser, $X_{11}$ is $Gaba^{\chi}$ where $X_2X_3$, $X_3X_2$, $X_2X_3$, $X_3X_2$, $X_3X_3$, or $X_2X_2$ can be substituted with $X_{11}$;

$X_{12}$ is selected from the group consisting of acetyl, propionyl group, D glycine, D alanine and cyclohexylalanine;

$X_{13}$ is 5-aminopentanoic where any combination of 3 to 4 amino acids of $X_2$ and $X_3$ can be replaced with $X_{13}$;

$X_{14}$ is selected from the group consisting of $X_1$, $X_2$, $X_3$, $X_4$, $X_5$, $X_6$, $X_7$, $X_8$, $X_9$ and $X_{10}$; and x is a direct bond or linker for covalently bonding $P_5$ and $P_6$. For example, a variable immunomodulatory peptide construct of formulae (III)-(IV) can contain a peptide causing a $T_h2$ directed immune response related to peptide J (SEQ ID No. 3), such $X_2X_3X_3X_4X_9X_1X_2X_4X_3X_2X_4X_3X_2$ as (SEQ ID No. 225). One having skill in the art would recognize that each of $X_1$ to $X_{14}$ represents a group of amino acids having similar charge, polarity, hydrophobicity, chemical functionality, size and/or shape. As such, one having skill in the art will recognize that a variable immunomodulatory peptide can be identified by substituting a specific amino acid residue in any sequence disclosed herein with the corresponding group $X_1$ to $X_{14}$ including and representing the properties of that specific residue. For example, one having skill in the art will recognized that a Gly residue can be represented by group $X_1$, and Trp residue can be represented by $X_6$ and an Arg residue can be represented by group $X_4$. As such, one having skill in the art will be able to unambiguously assign the tripeptide GWR as $X_1X_6X_4$. Similarly, one having skill in the art will be able to unambiguously assign any of the sequences disclosed herein to a variable immunomodulatory peptide construct having residue represented by $X_1$ to $X_{14}$. For example, SEQ ID No. 7 derived from influenza virus can be converted to the variable immunomodulatory peptide $X_9X_2X_1X_{10}X_6X_9X_4X_{10}X_4X_1X_3X_3X_4X_{10}X_1$ (SEQ ID No. 226) that can be incorporated into an immunomodulatory peptide construct.

Methods of Treating a Subject with LEAPS™ Heteroconjugates

Any of the LEAPS™ heteroconjugates in accordance with Formulae (I)-(IV) described above can be combined with an appropriate pharmaceutically suitable carrier with one or more optional adjuvants for administration to a subject. Such combination of the LEAPS™ heteroconjugates and a pharmaceutically suitable carrier can function as a vaccine to confer immune resistance to a broad spectrum of Type A influenza viruses or any of the infections agents described in Table 3. For example, an immunomodulatory peptide construct having any of SEQ ID No.'s 1, 2, 11-36, 47-52, 140-189 and 209-218 individually or as a mixture thereof, can be combined with a pharmaceutically suitable carrier to form a vaccine composition.

These LEAPS™ heteroconjugate peptide-based vaccines can provide prophylactic protection and also have the potential for therapeutic treatment of recurrent disease. The LEAPS™ technology is a T cell modulation platform technology that can be used to design and synthesize proprietary epitope sequences compatible with LEAPS™ technology. Each LEAPS™ heteroconjugate is composed of an ICBL which has the ability to induce and elicit protective immunity and antigen specific response in animal models.

LEAPS™ technology directly mimics cell to cell interactions on the dendritic and T-cell surfaces using synthetic peptides. The LEAPS™ heteroconjugates containing the antigenic disease epitope linked to an ICBL can be manufactured by peptide synthesis or by covalently linking two peptides. Depending on the type of LEAPS™ heteroconjugates and ICBL used, the peptide construct is able to direct the outcome of the immune response towards the development of T-cell function with primary effector T-cell functions: T Lymphocyte; helper/effector T Lymphocyte, type 1 or 2 (Th1 or Th2), cytotoxic (Tc) or suppressor (Ts) without excessive amounts of proinflammatory and inflammatory cytokines.

The type of the immune response elicited against an immunogen or a natural infection can be classified as Th1/Tc1, Th2/Tc2 or Th3 based on the predominant IgG subtype, the cytokines that are induced, or the presence or absence of delayed type hypersensitivity (DTH) response. A Th0 response is an earlier response that can mature into either a Th1 or a Th2 response and has features of both. The Th1 (CD4)/Tc1 (CD8) response is characterized by activation of $CD4^+$ and $CD8^+$ T cells to produce IL-2, TNF-β, and IFN-γ and to promote the production of IgM and specific IgG antibody subtypes and cell-mediated immune responses including delayed-type hypersensitivity (DTH). These responses reinforce early, local and inflammatory responses. Th2 responses promote different IgG subclasses, IgE and IgA responses but not cell mediated responses to antigen (Ag). Th2 responses prevent the onset of protective Th1 cell mediated responses important for infection control, which may exacerbate disease. Initiation of Th1 and Th2 responses has important implications in terms of resistance and susceptibility to disease. Th1-dominated responses are potentially effective in eradicating influenza viral infections, and are important for the induction of cytotoxic T lymphocytes (CTL). Most importantly, for many vaccines it is thought that initiation of immunity with a Th1 response and then progression to a Th2 response promotes better immune memory.

Many suitable pharmaceutical carriers are known to persons skilled in the art. The primary function of the pharmaceutical carrier is to assist in the delivery and/or administration the immunomodulatory peptide construct to a subject. The pharmaceutical carrier can be as simple as sterilized water. In certain embodiments, the pharmaceutical suitable carrier is a sterile pyrogen-free formulation containing from about 0.2 mg/mL to about 10 mg/mL of the immunomodulatory peptide construct in phosphate-buffered saline (PBS) and trehalose or other sugar that has been lyophilized to remove water and reconstituted prior to use with sterilized water for injection to a subject.

Optional adjuvants include products such as GMP products including Montanide™ ISA-51 (Seppic, Fairfield, N.J.), Depovax™, a liposomal adjuvant currently in phase I trials by Immunovaccine Technologies, and MAS1™, a proprietary water-in-oil GMP adjuvant from MerciaPharma currently in phase II clinical studies. Alum is currently the only FDA licensed adjuvant of the group. In certain embodiments, the composition administered to a subject containing a LEAPS™ heteroconjugate, as described herein, has mixture of an aqueous phase and an adjuvant oil phase from about 1:4 to about 4:1.

A composition having the LEAPS™ heteroconjugate and a suitable pharmaceutical carrier with or without an optional adjuvant can be administered to a subject by subcutaneous or intramuscular injection in a therapeutically effective amount. The subject can be a mammal subject including a human subject.

Freund's Incomplete Adjuvant is also contemplated (Sigma Corp., St. Louis, Mo.). For Product Number F5506, the Storage Temperature is 2-8° C. where F5881 is a clear, amber liquid containing particulate matter (dried cells). F5506 is a clear amber liquid. Freund's incomplete Adjuvant is one of the most commonly used adjuvants in research. It is used as a water-in-oil emulsion. It is prepared from non-metabolizable oils (paraffin oil and mannide monooleate). First developed by Jules Freund in the 1940's, Freund's Adjuvant is designed to provide continuous release of antigens necessary for stimulating a strong, persistent immune response. The main disadvantage of Freund's Adjuvant is that it can cause granulomas, inflammation at the inoculation site and lesions. To minimize side-effects, Incomplete Freund's Adjuvant is used for the boosts. (Freund, J. and McDermott, K., Proc. Soc. Exp. Biol. Med., 1942; 49:548-553; Freund, J., Ann. Rev. Microbiol., 1947; 1:291; Freund, J., Adv. Tuberc. Res., 1956; 7:130; Bennett, B. et al., J. Immuno. Meth., 1992; 153:31-40; Deeb, B. J. et al., J. Immuno. Meth., 1992; 152:105-113; Harlow, E. and Lane, D., Antibodies: A Laboratory Manual, Cold Spring Harbor Laboratory, 1988).

Maturation of Dendritic Cells with LEAPS™ Heteroconjugates

In certain embodiments, a subject is stimulated to have an immune response to Type A influenza by being administered DCs matured and activated in the presence of a LEAPS™ heteroconjugate consistent with Formulae (I) or (II). Induction of an optimal immune response requires mimicking nature's approach to immunization. DCs play a major role in initiating and directing the immune response to a vaccine. The initial host response to an antigen requires internalization of the antigen into the DC followed by processing and presentation by the MHC I or II proteins for T cell recognition. DCs, macrophages and B cells are capable of presenting antigens to $CD4^+$ helper T cells and $CD8^+$ cytotoxic T cells as peptides held within grooves of the class II and I MHC proteins, respectively. These cells can be functionally divided into DC1 and DC2 cell types based on the means of their activation, their cytokine output and the nature of their influence on T cells. DC1 cells produce IL12 and promote Th1-type responses whereas DC2 cells promote Th2-type responses.

As described above, the LEAPS™ heteroconjugates described herein can be administered to a subject to generate an immune response in vivo. The immunomodulatory peptide constructs can also modulate the properties of immune cells, including DCs, ex vivo, in order to activate, mature, and direct the character and phenotype of immune cells (e.g. DCs) contacted with the LEAPS™ heteroconjugate. Such treated immune cells, which can include DCs and/or monocytes, can then be introduced into a subject for the purpose of increasing immunity against Type A influenza virus. DCs treated with a LEAPS™ heteroconjugate ex vivo and transferred to a subject can confer acquired immunity to the subject.

In certain embodiments, DCs and/or monocytes are extracted from a subject or donor away from other tissues of the body. The dendritic cells and/or monocytes are then contacted with one or more LEAPS™ heteroconjugates. DCs and/or monocytes isolated from a subject or donor can be in an immature state characteristic of immune cells prior to contact with an antigen. Such cells are herein referred to as immature DCs (iDCs). The DCs and/or monocytes can be isolated from blood derived monocytes and/or bone marrow taken from a subject or donor. DCs and/or monocytes expressly include monocyte cells capable of differentiating into macrophages and/or dendritic cells that can function to present antigens to T cells under appropriate conditions. Upon contact or treatment of the isolated dendritic cells and/or monocytes with the LEAPS™ heteroconjugates, the dendritic cells and/or monocytes undergo a maturation to a state that directs immune response.

As defined herein, the term "immature DCs" (iDCs) refers to cells derived from a donor or subject that are not competent to induce T cell activation upon interaction with T cells. Such iDCs are also known in the art as naïve DCs. Such iDCs can have certain physical characteristics such as a reduced level of expression of CD80 and/or CD86, MHC molecules (class I and/or class II), other surface markers and a reduced appearance of dendrites. Immature DCs, as defined herein, expressly includes monocytes that can be stimulated to form dendritic cells. As defined herein, terms "matured DCs" and "more matured DCs" refer to DCs after contact with any of the LEAPS™ heteroconjugates described herein. Such matured DCs can have certain physical characteristics including upregulation of CD80 and/or CD86, MHC I or II molecules, an increased appearance of dendrites and secretion of IL-12p70.

In certain embodiments, contacting monocyte cells with one or more LEAPS™ heteroconjugates can induce the development of the monocyte cells or iDCs to DC1 (Th1-inducing dendritic cells) and/or DC2 cells (Th2-inducing dendritic cells) or other cell type allowing for acquired immunity to influenza when transferred to a subject. In certain other embodiments, iDCs and/or monocytes isolated from a subject or donor are contacted with a media containing granulocyte-macrophage colony stimulating factor (GM-CSF) to stimulate the expression of CD11c on the surface of the iDCs or monocytes. The iDCs and/or monocytes after exposure to GM-CSF are contacted with one or more LEAPS™ heteroconjugates to induce the maturation of the monocyte cells or iDCs to DC1 (Th1-inducing dendritic cells) and/or DC2 cells (Th2-inducing dendritic cells) or other cell type allowing for acquired immunity to influenza when transferred to a subject.

In certain embodiments, DCs and/or monocytes are extracted from a subject or donor away from other tissues of the body in a composition of isolated iDCs and/or monocytes. As described herein, a composition of isolated DCs and/or monocytes is a composition in which the DCs and/or monocytes are present away from other body tissue including blood or bone marrow. In certain embodiments, a composition of isolated DCs and/or monocytes contains at least 50% of the viable cells present in the composition being DCs and/or monocytes. In certain embodiments, the composition of DCs and/or monocytes is substantially free from whole red blood cells.

In certain embodiments, the iDCs and/or monocytes are contacted or treated with one or more LEAPS™ heteroconjugates for about 6 hours to about 96 hours or from about 12 hours to about 72 hours. In certain other embodiments, the iDCs and/or monocytes are contacted or treated with one or more LEAPS™ heteroconjugates for a period of time longer than about 6 hours. In additional embodiments, the iDCs and/or monocytes are contacted or treated with one or more LEAPS™ heteroconjugates for a period of time longer than about 12 hours. In certain additional embodiments, the iDCs and/or monocytes are contacted or treated with one or more LEAPS™ heteroconjugates for a period of time longer than about 24 hours. In certain embodiments, the iDCs and/or monocytes are contacted or treated with one or more LEAPS™ heteroconjugates at a ratio from about 5 to about 50 micromoles of one or more LEAPS™ heteroconjugates per $10^6$ iDCs and/or monocytes. In certain other embodiments, the iDCs and/or monocytes are contacted or treated with one or more LEAPS™ heteroconjugates at a ratio greater than about 5 micromoles of one or more LEAPS™ heteroconjugates per $10^6$ iDCs and/or monocytes.

In certain embodiments, the iDCs and/or monocytes are contacted with GM-CSF for a period of about 1 day to about 10 days or from about 3 days to about 10 days. In certain additional embodiments, the iDCs and/or monocytes are contacted with GM-CSF for a period greater than about 5 days. In certain embodiments, the iDCs and/or monocytes are contacted with a media having a concentration of from about 5 to about 200 ng/mL of GM-CSF or from about 10 to about 150 ng/mL of GM-CSF. In other embodiments, the DCs and/or monocytes are contacted with a media having a concentration of GM-CSF greater than about 5 ng/mL. In certain embodiments, the DCs and/or monocytes are contacted with a media having a concentration of GM-CSF greater than about 15 ng/mL of GM-CSF.

Upon contact of iDCs and/or monocytes with the LEAPS™ heteroconjugate, an increased expression level of interleukin-12p70 (IL-12p70) can be observed relative to iDCs and/or monocytes not contacted with the LEAPS™ heteroconjugate. In certain embodiments, iDCs and/or monocytes contacted with the LEAPS™ heteroconjugate exhibit an up-regulation of at least one of the following: CD80, CD86, MHC class I, or MHC class II cell surface markers relative to iDCs and/or monocytes not contacted with the LEAPS™ heteroconjugate.

Immature dendritic cells and/or monocytes after contact with an immunomodulatory LEAPS™ heteroconjugate can be referred to as matured dendritic cells. The matured dendritic cells can modulate an immune response when administered or introduced into a subject. An immune response can be induced in a subject under situations where matured dendritic cells are washed free of LEAPS™ heteroconjugate that is unbound from the surface of a dendritic cell. As such, the amount of any antigen, including the antigen peptide $P_2$ forming part of the LEAPS™ heteroconjugate, introduced into a subject is limited. As such, introduction of the matured DCs described herein minimizes the production of a "cytokine storm" or other inflammatory responses in a treated subject. Matured DCs created through contact with a LEAPS™ heteroconjugate do not produce acute phase cytokines that can trigger a cytokine storm. See Taylor et al., Vaccine 28 (2010) 5533-5542.

Without wishing to be bound by any one particular theory, it is believed that the LEAPS™ heteroconjugate is retained on the surface of DCs in manner allowing for the interaction of the LEAPS™ heteroconjugate with T cell receptor present on the surface of T cells. As such, DCs matured in the manner described above can be introduced or administered to a subject such that the LEAPS™ heteroconjugate present of the surface of the introduced or administered DCs can interact with the subject's in situ T cells to direct an antigen specific immune response. More specifically, activation of T cell-mediated immune response requires multiple stimulator interactions, including interaction with T cell receptor (TCR) present on the surface of T cells. It is believed that these more matured DCs having the LEAPS™ heteroconjugate present of the surface can provide the necessary interaction to activate T cells and direct an immune response to the Peptide $P_2$ antigen of the LEAPS™ heteroconjugate. Further, it is believed that these more matured DCs formed using the methods described herein have an advantageous profile of secreted cytokines that do not stimulate a cytokine storm or other deleterious inflammation response in a subject.

The more matured dendritic cells and/or T cells can be used in an autologous fashion. In certain embodiments, iDCs and/or monocytes are isolated from a subject to be treated, such isolated cells can be blood derived monocytes and/or bone marrow cells taken from the subject. The isolated iDCs and/or monocytes are contacted with one or more LEAPS™ heteroconjugates having the structure $P_1$-x-$P_2$ or $P_2$-x-$P_1$ to induce maturation to more matured dendritic cells. An effective amount of the LEAPS activated DCs are administered to the same subject from which the matured cells were originally isolated. The subject can be a mammal, including a human. As such, the method for modulating an immune response to Type A influenza virus is autologous and minimizes exposure to any potential non-self antigen that can trigger a "cytokine storm" or other undesirable inflammatory response.

In certain other embodiments, iDCs and/or monocytes can be isolated from a compatible donor, treated with a heteroconjugate peptide having the structure $P_1$-x-$P_2$ or $P_2$-x-$P_1$ to induce maturation to form matured dendritic cells, and an effective amount of the matured dendritic cells and/or T cells administered to a subject having compatibility with the donor.

Development of DC1 or DC2 cells is determined by environmental factors, including dose and form of the antigen, but mostly by stimulation of Toll-Like Receptors (TLR) and other receptors for microbial pathogen associated molecular patterns, artificial ligands of these receptors and other stimuli. Many of these TLR molecules are triggered by adjuvants made from the TLR ligands such as Lipid A, MPL, CpG, LPS, etc. Other receptors on DCs known as LIR (leukocyte immunoglobulin-like receptors or also known as CD85) are known to recognize self-epitopes found on various MHC molecules. Both CEL-1000 and Peptide J are derived from MHC molecules and are likely ligands for LIRs. Many of these receptors' responses are also triggered by their own adjuvants. However, the identity of the receptor for LEAPS™ heteroconjugate on DCs is not definitively known. (Annunziato F. et al., Expression and release of LAG-3-encoded protein by human CD4+ T cells are associated with IFN-gamma production, FASEB J., 1996 May; 10(7):769-76; Anderson K J, Allen R L., Regulation of T-cell immunity by leucocyte immunoglobulin-like receptors: innate immune receptors for self on antigen-presenting cells, Immunology, 2009 May; 127(1):8-17; Sloane D E et al., Leukocyte immunoglobulin-like receptors: novel innate receptors for human basophil activation and inhibition, Blood, 2004 Nov. 1; 104(9):2832-9; Shiroishi M et al., Efficient leukocyte Ig-like receptor signaling and crystal structure of disulfide-linked HLA-G dimer, J Biol. Chem., 2006 Apr. 14; 281(15):10439-47; Shiroishi M et al., Human inhibitory receptors Ig-like transcript 2 (ILT2) and ILT4 compete with CD8 for MHC class I binding and bind preferentially to HLA-G, Proc Natl Acad Sci USA. 2003 Jul. 22; 100(15):8856-61; Colonna M et al., A novel family of Ig-like receptors for HLA class I molecules that modulate function of lymphoid and myeloid cells, J Leukoc. Biol., 1999 September; 66(3):3; 75-81; Borges L, et al., A family of human lymphoid and myeloid Ig-like receptors, some of which bind to MHC class I molecules, J Immunol., 1997 Dec. 1; 159(11):5192-6; Shiroishi M et al., Structural basis for recognition of the non-classical MHC molecule HLA-G by the leukocyte Ig-like receptor B2 (LILRB2/LIR2/ILT4/CD85d), Proc. Natl. Acad. Sci. U.S.A., 2006 Oct. 31; 103(44):16412-7; all of which are incorporated herein by reference).

The matured DCs having been treated with the LEAPS™ heteroconjugate having the structure $P_1$-x-$P_2$ or $P_2$-x-$P_1$ can be administered to a subject with an active influenza virus infection. A significant reduction in influenza virus titer can be observed within about 3 days of the administration of the matured LEAPS™ heteroconjugate-activated DCs to a subject having an active influenza infection. In certain embodiments, influenza virus titer can be reduced by 20% or more within 3 days post administration of the matured LEAPS™ heteroconjugate-activated DCs. In certain embodiments, virus titer can be reduced by 50% or more three days post administration of the matured LEAPS™ heteroconjugate-activated DCs.

Alternatively, the matured DCs having been contacted by the LEAPS™ heteroconjugate having the structure $P_1$-x-$P_2$ or $P_2$-x-$P_1$ can be administered as a prophylactic against future influenza virus exposure. Specifically, the matured DCs produce an immune response to the antigen of the Peptide $P_2$ that can lead to long-term immune memory in a similar fashion as direct vaccination with LEAPS™ heteroconjugates.

In a surprising observation, the matured DCs having been contacted by the LEAPS™ heteroconjugate having the structure $P_1$-x-$P_2$ or $P_2$-x-$P_1$ have a capability to be recruited directly to a site of an infection. That is, the matured DCs can be recruited to an infection site involving an organism or virus expressing the epitope of the antigenic Peptide $P_2$.

DCs can be tagged or tracked using several known techniques. For example, cells can be labeled or stained with carboxy fluorescein succinimidyl ester (CSFE), Cy5.5 or Alexa Fluor® which have fluorescent properties. The distribution of CSFE-dyed dendritic cells throughout different tissues can be determined through fluorescent microscopy or flow cytometry techniques. Those skilled in the art will recognize that the technique for tracking the distribution of DCs is not limited. For example, radio labeling techniques can be employed to track the distribution of DCs. In certain embodiments, at least a majority of the matured DCs contacted with the peptide construct having the structure $P_1$-x-$P_2$ or $P_2$-x-$P_1$ are found in the lung tissue of an influenza virus infected mouse at a time point 8 hours post administration of the matured DCs. The lungs are the primary location of influenza infection in mice. In other species, the primary location of influenza infection can be different, such as the upper respiratory tract for humans infected with influenza virus. In certain embodiments, a majority of the LEAPS™ heteroconjugate-activated DCs locate to the site of an infection within 8 hours of administration of the DCs to a patient, where the heteroconjugate contains an antigen derived from the virus causing the infection.

LEAPS™ heteroconjugate-activated matured dendritic cells have been previously reported to be useful for prophylactic use providing immunity against a later challenge with herpes simplex virus 1 (HSV-1) virus, Taylor et al., *Vaccine* 28 (2010), 5533-43. In the Taylor et al. study, mice were not exposed to nor suffering from an active HSV-1 infection at the time of treatment with LEAPS™ heteroconjugate-activated more matured DCs. As such, the DCs administered in the Taylor et al. study could not migrate to a site of infection for HSV-1, since there was no active HSV-1 infection in the subject mice at the time of administration. As demonstrated in the Examples below, the ability of LEAPS™ heteroconjugate-activated DCs to migrate or accumulate at the site of infection for an organism or virus is unexpected.

The matured DCs contacted with the LEAPS™ heteroconjugate having the structure $P_1$-x-$P_2$ or $P_2$-x-$P_1$ were found to have a beneficial effect in ameliorating influenza infection without the use of additional immunomodulators.
Diagnostic Application of Dendritic Cells with LEAPS™ Heteroconjugates Matured DCs treated with a LEAPS™ heteroconjugate in vitro have a property allowing for the localization of such matured DCs to the site of an infection within the body of a subject. The LEAPS™ heteroconjugate has a $P_2$ peptide sequence originating or derived from an antigen, as described above. Maturation of DCs through treatment with a LEAPS™ heteroconjugate allows for the matured DCs to collect or to locate in an area of a subject's body where a source of the antigen from which the $P_2$ is derived can be found. As such, an infection by a pathogen, virus, rickettsia, bacteria or parasite can be detected by observing matured dendritic cells administered to a subject collecting, locating or concentrating at a site within the subject's body where the virus can be found.

In certain embodiments, matured DCs can be labelled with a tracking marker to allow for their location within a subject's body to be tracked after administration to the subject. For example, in the matured DC's can be labelled with radionuclides to allow for the location of the labeled, matured DCs to be detected using appropriate equipment. Appropriate radionuclides include radioactive isotopes of iodine such as $^{131}I$ or $^{125}I$. The location of radionuclides can be determined using a radiation detector or photographic film sensitive to radiation.

As the Examples below demonstrate, DCs matured by treatment with a LEAPS™ heteroconjugate, as describe herein, have the ability to concentrate in a region of a subject's body hosting or similar antigen source. Specifically, the matured DCs obtained by treatment with a LEAPS™ heteroconjugate are sensitized to sources of the antigen from which the peptide $P_2$ forming the specific LEAPS™ heteroconjugate used to mature the matured DCs is derived. For example, DCs matured with a LEAPS™ heteroconjugate containing a peptide $P_2$ derived from an infectious agent will accumulate in area of the subject's body where antigens originating from the virus can be found.

Early detection of specific conditions is often crucial to successful treatment. Unfortunately, many traditional techniques for verifying the presence of an infection, pathogen, virus, bacteria, rickettsia or parasite are not effective until the condition has progressed to a significant degree such that symptoms are manifest. Likewise, the presence of antibodies in the blood serum having affinity for a particular antigen is often not discernible until a substantial time has past since infection and an immune response is well on the way.

The immunomodulatory LEAPS™ heteroconjugates can be used to modulate a subject's immune system to detect the presence of an infection at an early stage. The LEAPS™ heteroconjugates can be used to mature immature DCs or monocytes isolated from the subject or a compatible donor to be sensitive to a desired antigen originating or derived from an infectious agent whose detection is desired. Since the DCs can be manipulated outside of the body, the matured DCs can be labelled with a tracking marker in a manner allowing for sensitive detection. In particular, labelling with radionuclides can allow for detection down to very low levels. Similarly, the presence of a fluorescent dye can be discerned at very low levels.

In certain embodiments, matured DCs can be labelled with a tracking marker to allow for location within a subject's body to be tracked after administration to the subject. For example, matured DC's can be labelled with radionuclides (radioisotopes) to allow for the location of the labeled, matured DCs to be detected using appropriate equipment. Appropriate radionuclides include radioactive isotopes of iodine such as $^{131}I$ or $^{125}I$ as well as other radionuclides including $^{18}F$, $^{32}P$, $^{64}Cu$, $^{90}Y$, $^{99m}Tc$, $^{124}I$, $^{89}Zr$, $^{111}In$, $^{188}Re$, or $^{177}Lu$. The location of radionuclides can be determined using a radiation detector, single-photon tomography/computed tomography (SPECT/CT), scintillation camera, positron emission tomography or photographic film sensitive to radiation. In certain further embodiments, matured DC's can be labeled with a fluorescent dye, such as carboxyfluorescein succinimidyl ester (CSFE), Cy 5.5 or Alexa Fluor® where the presence of such dye-labelled DCs can be detected in tissues taken by biopsy from a patient administered the matured DCs. In certain embodiments, the tracing marker is a luminescence dye. In certain embodiments, the presence of fluorescence in a tissue sample taken from a subject's body is determined by flow cytometry.

In certain embodiments, immature DCs and/or monocytes are collected from a subject or a compatible donor and matured by treatment or contact with a LEAPS™ heteroconjugates having a structure of Formulae (I) or (II) and incorporating an antigen peptide ($P_2$) sequence derived from an infection agent such as an infection pathogen virus, rickettsia, bacteria or parasite. The matured DCs are administered to the subject through an intravenous route or another appropriate route and a period of time is allowed to elapse. A diagnostic determination of the presence of the desired infection, pathogen virus, rickettsia, bacteria or parasite can be made by observing the location of the administered matured dendritic cells and/or tracking marker. The tracking marker can be conjugated to the LEAPS™ heteroconjugate used to treat the DCs or can be conjugated to an antibody (mAb) having affinity for a cell surface marker or other protein present on the DC. Example cell surface markers to which such an antibody can have affinity include MHC II, CD11c, DEC-205, Dectin-1, DC-SIGN, and DC-LAMP. When the desired infection, pathogen virus, rickettsia, bacteria or parasite is present in the body of the subject, the matured DCs and/or tracking marker will concentrate at the location, tissue type or organ structure where the infection is present within the subject's body. When the targeted infection is not present in the body of the subject, the matured DCs and/or tracking marker is expected to be diffused in different locations of the subject's body and not concentrated in any particular location, tissue type or organ structure.

The diagnostic determination can be made by only observing the location, tissue type or organ structure where the infection, pathogen virus, rickettsia, bacteria or parasite is expected to be found. For example, if matured DCs are made with a LEAPS™ heteroconjugates containing an antigen sequence derived from a virus known to cause respiratory infections, then only observation of the presence of the matured DCs and/or tracking marker in the subject's lungs or other respiratory organs needs to be performed. Since the amount of tracking marker administered to the subject is known, a determination of a concentration of the matured DCs and/or tracking marker in a specific location, tissue type or organ structure can be made without the need for a direct comparison with other body tissues.

In certain embodiments, a majority of the matured DCs and/or tracking marker is present in a specific location, tissue type or organ structure of the subject indicating the presence of the targeted infection, pathogen virus, rickettsia, bacteria or parasite. In certain other embodiments, at least about 75% of the matured DCs and/or tracking marker are present in a specific location, tissue type or organ structure of the subject indicating the presence of an influenza infection. In certain other embodiments, less than a majority of the matured DCs and/or tracking marker present in a specific location, tissue type or organ structure can indicate the presence of an infection, pathogen virus, rickettsia, bacteria or parasite, where the amount of the DCs and/or tracking marker in the specific location, tissue type or organ structure is higher than in surrounding areas.

Labeling of Dendritic Cells and Delivery of Therapeutic Compounds

The ability of LEAPS™ heteroconjugate-treated DCs to localize to the site of an infection can be utilized to deliver therapeutic agents directly to the site of the infection in addition to the diagnostic applications discussed above. The therapeutic agent or radioisotope conjugated to a LEAPS™ heteroconjugate or to a monoclonal antibody (mAb) can by conjugated or linked to a lysosomatropic agent. A lysosomatropic agent is a weak organic base that can diffuse through membranes but will become protonated in the lysosome of a cell, where the protonated lysosomatropic agent is unable to diffuse through membranes and will, therefore, be trapped within the cell. Hydrophobic amines, including butylamine, spermidine, spermine, methylamine, and cyanine dyes (including those used for studying membrane potential or that are used as tracers in neurobiology) are examples of lysosomatropic agents. These lysosomatropic agents can be modified to be conjugated to a radioisotope or to a therapeutic compound (e.g. cytokines, *staphylococcal* enterotoxin A superantigen, *staphylococcal* enterotoxin B superantigen, or other molecules) by a cleavable linkage to the radioisotope or compound.

Antiviral therapeutic agent, especially anti-influenza drugs, can be delivered by conjugation to a LEAPS™ heteroconjugate or to an mAb. Alternatively, antiviral therapeutic agents can be delivered by lysosomal means. The two main classes of antiviral therapeutic agents used against influenza are neuraminidase inhibitors, such as zanamivir (RELENZA™) and oseltamivir (TAMIFLU™), or inhibitors of the viral M2 protein, such as amantadine (SYMMETREL™) and rimantadine (FLUMADINE™). Some interferons either normal (non-pegylated) or pegylated and especially forms that can be conjugated or delivered by lysosomal encapsulated methods may also be useful in severe cases.

Conjugation of an antiviral therapeutic agent or any other therapeutic agent or a dye can be done through the selective use or engineering of an amino acid residue to conjugate to the antiviral therapeutic agent. For example, a cysteine or lysine residue can be engineered into the LEAPS™ heteroconjugates to serve as a conjugation site for a therapeutic compound. Other active sites for attachment on other amino acids include OH groups on serine or threonine residues, COOH groups on aspartic or glutamic acid residues, the carboxyl terminal COOH, amide groups on glutamine or asparagine residues, $NH_2$ on amino terminal amino acid or lysine residues, and —$SCH_3$ groups on methionine residues. A therapeutic agent or a dye conjugated to a LEAPS™ heteroconjugates or to an mAb that can in turn be conjugated to DCs via the LEAPS™ heteroconjugates or the mAb.

In a further embodiment, the LEAPS™ heteroconjugate or an mAb can be conjugated to a fluorescent dye. Suitable dyes include but are not limited to N,N'di-carboxypentyl-indodicarbocyanine-5,5'-disulfonic acid (Cy5.5), Alexa Fluor® probes, carboxyfluorescein succinimidyl ester (CFSE), 4-N(S-glutathionylacetylaminophenyl)arsenoxide-Cy5.5, 2,3-dicyanonaphthalene-Cy5.5 or Alexa Fluor, or CFSE and other near-infrared probes. Additional NIR probes include Cy 5.5 covalently linked to 4-N(S-glutathionylacetylaminophenyl)arsenoxide-Cy5.5 and 2,3-dicyanonaphthalene-Cy5.5. Additionally, DCs can be directly stained by carboxyfluorescein succinimidyl ester (CFSE). In particular, Cy 5.5, Alexa Flour® and other NIR dyes exhibit low absorption of the NIR signal in tissue at operating wavelengths and may be quenched by conjugation of two or more NIR probe molecules together. Cleavage of the conjugation bonds results in fluorescence dequenching and generation of a signal that is suitable for imaging. A fluorescent image can be made by endoscopy or by taking a tissue biopsy. A tissue biopsy can be examined by flow cytometry to identify the presence of fluorescent cells.

EXAMPLES

Preparation of Bone Marrow Cells

Bone marrow (BM) cells were extracted from the femurs and tibias of BALB/c mice using a sterile disposable 27 g needle. The ends of the femurs and tibias were removed to expose the bone marrow, and the BM cells were flushed out with Hanks Balanced Salt Solution (HBSS). BM cells were washed with HBSS, passed through a Nytex filter, and red blood cells were lysed with ACK buffer ($NH_4Cl$, $KHCO_3$, EDTA, neutral pH 6-8-7.4). The BM cells were suspended in culture medium containing RPMI at a concentration of approximately $5 \times 10^6$ cells/mL.

The remaining BM cells were decanted from the plastic tissue culture flasks and further washed and resuspended in RPMI medium with 10% fetal calf serum (FCS) containing 20 ng/mL murine recombinant (GM-CSF) at a concentration of approximately 1 to $1.5 \times 10^6$ cells/mL. BM cells were incubated in RPMI medium with 10% FCS containing 20 ng/mL GM-CSF at 37° C. by seeding approximately $1 \times 10^6$ BM cells per well in well culture plates or approximately $50 \times 10^6$ BM cells in tissue culture flasks. Following 2 days and 4 days of incubation, the culture media was replaced with fresh RPMI medium with 10% FCS containing 20 ng/mL GM-CSF. BM cells were harvested after 8 days.

Phenotyping of BM Cells

The BM cells after incubation with GM-CSF were analyzed for expression of CD3, CD19, CD11c, CD86, MHC II and F4/80 (CD80). At least $10^6$ cells were analyzed by flow cytometry (Altra FACS, Beckman Coulter) using forward and side scatter parameters to limit the immunofluorescence analysis to cells having the size and granularity anticipated for monocytes and dendritic cells. In FIG. 1A, two-dimensional flow cytometry data for the isolated BM cells are presented. Immunofluorescence analysis was limited to cells having forward and side scatter parameters falling within the boxed region marked on FIG. 1A.

The BM cells were labeled with an appropriate antibody-fluorescent conjugate for each cell surface marker analyzed. The antibody-fluorescent conjugates used are indicated in Table 4. All antibody-fluorescent conjugates are commercially available and have affinity to the mouse (anti-mouse) cell surface markers as indicated. Flow cytometry analysis was also performed using an appropriate isotype control, as indicated in Table 4.

TABLE 4

Antibody-fluorescent conjugates for flow cytometry

| Surface Marker | Antibody Conjugate | Clone | Source | Isotype Control |
|---|---|---|---|---|
| CD3 | CD3-PerCP | 145-2C11 | BD[1] | PerCP hamster IGg1 Kappa |
| CD19 | CD19-PerCP-Cy5.5 | 1D3 | BD | PerCP cy5.5 rat Ig2a Kappa |
| CD11c | CD11c-Alexa488 | N418 | eBioscience[2] | Alexa Fluor 488 Hamster IgG1 |
| I-A(d) | I-A(d)-PE | AMS-32.1 | BD | PE mouse IgG2b Kappa |
| CD80 | CD80-PE | 16-10A1 | BD | PE hamster IgG2 Kappa |
| CD86 | CD86-APC | GL1 | BD | APC rat IgG2a Kappa |
| F4/80 | F4/80 FITC | BM8 | eBioscience | FITC rat IgG2a Kappa |

[1]BD Bioscience, 2350 Qume Dr., San Jose, CA 95131
[2]eBioscience, 10255 Science Center Dr., San Diego, CA 92121

The results of flow cytometry analysis of the BM cells are presented in FIGS. 1B through 1F. Fluorescence intensity is presented on the x-axis and normalized cell count is presented on the y-axis in FIGS. 1B through 1F. Results obtained using the surface marker-specific antibody-fluorescent conjugates are shown as unshaded data and results obtained using the corresponding isotype antibody on Table 4 are shown as shaded data. The mean fluorescence value of the peak along the indicated length of the x-axis is shown for each plot in FIGS. 1B through 1F. As can be seen in FIGS. 1D and 1E, significant expression levels for CD11c, MHC II, and CD86 are seen in the BM cells. Lower levels of expression are seen for CD3, CD19 and F4/80. The observed expression of cell surface markers is believed to be typical for DCs and/or monocytes prior to binding to an antigen for presentation. The cell surface marker pattern presented in FIGS. 1B through 1G is believed to indicate the presence of iDCs in the isolated BM cells with little or no matured DCs present. As such, the isolated BM cells were believed to contain BMDCs.

Incubation of BM Cells with LEAPS Peptides and Phenotyping

As described above, flow cytometry analysis for the BM cells incubated with GM-CSF indicated that the BM cells display a phenotype consistent with the presence of iDCs and/or monocytes. These cells were incubated with LEAPS™ heteroconjugate or an appropriate control as described below.

BM cells isolated from mice, as described above, were seeded into a 24-well culture plate at about $10^6$ cells per well in RPMI media with 10% FCS and 20 ng/mL GM-CSF. The BM cells were incubated with GM-CSF media over the course of 8 days and replenished with fresh media after 2 days and 4 days. After 8 days, a specific LEAPS™ heteroconjugate, a control composition or a combination of LEAPS™ heteroconjugates were added to individual wells.

LEAPS™ heteroconjugates were added to individual wells at an amount of 14.5 micromoles. Four different LEAPS™ heteroconjugates were utilized having an antigen peptide derived from influenza virus: J-NP (SEQ ID No. 1), J-M2e (SEQ ID No. 2), J-HA1 (SEQ ID No. 12) and J-HA2 (SEQ ID No. 11). In addition, a LEAPS™ heteroconjugate having an antigen portion derived from p17 gag protein from HIV was used as a control, J-H (DLLKNGERIEK-VEGGGYSVHQRIDVKDTKEALEKIEEEQNKSKKKA) (SEQ ID No. 37). LEAPS™ heteroconjugate J-H is conjugate of Peptide J with and a peptide isolated from the p17 gag protein of HIV, "Protein H" (YSVHQRIDVKDT-KEALEKIEEEQNKSKKKA) (SEQ ID No. 38), through a -GGG- linker. Additional wells were incubated with an approximately equimolar mixture of J-NP, J-M2e, J-HA1 and J-HA2 at a total combined amount of 14.5 micromoles per well. An additional non-LEAPS™ heteroconjugate control was used, lipopolysaccharide (LPS), which was expected to produce a significant immune response.

Figure 2:
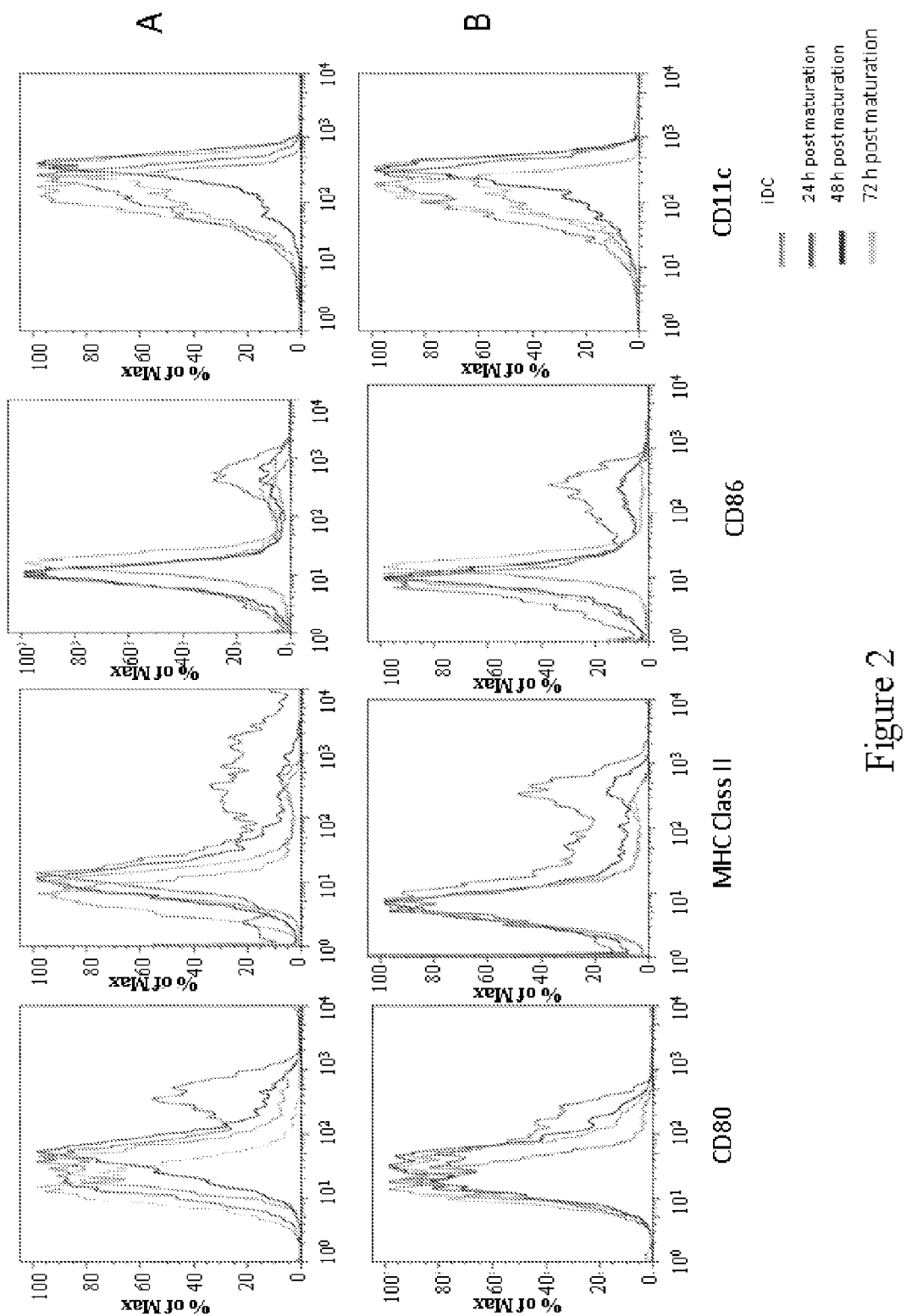
FIGS. 2A through 2D represent flow cytometry data for more matured DCs after treatment with one or more LEAPS™ heteroconjugates or a control immunogen.
Figure 2:
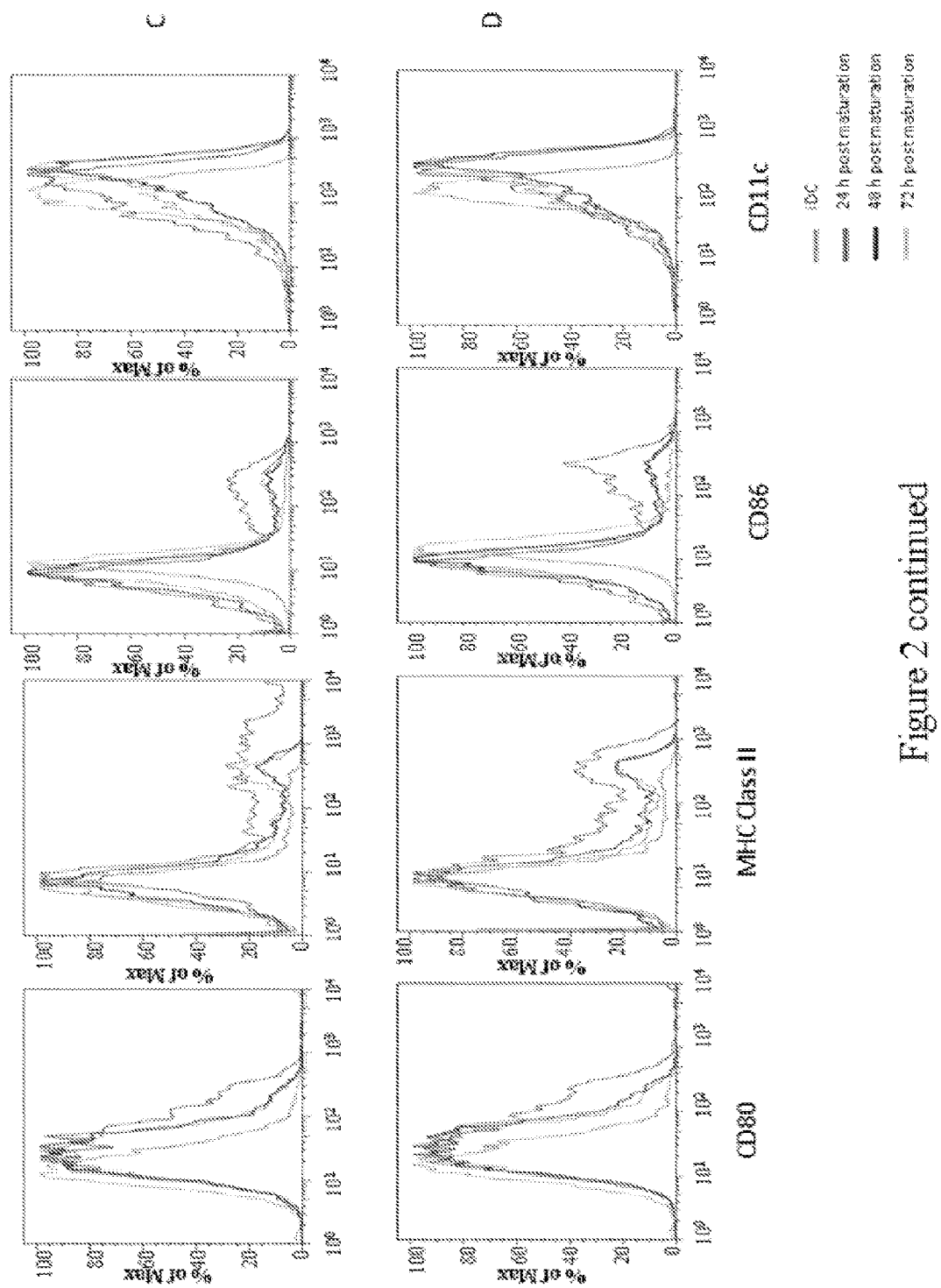
Figure 3:
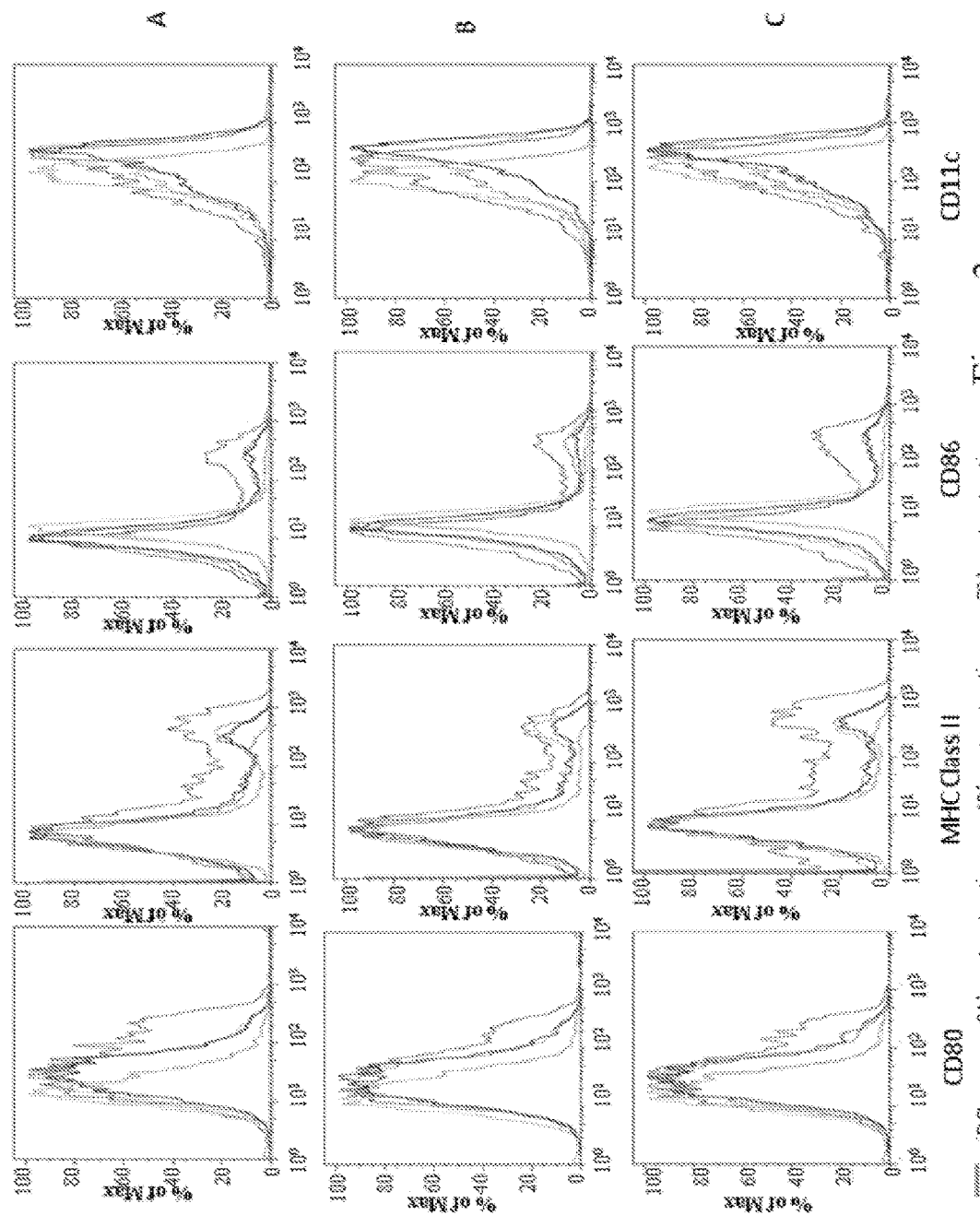
FIGS. 3A through 3C represent flow cytometry data for more matured DCs after treatment with one or more LEAPS™ heteroconjugates.
Figure 4:
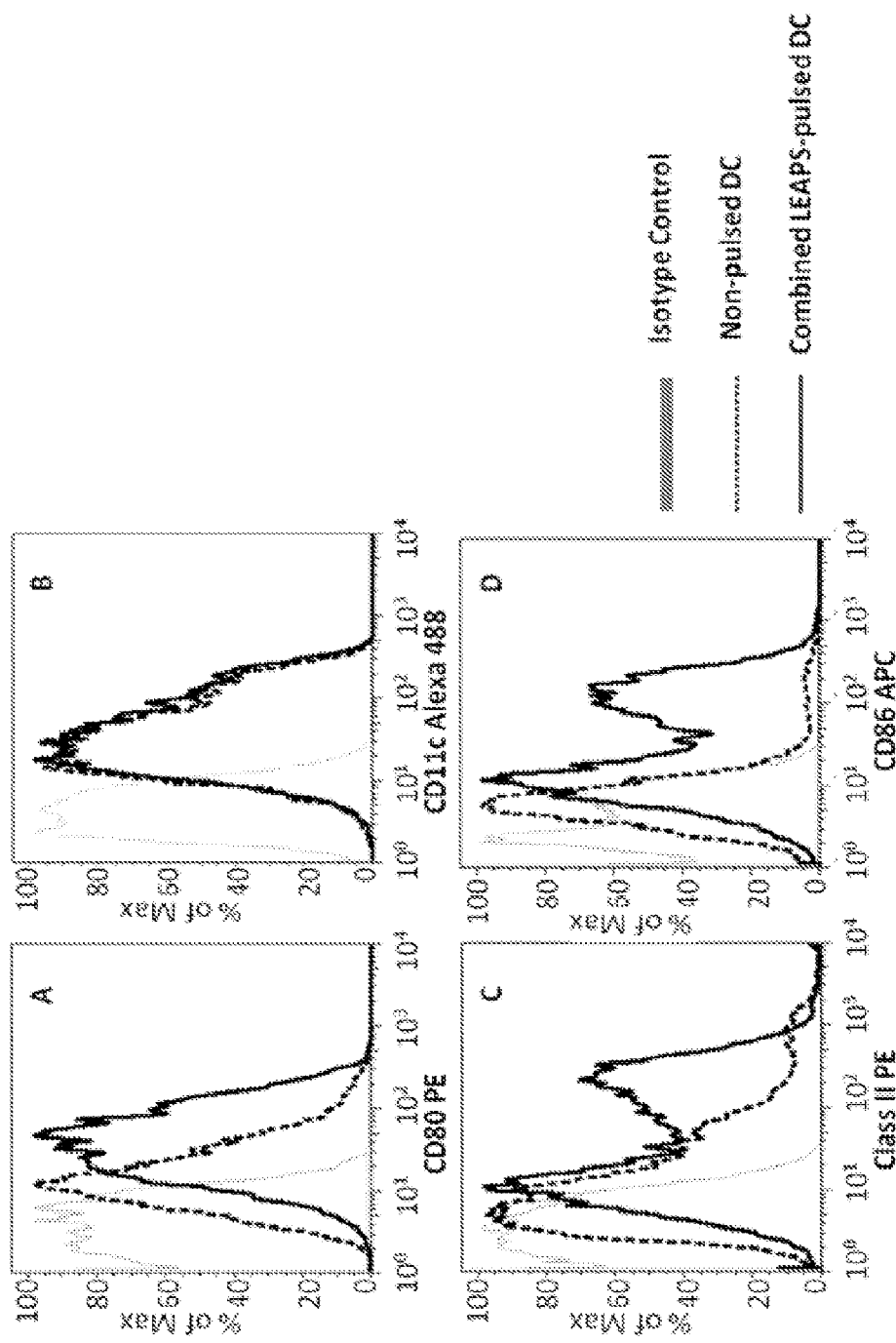
FIGS. 4A through 4D represent flow cytometry data for more matured DCs after contact with a combination of J-H, J-NP, J-M2e, J-HA1 and J-HA2 for a period of 24 hours. Data representing an appropriate isotype control antibody-fluorescent conjugate and DCs not treated with a conjugate are also presented for reference.
Figure 5:
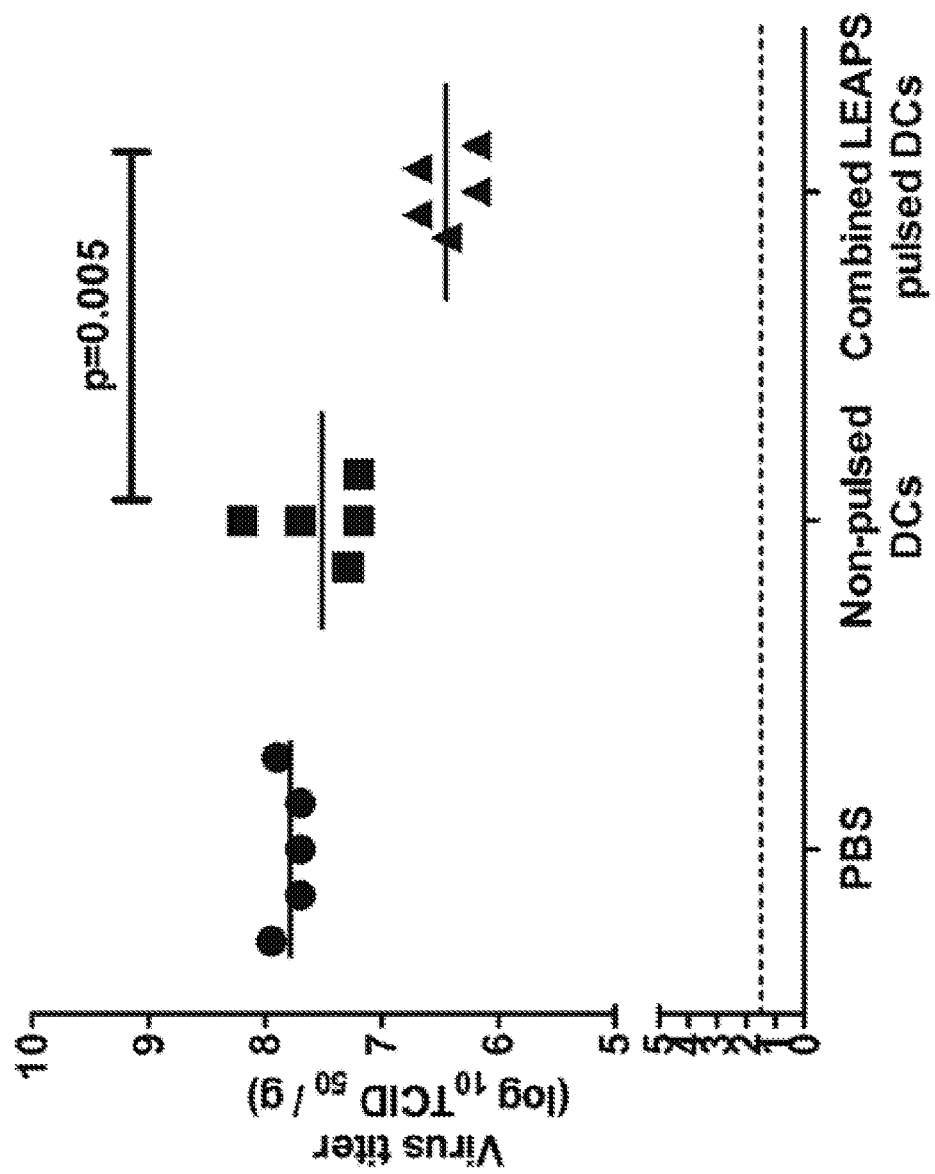
FIG. 5 represents data for the level of viral load observed in lung tissue of mice infected with Type A influenza virus and sacrificed 3 days after treatment with LEAPS™ activated DCs or phosphate-buffer saline (PBS) control DCs. The viral load as measured by standard MDCK TCID$_{50}$ assay is presented for 5 individual mice treated with PBS, 5 individual mice treated with DCs that were not treated with a LEAPS™ heteroconjugate, and 5 individual mice treated with DCs that were treated with a LEAPS™ heteroconjugate. The mean virus level is represented by a horizontal bar.
Figure 6:
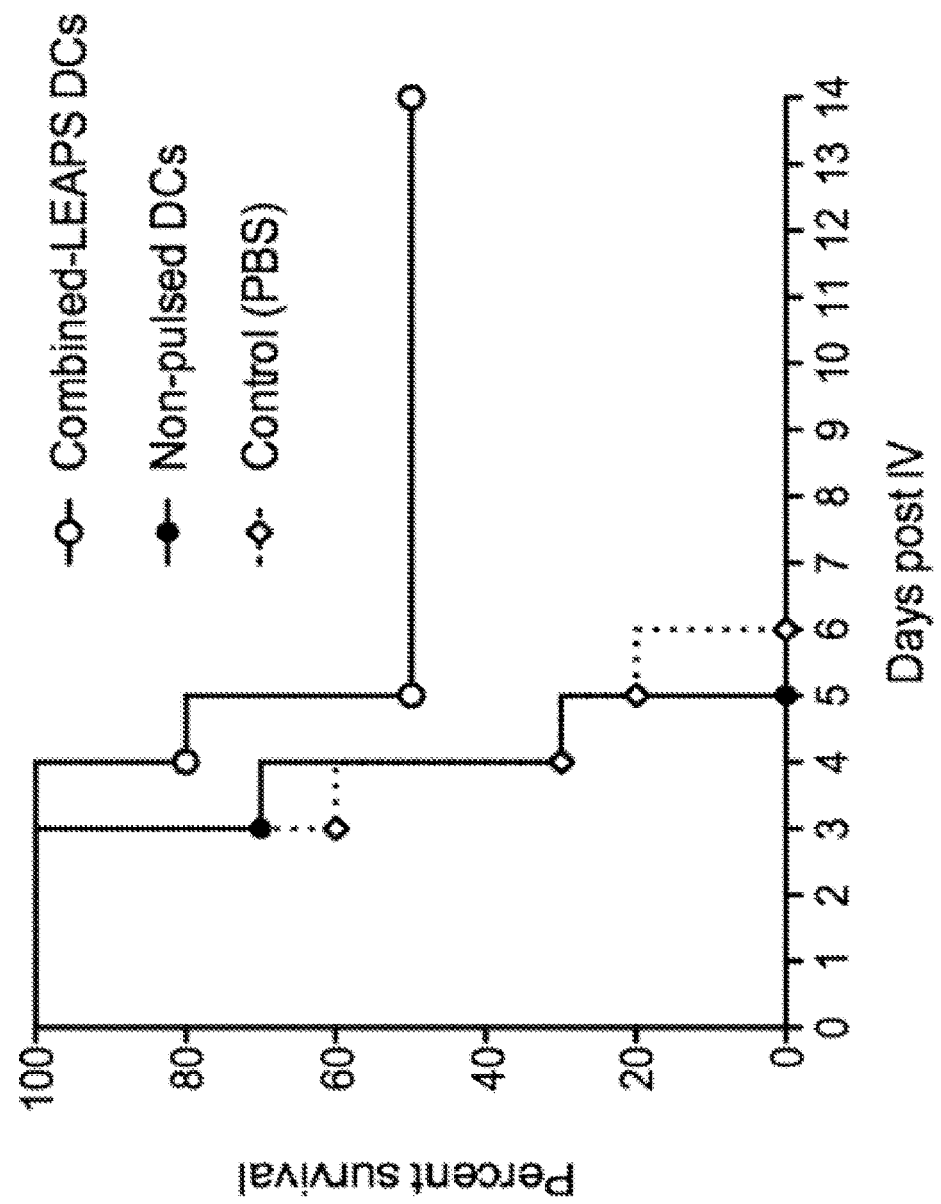
FIG. 6 represents a Kaplan-Meier survival curve for Type A influenza-infected mice. Survival data are presented for a group of 10 individual mice treated with PBS, a group of 10 individual mice treated with DCs not treated with a LEAPS™ heteroconjugate (control animals), and a group of 10 individual mice treated with DCs that were treated with a LEAPS™ heteroconjugate (experimental animals). To further delineate the difference between the control animals and the experimental animals, the experiment was extended to 14 days. As all control animals (challenged but untreated) were dead by day 6, the experimental animals exhibited not just a slowing down of rate of disease progression where the curve endpoints for both groups would ultimately become equivalent, rather the experimental animals exhibited actual long term protection.

BM cells were incubated at 37° C. with the appropriate LEAPS™ heteroconjugate or LPS for a period of 24 hours and harvested. Trials of incubation for periods of 24 hours, 48 hours and 72 hours were also explored; however, 24 hours of incubation was found to yield the most satisfactory maturation signals. The BM cells were analyzed by flow cytometry, in the same manner described above, after incubation with the LEAPS™ heteroconjugate or LPS for a period of 24 hours, 48 hours or 72 hours. Results of flow cytometry are presented in FIGS. 2 and 3. Results are also presented for BM cells (iDCs) not incubated with a LEAPS™ heteroconjugate or LPS. FIGS. 2A through 2D present the cell phenotype generated by contact with control LPS (FIG. 1A) and a control non-influenza LEAPS™ heteroconjugate (J-H, SEQ ID No. 37) (FIG. 1B) along with the cell phenotype generated by contact with influenza-derived LEAPS™ heteroconjugates J-NP1 (FIG. 2C) and J-M2e (FIG. 2D). FIGS. 3A through 3B present the phenotype of addit ficed at 3 days post IV treatment and 10 individuals were observed for 14 days post IV treatment.

Virus titers found in lung tissue of the sacrificed mice 3 days post IV were measured using a standard assay in MDCK cells. The mean virus titers ($\log_{10} \text{TCID}_{50}/\text{g}$) for the non-LEAPS™-activated DC groups treated at 8 and 24 hours post infection were about 7.3 $\text{TCID}_{50}$ $g^{-1}$ and 7.6 $\text{TCID}_{50}$ $g^{-1}$, respectively. The mean virus titers for the LEAPS™ heteroconjugate-activated DC groups treated at 8 and 24 hours were both about 6.1 $\text{TCID}_{50}$ $g^{1}$. The virus titers for the 8-hour non-LEAPS™-activated DC group and the 8-hour LEAPS™ heteroconjugate-activated DC group were compared by paired t test. A similar comparison by t test was also performed for the 24-hour non-LEAPS™-activated DC group and the 24-hour LEAPS™ heteroconjugate-activated DC group. The paired t test yielded p-values of 0.01 and 0.04, respectively. As such, there is a statistical basis to reject a null hypothesis of no difference in viral load between compared groups. Almost no difference was seen in mean virus titers between the 8- and 24-hour LEAPS™ heteroconjugate-activated DC groups. As such, acquired immunity obtainable by treatment with LEAPS™ heteroconjugate-activated DCs does not appear to be time dependent at least within the 24-hour period following infection.

Figure 7:
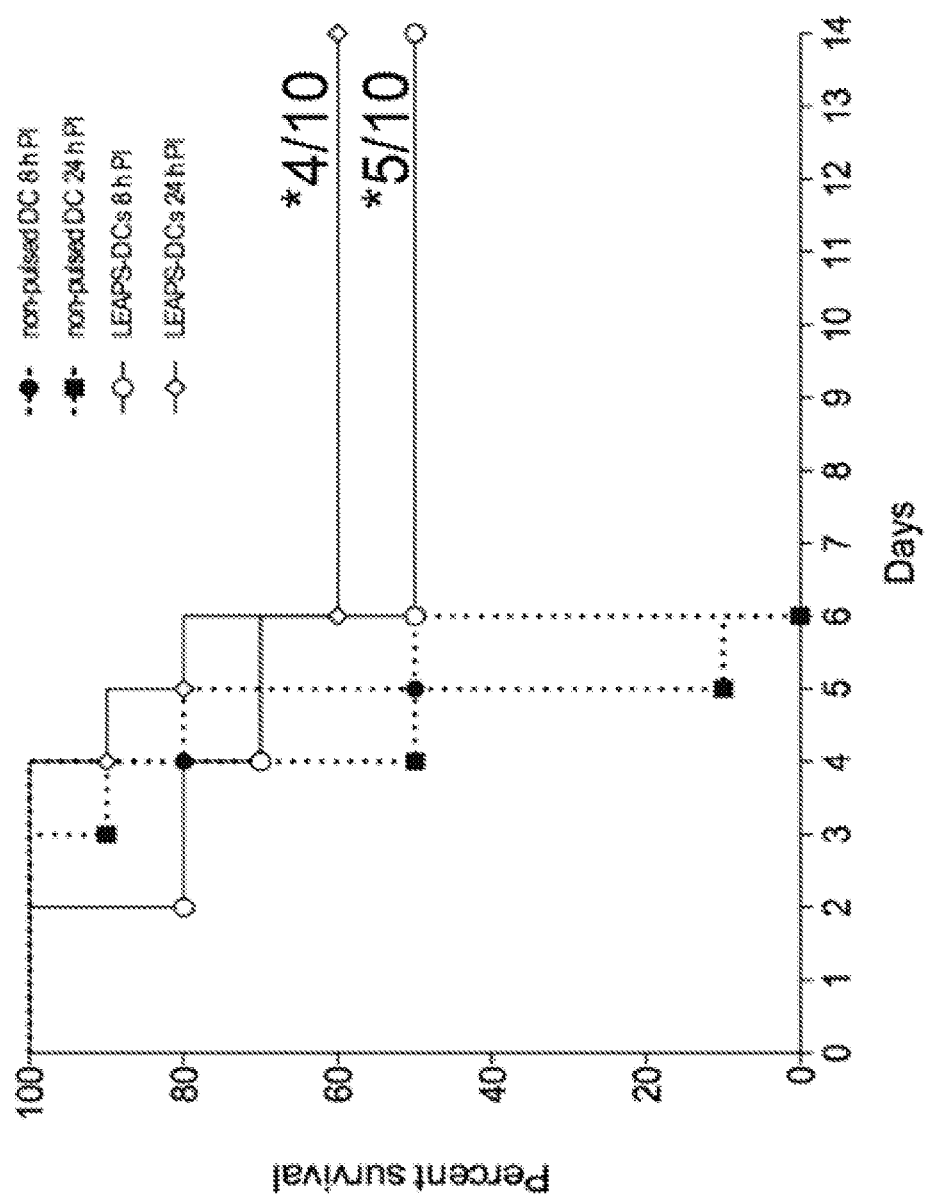
FIG. 7 represents a Kaplan-Meier survival curve for Type A influenza-infected mice. Survival data are presented for a group of 10 individuals treated starting at 8 hours post infection with DCs not treated with a LEAPS™ heteroconjugate' a group of 10 individuals treated starting at 8 hours post infection with DCs treated with a LEAPS™ heteroconjugate, a group of 10 individuals treated starting at 24 hours post infection with DCs not treated with a LEAPS™ heteroconjugate, and a group of 10 individuals treated starting at 24 hours post infection with DCs treated with a LEAPS™ heteroconjugate.

FIG. 7 presents the survival of the 10 mice from each group described above that were not sacrificed at 3 days post treatment. As shown in FIG. 7, approximately half of the LEAPS™ heteroconjugate-activated DC individuals survive while the infection is fatal to all the individuals treated with the non-LEAPS™-activated DCs. Survival for the two 8-hour post-infection treatment groups and the two 24-hour post-infection treatments groups were compared by Mantel-Cox test, with p-value of 0.01 in both instances.

The results presented herein appear to be the first time that DCs matured with a designed, artificial peptide are reported to be sufficient to provide protection from a lethal infection. That is, the results presented here demonstrate the usefulness of LEAPS™ heteroconjugate-activated DCs for combating an active infection and not only for prophylactic use. Taylor et al., *Vaccine* 28 (2010), 5533-43, cited above, reports the use of DCs treated with an artificial peptide for prophylactic use against challenge with HSV-1 virus; however, no indication is made for effectiveness against an active infection. As discussed in Taylor et al., the J Peptide alone does not induce protection against infection nor a change in phenotype of iDCs exposed to Peptide J.

Figure 8:
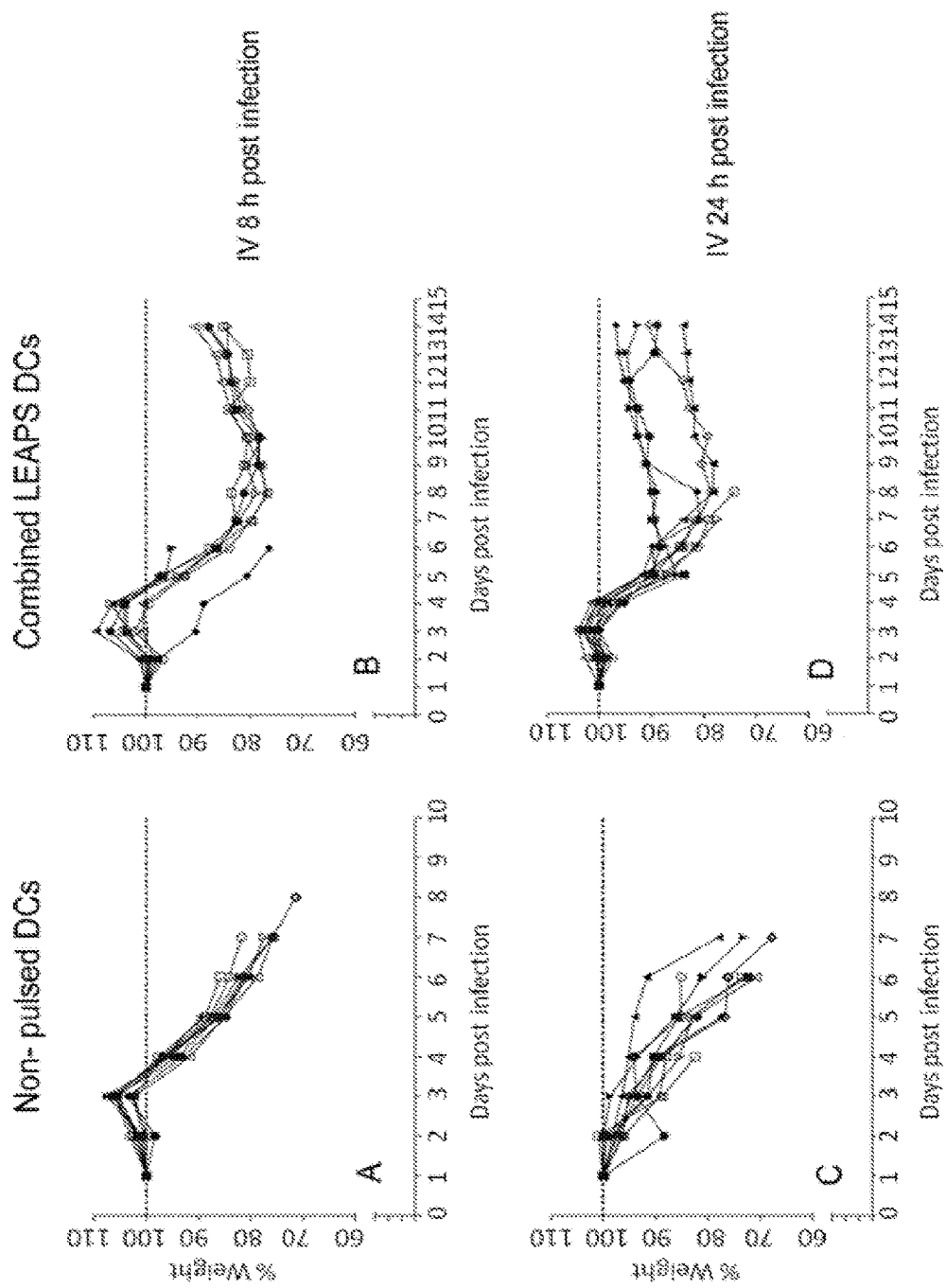
FIGS. 8A through 8D represent the daily weight for mice infected with Type A influenza.

DCs were administered to individual mice after inoculation with competent Type A influenza virus. Even if symptoms are not actively present in the mice, it is presumed that an active infection is on-going prior to treatment with DC cells. The course of influenza infection can be monitored through observation of weight of infected mice. FIG. 8 presents daily weight information for each of the 10 mice in each of the 4 above-described groups. FIG. 8A shows weight for mice treated with non-LEAPS™-activated DCs at 8 hours post infection, FIG. 8B shows weight for mice treated with LEAPS™ heteroconjugate-activated DCs at 8 hours post infection, FIG. 8C shows weight for mice treated with non-LEAPS™-activated DCs at 24 hours post infection, and FIG. 8D shows weight for mice treated with LEAPS™ heteroconjugate-activated DCs at 24 hours post infection.

As seen in FIG. 8, all individual mice contracted an active influenza infection as indicated by significant weight loss. As discussed, about half of the LEAPS™ heteroconjugate-activated DC-treated mice do not survive and succumb to infection within 6 days post infection. At about 6 days post IV treatment, the weight of the LEAPS treated DC surviving mice begins to stabilize and increase as the animals recover. In FIGS. 8A and 8C, no recovery of weight is observed since the infection proves to be fatal in all individuals. Interestingly, the individuals in FIG. 8A representing mice treated with non-LEAPS™-activated DCs at 8 hours post infection appear to have weight gain prior to the development of weight loss. However, regardless of the weight gain observed, DCs cells not activated with the LEAPS™ heteroconjugates do not affect the ultimate survivability from influenza infection.

Distribution of LEAPS Heteroconjugate-Treated DCs

Surprisingly, observations indicate that LEAPS™ heteroconjugate-activated DCs administered to influenza-infected mice by IV were not evenly distributed in the tissue of infected mice. The above-described iDCs were incubated with the combined LEAPS™ heteroconjugates for 24 hours or left in a non-LEAPS™-activated or iDC state. The DCs were then labeled by incubation with 5 µM carboxyfluorescein succinimidyl ester (CSFE) for 30 minutes at 37° C. to fluorescently label the DCs. Those skilled in the art will recognize that the manner for labeling DCs for later detection is not limited to any particular method. For example, DCs can be labeled for later detection by other methods including labeling with other cell surface labeled dyes, or radionuclides. The CSFE-labeled DCs were administered IV into 18 individual mice in two groups: 9 mice were administered $10^7$ non-LEAPS™-activated DCs cells and 9 mice were administered $10^7$ LEAPS™ heteroconjugate-activated DCs, as described-above. 3 individuals in each group were sacrificed at 8, 24 and 48 hours post IV and tissue collected from lung, spleen and lymph nodes.

Figure 9:
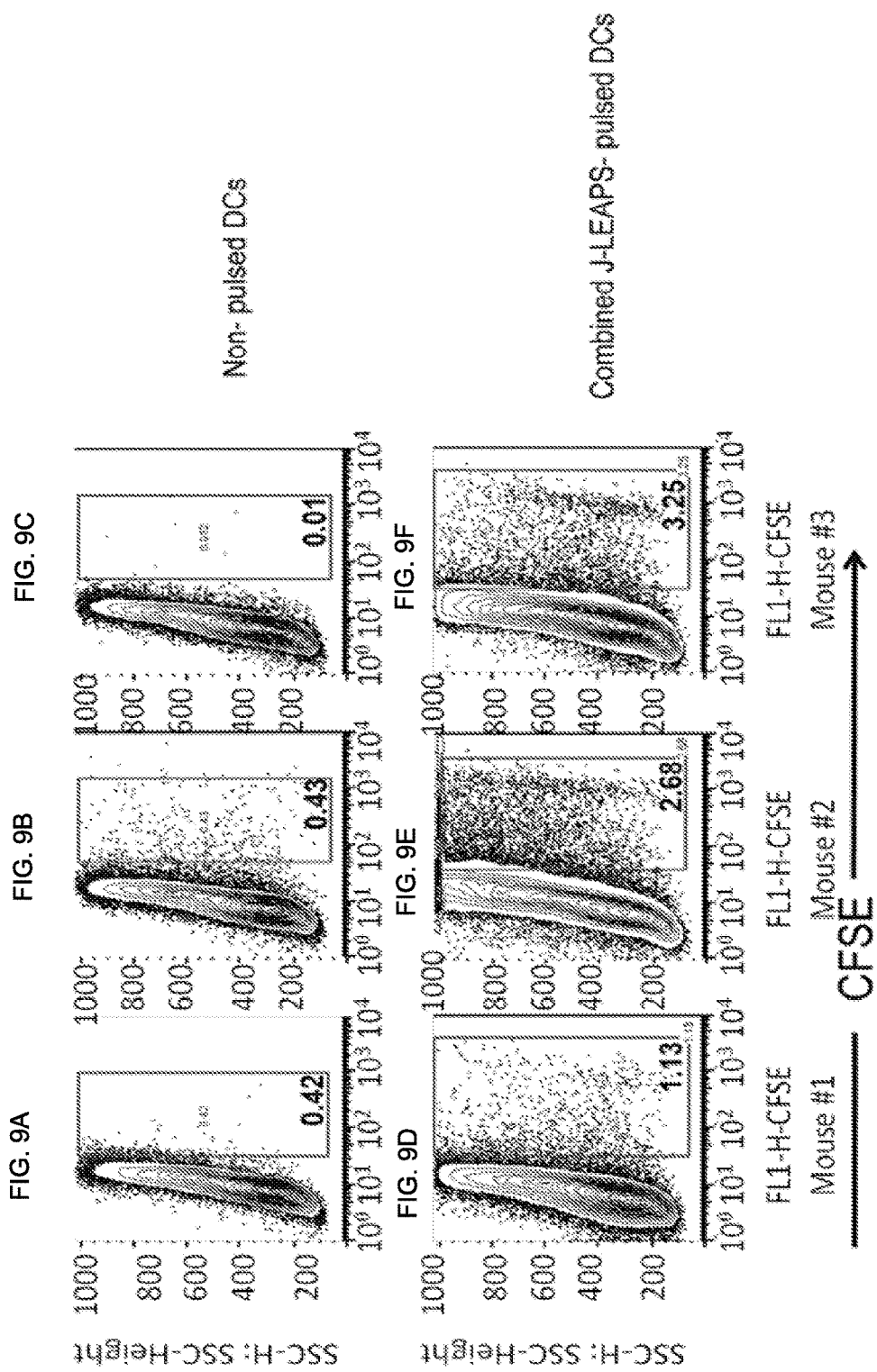
FIGS. 9A through 9F represent flow cytometry data of labeled DCs administered to mice infected with Type A influenza and recovered from lung tissue 8 hours after administration of labeled DCs. DCs were labeled with 5 µM carboxyfluorescein succinimidyl ester (CSFE) for 30 minutes at 37° C., and flow cytometry data was collected for side scatter and CSFE fluorescence.

FIGS. 9A through 9F show two-dimensional flow cytometry data for lung tissue recovered 8 hours after IV administration of DCs. FIGS. 9A-9C show data collected from 3 individual mice treated with non-LEAPS™-activated DCs. FIGS. 9D-9F show data collected from 3 individual mice treated with the combined LEAPS™ heteroconjugate-activated DCs.

The two-dimensional data presented represents CFSE fluorescence intensity and side scattering. The outlined boxes in FIGS. 9A through 9F represent the region where DCs having characteristic side scattering and sufficient fluorescence to indicated CSFE labeling are expected to be found. All mice presented in FIGS. 9A-9F were infused with $10^7$ CSFE-labeled DCs. However, the combined LEAPS™ heteroconjugate-activated DC mice exhibit a much greater level of CSFE-labeled cells in lung tissue compared to the non-LEAPS™-activated DC mice. Mean fluorescent intensity is indicated on FIGS. 9A-9F.

Figure 10:
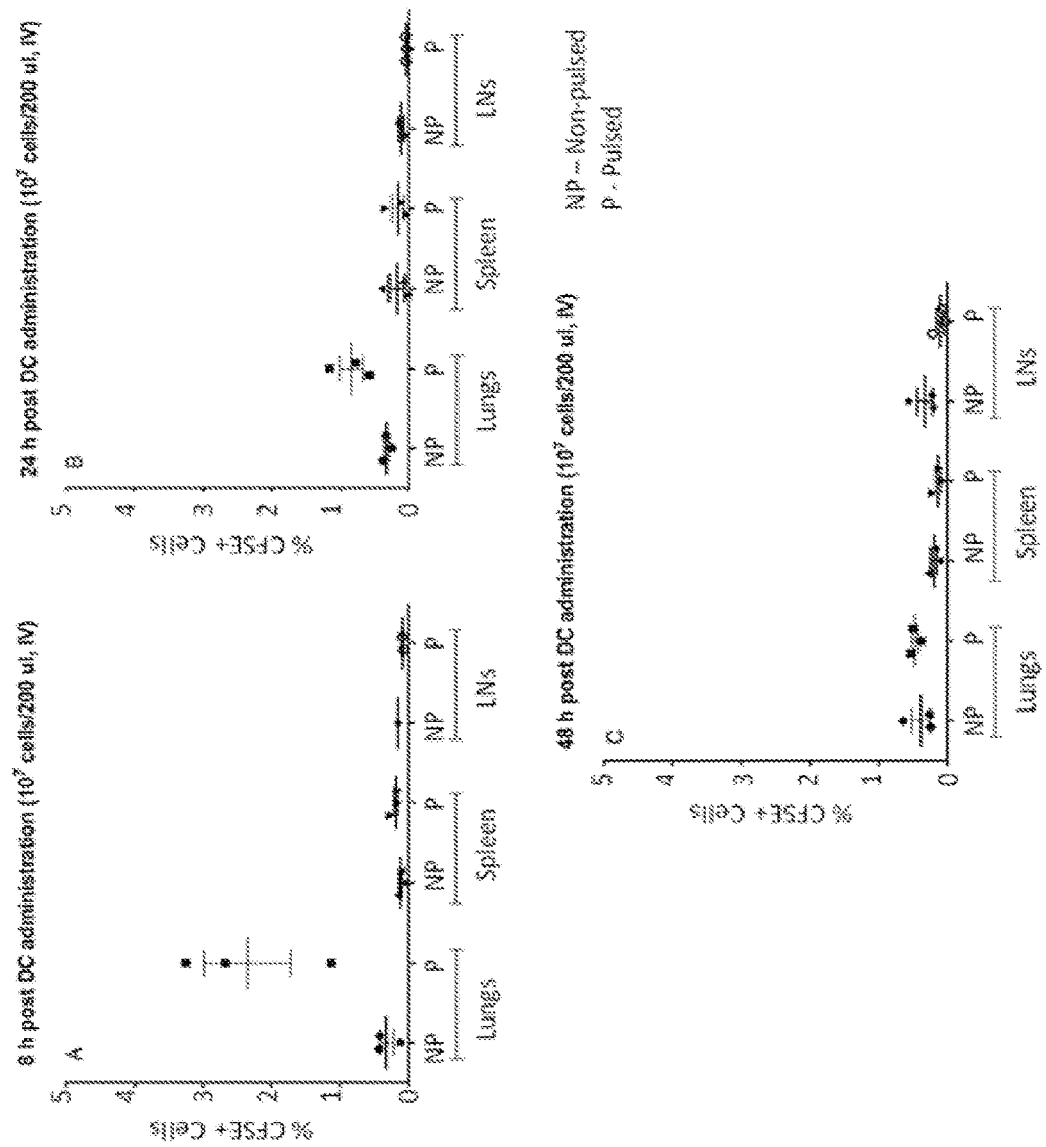
FIGS. 10A through 10C show the distribution of labeled DCs in lung, spleen and lymph node tissue taken at 8 hours (FIG. 10A), 24 hours (FIG. 10B) and 48 hours (FIG. 10C) after administration to mice.

FIGS. 10A through 10C present the CSFE-labeled cell distribution from tissue collected from lung, spleen and lymph nodes at 8 (FIG. 10A), 24 (FIG. 10B) and 48 hours (FIG. 10C) post IV treatment. As mentioned, tissues from 3 individuals were collected at each time point. As seen, a large increase in the number of CSFE-labeled cells is seen in lung tissue for the LEAPS™ heteroconjugate-activated DC mice in FIG. 10A compared to the non-pulsed DC mice. Further, the level of CSF-labeled cells seen in lung is significantly higher than observed in spleen or lymph nodes. As seen in FIGS. 10B and 10C, the level of CSFE-labeled cells found in lung tissue decreases over time at 24 hours and 48 hours post IV. In certain embodiments, a majority of the LEAPS™ heteroconjugate-activated DCs locate to the site of an infection within 8 hours of administration of the DCs to a patient, where the heteroconjugate contains an antigen derived from the organism or virus causing the infection. In certain other embodiments, at least about 30% of the LEAPS™ heteroconjugate-activated DCs locate to the site of an infection within 8 hours of administration of the DCs to a patient, where the heteroconjugate contains an antigen derived from the organism or virus causing the infection.

References
Infectious disease agent Bibliography

| Reference # | Citation |
| --- | --- |
| 1 | Uger RA, Chan SM, Barber BH. Covalent linkage to beta2-microglobulin enhances the MHC stability and antigenicity of suboptimal CTL epitopes. J Immunol. 1999 May 15;162(10):6024-8.; Deliyannis G, Jackson DC, Ede NJ, Zeng W, Hourdakis I, Sakabetis E, Brown LE. Induction of long-term memory CD8(+) T cells for recall of viral clearing responses against influenza virus. J Virol. 2002 May;76(9):4212-21.; Chen W, Antón LC, Bennink JR, Yewdell JW. Dissecting the multifactorial causes of immunodominance in class I-restricted T cell responses to viruses. Immunity. 2000 Jan;12(1):83-93. |
| 2 | Fan J, Liang X, Horton MS, Perry HC, Citron MP, Heidecker GJ, Fu TM, Joyce J, Przysiecki CT, Keller PM, Garsky VM, Ionescu R, Rippeon Y, Shi L, Chastain MA, Condra JH, Davies ME, Liao J, Emini EA, Shiver JW. Preclinical study of influenza virus A M2 peptide conjugate vaccines in mice, ferrets, and rhesus monkeys. Vaccine. 2004 Aug 13;22(23-24):2993-3003.; Mozdzanowska K, Feng J, Eid M, Kragol G, Cudic M, Otvos L Jr, Gerhard W. Induction of influenza type A virus-specific resistance by immunization of mice with a synthetic multiple antigenic peptide vaccine that contains ectodomains of matrix protein 2. Vaccine. 2003 Jun 2;21(19-20):2616-26.; Reid AH, Fanning TG, Janczewski TA, McCall S, Taubenberger JK. Characterization of the 1918 "Spanish" influenza virus matrix gene segment. J Virol. 2002 Nov;76(21):10717-23.; Feng J, Zhang M, Mozdzanowska K, Zharikova D, Hoff H, Wunner W, Couch RB, Gerhard W. Influenza A virus infection engenders a poor antibody response against the ectodomain of matrix protein 2. Virol J. 2006 Dec 6;3:102.; Zhang M, Zharikova D, Mozdzanowska K, Otvos L, Gerhard W. Fine specificity and sequence of antibodies directed against the ectodomain of matrix protein 2 of influenza A virus. Mol Immunol. 2006 Jul;43(14):2195-206. Epub 2006 Feb 10.; Zharikova D, Mozdzanowska K, Feng J, Zhang M, Gerhard W. Influenza type A virus escape mutants emerge in vivo in the presence of antibodies to the ectodomain of matrix protein 2. J Virol. 2005 Jun;79(11):6644-54. |
| 3 | Prabhu N. et al., Monoclonal antibodies against the fusion peptide ofhemagglutinin protect mice from lethal influenza A virus H5N1 infection, J. Virol., Mar. 2009;83(6):2553-62, epub Dec. 24 2008 |
| 4 | Sui J. et al., Structural and functional bases for broad-spectrum neutralization of avian and human influenza A viruses, Nat. Struct. Mol. Biol., Mar.2009; 16(3):233-4. Ekiert D.C. et al., Antibody recognition of a highly conserved influenza virus epitope, Science, Apr. 10 2009; 324(5924):246-51, epub Feb 26. 2009<br>Items 1-4 are also shown by the following accession numbers are available from "The NCBI handbook [Internet]. Bethesda (MD): National Library of Medicine (US), National Center for Biotechnology Information; 2002 Oct. Chapter 18, The Reference Sequence (RefSeq) Project. Available from http://www.ncbi.nlm.nih.gov/entrez/query.fcgi?db = Books" |
| 5 | Tan PT, Khan AM, August JT. Highly conserved influenza A sequences as T cell epitopes-based vaccine targets to address the viral variability. Human vaccines 2011 Apr;7(4):402-9.<br>Items 6-39 shown by the following accession numbers are available from "The NCBI handbook [Internet]. Bethesda (MD): National Library of Medicine (US), National Center for Biotechnology Information; 2002 Oct. Chapter 18, The Reference Sequence (RefSeq) Project. Available from http://www.ncbi.nlm.nih.gov/entrez/query.fcgi?db = Books." |
| 6 | Protein Sequence Identification Number GI: 31260974 |
| 7 | Protein Sequence Identification Number GI: 195561808 |
| 8 | Protein Sequence Identification Number GI: 327554159 |
| 9 | Protein Sequence Identification Number GI: 317160605 |
| 10 | Protein Sequence Identification Number GI: 317160574 |
| 11 | Protein Sequence Identification Number GI: 301078817 |
| 12 | Protein Sequence Identification Number GI: 301078803 |
| 13 | Protein Sequence Identification Number GI: 82469328 |
| 14 | Protein Sequence Identification Number GI: 294510591 |
| 15 | Protein Sequence Identification Number GI: 329317733 |
| 16 | Protein Sequence Identification Number GI: 327322724 |
| 17 | Protein Sequence Identification Number GI: 296936111 |
| 18 | Protein Sequence Identification Number GI: 118573902 |
| 19 | Protein Sequence Identification Number GI: 239775095 |
| 20 | Protein Sequence Identification Number GI: 110666853 |
| 21 | Protein Sequence Identification Number GI: 260099978 |
| 22 | Protein Sequence Identification Number GI: 145904955 |
| 23 | Protein Sequence Identification Number GI: 326579756 |
| 24 | Protein Sequence Identification Number GI: 2246490 |
| 25 | Protein Sequence Identification Number GI: 9625941 |
| 26 | Protein Sequence Identification Number GI: 30575434 |
| 27 | Protein Sequence Identification Number GI: 30575485 |
| 28 | Protein Sequence Identification Number GI: 226000962 |

References
Infectious disease agent Bibliography

| Reference # | Citation |
|---|---|
| 29 | Protein Sequence Identification Number GI: 260162094 |
| 30 | Protein Sequence Identification Number GI: 270504657 |
| 31 | Protein Sequence Identification Number GI: 283099868 |
| 32 | Protein Sequence Identification Number GI: 291060256 |
| 33 | Protein Sequence Identification Number GI: 293651071 |
| 34 | Protein Sequence Identification Number GI: 323903353 |
| 35 | Protein Sequence Identification Number GI: 154744649 |
| 36 | Protein Sequence Identification Number GI: 222478375 |
| 37 | Protein Sequence Identification Number GI: 222478403 |
| 38 | Protein Sequence Identification Number GI: 295848592 |
| 39 | Protein Sequence Identification Number GI: 30575485 |
| 40 | Andre LA Oliveira, Jimmunol, 2009 |
| 41 | Bihl F, et al. 2007. Lytic and latent antigens of the human gammaherpesviruses Kaposi's sarcoma-associated herpesvirus and Epstein-Barr virus induce T-cell responses with similar functional properties and memory phenotypes. J Virol, 81:4904-8. |
| 42 | Brander C, et al. 2001. Definition of an optimal cytotoxic T lymphocyte epitope in the latently expressed Kaposi's sarcoma-associated herpesvirus kaposin protein. J Infect Dis, 184:119-26. |
| 43 | Caccamo N, et al. 2009. Analysis of Mycobacterium tuberculosis-specific CD8 T-cells in patients with active tuberculosis and in individuals with latent infection. PLoS One, 4:e5528 |
| 44 | Chen Y, et al. 2008. BKV and JCV large T antigen-specific CD8+ T cell response in HLA A*0201+ kidney transplant recipients with polyomavirus nephropathy and patients with progressive multifocal leukoencephalopathy. J Clin Virol, 42:198-202 |
| 45 | Chentoufi AA, et al. 2010. A novel HLA (HLA-A*0201) transgenic rabbit model for preclinical evaluation of human CD8+ T cell epitope-based vaccines against ocular herpes. J Immunol, 184:2561-71 |
| 46 | Ding J, et al. 2010. Identification of HLA-A24-Binding Peptides of Mycobacterium tuberculosis Derived Proteins with Beta 2m Linked HLA-A24 Single Chain Expressing Cells. Immunol Invest |
| 47 | Firbas C, et al. 2010. Immunogenicity and safety of different injection routes and schedules of IC41, a Hepatitis C virus (HCV) peptide vaccine. Vaccine |
| 48 | Frey CR, et al. 2003. Identification of CD8+ T cell epitopes in the immediate early 62 protein (IE62) of varicella-zoster virus, and evaluation of frequency of CD8+ T cell response to IE62, by use of IE62 peptides after varicella vaccination. J Infect Dis, 188:40-52. |
| 49 | Graham S, et al. 1993. Analysis of the human T-cell response to picornaviruses: identification of T-cell epitopes close to B-cell epitopes in poliovirus. J Virol, 67:1627-37 |
| 50 | Harndahl Mikkel, et al. 2010. Large scale analysis of peptide-HLA class I interactions |
| 51 | Hayward AR. 1990. T-cell responses to predicted amphipathic peptides of varicella-zoster virus glycoproteins II and IV. J Virol, 64:651-5. |
| 52 | Holland MJ, et al. 2006. The frequency of Chlamydia trachomatis major outer membrane protein-specific CD8+ T lymphocytes in active trachoma is associated with current ocular infection. Infect Immun, 74:1565-72 |
| 53 | Jolivert I&I 55 1498 |
| 54 | Kim S, et al. 2010. Single-chain HLA-A2 MHC trimers that incorporate an immundominant peptide elicit protective T cell immunity against lethal West Nile virus infection. J Immunol, 184: 4423-30 |
| 55 | Kinchington PR, et al. 1988. Identification and Characterization of a Varicella-Zoster Virus DNA-Binding Protein by Using Antisera Directed against a Predicted Synthetic Oligopeptide. J Virol, 62:802-9. |
| 56 | Klade CS, et al. 2009. Hepatitis C virus-specific T cell responses against conserved regions in recovered patients. Vaccine, 27:3099-108 |
| 57 | Koelle DM, et al. 2008. Phase I dose-escalation study of a monovalent heat shock protein 70-herpes simplex virus type 2 (HSV-2) peptide-based vaccine designed to prime or boost CD8 T-cell responses in HSV-na & Atilde; & macr;ve and HSV-2-infected subjects. Clin Vaccine Immunol, 15:773-82 |
| 58 | Kotturi MF, et al. 2009. Of mice and humans: how good are HLA transgenic mice as a model of human immune responses? Immunome Res, 5:3 |
| 59 | Leen AM, et al. 2004. Conserved CTL epitopes on the adenovirus hexon protein expand subgroup cross-reactive and subgroup-specific CD8+ T cells. Blood |
| 60 | Marzocchetti A, et al. 2009. Efficient in vitro expansion of JC virus-specific CD8(+) T-cell responses by JCV peptide-stimulated dendritic cells from patients with progressive multifocal leukoencephalopathy. Virology, 383:173-7 |
| 61 | Morgan, C.A., et al. Segregation o fB and T cell epitopes of Treponema pallidum repeat protein K to variable and conserved regions during experimental syphilis infection, J Immunol, 2002, 169, 952-957 |

References
Infectious disease agent Bibliography

| Reference # | Citation |
|---|---|
| 62 | Oba DE, et al. 1988. Induction of Antibodies to the Epstein-Barr Virus Glycoprotein gp85 with a Synthetic Peptide Corresponding to a Sequence in the BXLF2 Open Reading Frame. J Virol, 62:1108-14. |
| 63 | Pfaff et al 88 or 85 JV 144-159 |
| 64 | Pim LJ, et al. 2009. Identification of varicella-zoster virus-specific CD8 T cells in patients after T-cell-depleted allogeneic stem cell transplantation. J Virol, 83:7361-4 |
| 65 | Prato S, et al. 2006.: Cross-presentation of a human malaria CTL epitope is conformation dependent. Mol Immunol, 43:2031-6 |
| 66 | Riedl P, et al. 2009. Elimination of immunodominant epitopes from multispecific DNA-based vaccines allows induction of CD8 T cells that have a striking antiviral potential. J Immunol, 183:370-80 |
| 67 | Riemer AB, et al. 2010. A conserved E7-derived cytotoxic T lymphocyte epitope expressed on human papillomavirus 16-transformed HLA-A2+ epithelial cancers. J Biol Chem, 285:29608-22 |
| 68 | Schneidawind D, et al. 2010. Polyomavirus BK-specific CD8+ T cell responses in patients after allogeneic stem cell transplant. Leuk Lymphoma, 51:1055-62 |
| 69 | Simons J, et al. 1993. Characterization of poliovirus-specific T lymphocytes in the peripheral blood of Sabin-vaccinated humans. J Virol, 67:1262-8 |
| 70 | Stebbing J, et al. 2003. Kaposi's sarcoma-associated herpesvirus cytotoxic T lymphocytes recognize and target Darwinian positively selected autologous K1 epitopes. J Virol; 77:4306-14. |
| 71 | Terrosi C, et al. 2007. Immunological characterization of respiratory syncytial virus N protein epitopes recognized by human cytotoxic T lymphocytes. Viral Immunol, 20:399-406 |
| 72 | Tynan FE, et al. 2005. The immunogenicity of a viral cytotoxic T cell epitope is controlled by its MHC-bound conformation. J Exp Med, 202:1249-60. |
| 73 | van der Heiden PL, et al. 2009. Identification of varicella-zoster virus-specific CD8 T cells in patients after T-cell-depleted allogeneic stem cell transplantation. J Virol, 83:7361-4. |
| 74 | Wilkinson J, et al. 2002. Identification of Kaposi's sarcoma-associated herpesvirus (KSHV)-specific cytotoxic T-lymphocyte epitopes and evaluation of reconstitution of KSHV-specific responses in human immunodeficiency virus type 1-Infected patients receiving highly active antiretroviral therapy. J Virol; 76:2634-40. |
| 75 | Zhong J, et al. 2008. Induction of pluripotent protective immunity following immunisation with a chimeric vaccine against human cytomegalovirus. PLoS One. 3:e3256 |
| 76 | Zweig M, Showalter SD, Simms DJ, Hampar B. Antibodies to a synthetic oligopeptide that react with herpes simplex virus type 1 and 2 glycoprotein C. J Virol. 1984 Aug;51(2):430-6. |
| 77 | Uger RA, Chan SM, Barber BH. Covalent linkage to beta2-microglobulin enhances the MHC stability and antigenicity of suboptimal CTL epitopes. J Immunol. 1999 May 15;162(10):6024-8.; Deliyannis G, Jackson DC, Ede NJ, Zeng W, Hourdakis I, Sakabetis E, Brown LE. Induction of long-term memory CD8(+) T cells for recall of viral clearing responses against influenza virus. J Virol. 2002 May;76(9):4212-21.; Chen W, Antón LC, Bennink JR, Yewdell JW. Dissecting the multifactorial causes of immunodominance in class I-restricted T cell responses to viruses. Immunity. 2000 Jan;12(1):83-93. |
| 78 | Fan J, Liang X, Horton MS, Perry HC, Citron MP, Heidecker GJ, Fu TM, Joyce J, Przysiecki CT, Keller PM, Garsky VM, Ionescu R, Rippeon Y, Shi L, Chastain MA, Condra JH, Davies ME, Liao J, Emini EA, Shiver JW. Preclinical study of influenza virus A M2 peptide conjugate vaccines in mice, ferrets, and rhesus monkeys. Vaccine. 2004 Aug 13;22(23-24):2993-3003.; Mozdzanowska K, Feng J, Eid M, Kragol G, Cudic M, Otvos L Jr, Gerhard W. Induction of influenza type A virus-specific resistance by immunization of mice with a synthetic multiple antigenic peptide vaccine that contains ectodomains of matrix protein 2. Vaccine. 2003 Jun 2;21(19-20):2616-26.; Reid AH, Fanning TG, Janczewski TA, McCall S, Taubenberger JK. Characterization of the 1918 "Spanish" influenza virus matrix gene segment. J Virol. 2002 Nov;76(21):10717-23.; Feng J, Zhang M, Mozdzanowska K, Zharikova D, Hoff H, Wunner W, Couch RB, Gerhard W. Influenza A virus infection engenders a poor antibody response against the ectodomain of matrix protein 2. Virol J. 2006 Dec 6;3:102.; Zhang M, Zharikova D, Mozdzanowska K, Otvos L, Gerhard W. Fine specificity and sequence of antibodies directed against the ectodomain of matrix protein 2 of influenza A virus. Mol humunol. 2006 Jul;43(14):2195-206. Epub 2006 Feb 10.; Zharikova D, Mozdzanowska K, Feng J, Zhang M, Gerhard W. Influenza type A virus escape mutants emerge in vivo in the presence of antibodies to the ectodomain of matrix protein 2. J Virol. 2005 Jun;79(11):6644-54. |
| 79 | Prabhu N. et al., Monoclonal antibodies against the fusion peptide of hemagglutinin protect mice from lethal influenza A virus H5N1 infection, J. Virol., Mar. 2009;83(6):2553-62, epub Dec. 24 2008 |

References
Infectious disease agent Bibliography

| Reference # | Citation |
|---|---|
| 80 | Sui J. et al., Structural and functional bases for broad- spectrum neutralization of avian and human influenza A viruses, Nat. Struct. Mol. Biol., Mar.2009; 16(3):233-4. Ekiert D.C. et al., Antibody recognition of a highly conserved influenza virus epitope, Science, Apr. 10 2009; 324(5924):246-51, epub Feb 26. 2009 |
| 81 | Harboe M, Malin AS, Dockrell HS, Wiker HG, Ulvund G, Holm A, Jørgensen MC, Andersen P. B-cell epitopes and quantification of the ESAT-6 protein of Mycobacterium tuberculosis. Infect Immun. 1998 Feb;66(2):717-23. |
| 82 | OConnor TP, Esty KJ, Hanscom JL, Shields P, Philipp MT. Dogs vaccinated with common Lyme disease vaccines do not respond to IR6, the conserved immunodominant region of the VlsE surface protein of Borrelia burgdorferi. Clin Diagn Lab Immunol. 2004 May;11(3):458-62. |
| 83 | Horowitz A, et al. 2009. Use of immobilized HLA-A2:Ig dimeric proteins to determine the level of epitope-specific, HLA-restricted CD8(+) T-cell response. Scand J Immunol, 70:415-22. |
| 84 | Kostense S, et al. 2002. Functional restoration of human immunodeficiency virus and Epstein-Barr virus-specific CD8(+) T cells during highly active antiretroviral therapy is associated with an increase in CD4(+) T cells. Eur J Immunol, 32:1080-9. |
| 85 | van Baarle D, et al. 2001. Dysfunctional Epstein-Barr virus (EBV)-specific CD8(+) T lymphocytes and increased EBV load in HIV-1 infected individuals progressing to AIDS-related non-Hodgkin lymphoma. Blood, 98:146-55. |
| 86 | Aldhamen, YA et al. Expression of the SLAM family of receptors adapter EAT-2 as a novel strategy for enhancing beneficial immune responses to vaccine antigens. J Immunol. 186, 722-732 (2011). |
| 87 | Votteler, J et al. Highly convserved serine residue 40 in HIV-1 p6 regulates capsid processing and virus core assembly. Retrovirology, 8, (2011) |
| 88 | Wilson CC, et al. 2003. Development of a DNA Vaccine Designed to Induce Cytotoxic T Lymphocyte Responses to Multiple Conserved Epitopes in HIV-1. J Immunol, 171:5611-23. |
| 89 | Amrani A, et al. 2001. Expansion of the antigenic repertoire of a single T cell receptor upon T cell activation. J Immunol, 167:655-66. |
| 90 | Ausubel LJ, et al. 2005. Characterization of in vivo expanded OspA-specific human T-cell clones. Clin Immunol, 115:313-22. |
| 91 | Harboe M, et al. 1998. e: B-cell epitopes and quantification of the ESAT-6 protein of Mycobacterium tuberculosis Infect Immun, 66:717-23. |
| 92 | Tully G, et al. 2005. Highly focused T cell responses in latent human pulmonary Mycobacterium tuberculosis infection. J Immunol, 174:2174-84. |
| 93 | Weichold FF, et al. 2007. Impact of MHC class I alleles on the M. tuberculosis antigen-specific CD8+ T-cell response in patients with pulmonary tuberculosis. Genes Immun, 8:334-43. Items 94-103 shown by the following accession numbers are available from "The NCBI handbook [Internet]. Bethesda (MD): National Library of Medicine (US), National Center for Biotechnology Information; 2002 Oct. Chapter 18, The Reference Sequence (RefSeq) Project. Available from http://www.ncbi.nlm.nih.gov/entrez/query.fcgi?db = Books." |
| 94 | Protein Sequence Identification Number GI:15644780 |
| 95 | Protein Sequence Identification Number GI:29027589 |
| 96 | Protein Sequence Identification Number GI:295366328 |
| 97 | Protein Sequence Identification Number GI:323717628 |
| 98 | Protein Sequence Identification Number GI:327475068 |
| 99 | Protein Sequence Identification Number GI:327745 |
| 100 | Protein Sequence Identification Number GI:332139121 |
| 101 | Protein Sequence Identification Number GI:332321176 |
| 102 | Protein Sequence Identification Number GI:332673306 |
| 103 | Protein Sequence Identification Number GI:332715316 |
| 104 | Protein Sequence Identification Number GI:91980330 |
| Seq ID 7 | Accession No. GI:333778347 |
| Seq ID 8 | Accession No. GI:329047495 |
| Seq ID 10 | Accession No. GI:333125981 |
| Seq ID 9 | Accession No. GI:333125981 |

We claim:

1. A method for delivering a therapeutic agent to an infection site in a subject, comprising:
    contacting immature dendritic cells or monocytes with a peptide construct ex vivo under conditions suitable for maturation of the cells to form the matured dendritic cells; and
    administering an effective amount of the matured dendritic cells to the subject,
    wherein a majority of the matured dendritic cells administered to the subject locate to the infection site,
    wherein a separate therapeutic agent is conjugated to the peptide construct or an antibody such that the separate therapeutic agent is delivered to the infection site when the matured dendritic cells are administered to the subject, and
    wherein the peptide construct has the formula $P_1$-x-$P_2$ or $P_2$-x-$P_1$, wherein
    a. $P_2$ represents a specific antigenic peptide derived from a Type A Influenza virus competent for recognition by a class or subclass of immune cells or binding to an antibody;

b. $P_1$ is selected from the group consisting of SEQ ID NOs: 3-6 and 40 or a modification thereof wherein the modification is a modification to either or both of an N- or C-terminal of the sequence by any one or more of amidation or acylation; and c. x represents a covalent bond or a divalent linking group.

2. The method of claim 1, wherein the peptide construct is selected from the group consisting of SEQ ID NOs: 1-2, 11-36, 47-52, 140-189 and 209-218 or a modification thereof; wherein the modification is a modification to either or both of an N- or C-terminal of the sequence by any one or more of amidation or acylation.

3. The method of claim 1, wherein the immature dendritic cells or monocytes are collected from the subject, and where the cells after maturation are introduced back into the subject in an autologous fashion.

4. The method of claim 1, wherein an anti-influenza drug is conjugated to the matured dendritic cells via the antibody.

5. The method of claim 1, wherein the separate therapeutic agent is one or more anti-influenza drugs selected from a group consisting of zanamivir, oseltamivir, amantadine, rimantadine, non-pegylated interferons and pegylated interferons.

6. The method of claim 1, wherein the peptide construct is conjugated to an anti-influenza drug.

7. A method for treating a subject, comprising:

administering an effective amount of a peptide construct optionally with an adjuvant to the subject or administering an effective amount of matured dendritic cells to the subject, wherein the peptide construct has the formula $P_1$-x-$P_2$ or $P_2$-x-$P_1$, wherein $P_2$ is selected from the group consisting of SEQ ID NOs: 7-10, 41-46, 53-139 and 190-208 or a modification thereof wherein the modification is a modification to either or both of an N- or C-terminal of the sequence by any one or more of amidation or acylation, $P_1$ is selected from the group consisting of SEQ ID NOs: 3-6 and 40, or a modification thereof wherein the modification is a modification to either or both of an N- or C-terminal of the sequence by any one or more of amidation or acylation, and x represents a covalent bond or a divalent linking group; and the matured dendritic cells are formed by contacting immature dendritic cells or monocytes with the peptide construct having the formula $P_1$-x-$P_2$ or $P_2$-x-$P_1$ under conditions suitable for maturation of the cells to form matured dendritic cells, wherein the peptide construct or the matured dendritic cells are administered to the subject prophylactically.

8. The method of claim 7, wherein the immature dendritic cells or monocytes are collected from the subject, and where the cells after maturation are introduced back into the subject in an autologous fashion.

9. The method of claim 7, wherein the peptide construct is selected from the group consisting of SEQ ID NOs: 1-2, 11-36, 47-52, 140-189 and 209-218.

10. The method of claim 7, wherein the peptide construct is administered with an adjuvant that is selected from the group consisting of Freund's incomplete adjuvant, a liposomal adjuvant, and a water-in-oil or a water-in-oil-in-water formulation.

11. A method for modulating an immune response in a subject, comprising:

administering an effective amount of a peptide construct optionally with an adjuvant to the subject or administering an effective amount of matured dendritic cells to the subject, wherein the peptide construct has the formula $P_1$-x-$P_2$ or $P_2$-x-$P_1$, wherein $P_2$ is selected from the group consisting of SEQ ID NOs: 7-10, 41-46, 53-139 and 190-208 or a modification thereof wherein the modification is a modification to either or both of an N- or C-terminal of the sequence by any one or more of amidation or acylation, $P_1$ is selected from the group consisting of SEQ ID NOs: 3-6 and 40 or a modification thereof wherein the modification is a modification to either or both of an N- or C-terminal of the sequence by any one or more of amidation or acylation, and x represents a covalent bond or a divalent linking group; and the matured dendritic cells are formed by contacting immature dendritic cells or monocytes with the peptide construct having the formula $P_1$-x-$P_2$ or $P_2$-x-$P_1$ under conditions suitable for maturation of the cells to form matured dendritic cells, wherein the peptide construct or the matured dendritic cells are administered to the subject having an active infection.

12. The method of claim 11, wherein the immature dendritic cells or monocytes are collected from the subject, and where the cells after maturation are introduced back into the subject in an autologous fashion.

13. The method of claim 11, wherein the peptide construct is selected from the group consisting of SEQ ID NOs: 1-2, 11-36, 47-52, 140-189 and 209-218.

* * * * *